United States Patent [19]
Ohshima et al.

[11] Patent Number: 5,744,487
[45] Date of Patent: Apr. 28, 1998

[54] PROLINEAMIDE DERIVATIVES

[75] Inventors: Masahiro Ohshima; Norimichi Iwase; Shigeo Sugiyama; Koichi Sugawara; Misao Okitsu; Yoshikuni Tamao; Yasuhiro Morinaka, all of Yokohama, Japan

[73] Assignee: Mitsubishi Chemical Corporation, Japan

[21] Appl. No.: 378,615

[22] Filed: Jan. 26, 1995

[30] Foreign Application Priority Data

Jan. 27, 1994 [JP] Japan .................................. 6-007733

[51] Int. Cl.$^6$ .......................... A61K 31/40; C07D 207/09
[52] U.S. Cl. .......................... 514/326; 514/423; 546/208; 548/406; 548/532; 548/533; 548/535; 548/537; 548/538
[58] Field of Search .......................... 514/423, 326; 546/208; 548/406, 532, 533, 535, 537, 538

[56] References Cited

U.S. PATENT DOCUMENTS 5,153,176 10/1992 Abe et al. .................................. 514/18
5,380,713 1/1995 Balasubramanian .................... 514/18

FOREIGN PATENT DOCUMENTS 526877 2/1993 European Pat. Off. .
0601459A2 6/1994 European Pat. Off. .
WO9315756 8/1993 WIPO .

OTHER PUBLICATIONS

*Chemical Abstracts*, vol. 104, No. 7, Abstract No. 47665b (Feb. 17, 1986).
*Chemical Abstract Service (CAS) Registry Handbook*, 1986 Suppl. (STN DATABASE) RN99742-41-3.
*Chemical Abstracts*, vol. 103, No. 3, Abstract No. 18900y (Jul. 22, 1985).
*Chemical Abstracts*, vol. 92, No. 3, Abstract No. 17850z, (Jan. 21, 1980).

*Primary Examiner*—Johann Richter
*Assistant Examiner*—Taofiq A. Solola
*Attorney, Agent, or Firm*—Wenderoth, Lind & Ponack

[57] ABSTRACT

A prolineamide derivative represented by the formula (I):

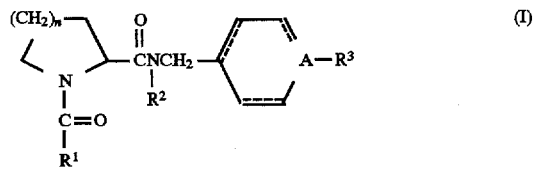

or a salt or hydrate thereof or a pharmaceutically acceptable salt thereof, which has a protease inhibition activity and is useful as an active ingredient of pharmaceutical compositions is provided.

9 Claims, No Drawings

PROLINEAMIDE DERIVATIVES

FIELD OF THE INVENTION

The present invention relates to novel proline derivatives. More particularly, it relates to proline derivatives having a protease inhibition activity or pharmaceutically acceptable salts thereof and protease inhibitors containing the same as an active ingredient.

BACKGROUND OF THE INVENTION

It has been known that various proteases are present in the living body, for example, a group of serine proteases such as thrombin, factor Xa, factor IXa, factor VIIa, trypsin, plasmin, tissue plasminogen activator, kallikrein, C3/C5 convertase in the complement system, tryptase, etc. is known. Further, it is also known that these proteases cause various diseases when they are activated abnormally by some reason. Accordingly, substances which inhibit the activity of these proteases are useful as a clinical remedy. For example, antithrombin agents, anti-factor Xa agents and anti-factor VIIa agents are useful for treating thrombosis, antitrypsin agents are useful for treating pancreatitis, antiplasmin agents are useful as hemostatics, antiallergic agents and antiinflammatory agents, antikallikrein agents are useful as a remedy for inflammation and ulcer, and anticomplementary agents are useful as a remedy for nephritis and rheumatoid arthritis. Protease inhibitors having these actions have hitherto been developed, but they are not necessarily sufficient for practical use in view of protease inhibition activity, stability in the living body and the like. For example, tripeptide derivatives consist of arginine derivatives are known as protease inhibitors. That is, D-phenylalanyl-L-prolyl-L-arginal is known as a thrombin inhibitor (e.g. Folia Haematol., 109, 22 (1982)) but is fairly unstable in the living body (J. Med. Chem., 33, 1729 (1990)). Further, arginal derivatives (Japanese Laid-open Patent Publication No. 4-89498) or amidinophenylalanine derivatives (Thromb. Res., 17, 425 (1980)) are reported as protease inhibitors but their inhibition activity is low.

Under these circumstances, the present inventors have studied to develop structurally novel drugs having enzyme inhibition activity and stability in vivo, which are sufficient for practical use. As a result, it has been found that certain prolineamide derivatives can attain the desired object, thus the present invention has been established.

SUMMARY OF THE INVENTION

That is, the present invention provides a prolineamide derivative represented by the formula (I):

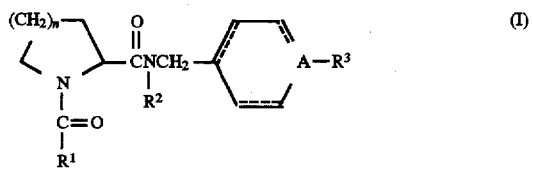

wherein A is a carbon atom or a nitrogen atom; n is an integer of 0 to 2; a broken line is absent or a single bond; $R^1$ is

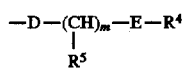

{wherein D and E independently indicate a single bond or an optionally branched $C_1$–$C_6$ alkylene group;

$R^4$ is a $C_1$–$C_6$ alkyl group, —$OR^6$ ($R^6$ is a hydrogen atom, a $C_1$–$C_6$ alkyl group, an optionally substituted $C_6$–$C_{10}$ aryl group, an optionally substituted $C_3$–$C_8$ cycloalkyl group or an optionally substituted $C_7$–$C_{12}$ aralkyl group), —$SR^7$ ($R^7$ is a $C_1$–$C_6$ alkyl group, an optionally substituted $C_6$–$C_{10}$ aryl group, an optionally substituted $C_3$–$C_8$ cycloalkyl group or an optionally substituted $C_7$–$C_{12}$ aralkyl group), —$SOR^8$ ($R^8$ is an optionally substituted $C_6$–$C_{10}$ aryl group or an optionally substituted $C_3$–$C_8$ cycloalkyl group), —$SO_2R^9$ ($R^9$ is an optionally substituted $C_6$–$C_{10}$ aryl group or an optionally substituted $C_3$–$C_8$ cycloalkyl group), —$COR^{10}$ ($R^{10}$ is a hydroxyl group, a $C_1$–$C_6$ alkoxy group, an optionally substituted $C_6$–$C_{10}$ aryl group or an optionally substituted $C_3$–$C_8$ cycloalkyl group), —$NHR^{11}$ ($R^{11}$ is a $C_1$–$C_6$ alkyl group, an optionally substituted $C_6$–$C_{10}$ aryl group, an optionally substituted $C_3$–$C_8$ cycloalkyl group or an optionally substituted $C_7$–$C_{12}$ aralkyl group), —$NHCOR^{12}$ ($R^{12}$ is a $C_1$–$C_6$ alkoxy group, an optionally substituted $C_6$–$C_{10}$ aryl group, an optionally substituted $C_3$–$C_8$ cycloalkyl group or an optionally substituted $C_7$–$C_{12}$ aralkyloxy group), —$NHSO_2R^{13}$ ($R^{13}$ is a $C_1$–$C_6$ alkyl group, an optionally substituted $C_6$–$C_{10}$aryl group, an optionally substituted $C_3$–$C_8$ cycloalkyl group, an optionally substituted $C_7$–$C_{12}$ aralkyl group, an optionally substituted 5- to 10-membered heterocyclic group), an optionally substituted $C_6$–$C_1$ aryl group, an optionally substituted $C_3$–$C_8$ cycloalkyl group, an optionally substituted 5- to 10membered heterocyclic group or —$SiR^{14}R^{15}R^{16}$ ($R^{14}$, $R^{15}$, and $R^{16}$ independently indicate a $C_1$–$C_6$ alkyl group);

$R^5$ is a —$OR^{17}$ ($R^{17}$ is a hydrogen atom, —$SiR^{22}R^{23}R^{24}$ ($R^{22}$, $R^{23}$, and $R^{24}$ independently indicate a $C_1$–$C_6$ alkyl group), a $C_1$–$C_6$ alkyl group or an optionally substituted 5- to 10-membered heterocyclic group)), —$OCOR^{18}$ ($R^{18}$ is a hydrogen atom, a $C_1$–$C_6$ alkyl group, a $C_1$–$C_6$ alkoxy group, an amino group, a $C_1$–$C_6$ alkylamino group, a $C_2$–$C_{12}$ dialkylamino group or a $C_2$–$C_7$ alkenylamino group), —$NHR^{19}$ ($R^{19}$ is a hydrogen atom, a $C_1$–$C_6$ alkyl group or an optionally substituted $C_7$–$C_{12}$ aralkyl group), —$NHCOR^{20}$ ($R^{20}$ is a hydrogen atom, a $C_1$–$C_6$ alkyl group, a $C_1$–$C_6$ haloalkyl group, a $C_1$–$C_6$ alkoxy group, an optionally substituted $C_3$–$C_8$ cycloalkyl group, a $C_2$–$C_7$ carboxyalkyloxy group, a $C_2$–$C_7$ alkenyloxy group, an optionally substituted $C_6$–$C_{10}$ aryl group, an optionally substituted $C_6$–$C_{10}$ aryloxy group, a $C_3$–$C_9$ alkoxycarbonylalkoxy group, a $C_2$–$C_{12}$ dialkylamino group or an optionally substituted $C_7$–$C_{12}$ aralkyloxy group) or —$NHSO_2R^{21}$ ($R^{21}$ is a $C_1$–$C_6$ alkyl group, a $C_1$–$C_6$ haloalkyl group, a $C_2$–$C_7$ carboxyalkyl group, an optionally substituted $C_6$–$C_{10}$aryl group, a $C_3$–$C_9$ alkoxycarbonylalkyl group or an optionally substituted $C_7$–$C_{12}$ aralkyl group); and m is 0 or 1};

$R^2$ is a hydrogen atom or a $C_1$–$C_6$ alkyl group; and $R^3$ is —$C(=NR^{25})NH_2$ ($R^{25}$ is a hydrogen atom, a $C_1$–$C_6$ alkyl group, a $C_2$–$C_7$ acyl group, a $C_2$–$C_7$ acyloxy group, a $C_1$–$C_6$ alkoxy group, a $C_2$–$C_7$ alkoxycarbonyl group, a $C_2$–$C_7$ alkoxycarbonyloxy group, a hydroxyl group or a $C_2$–$C_7$ hydroxyalkylcarbonyloxy group), —NH—$C(=NR^{25})NH_2$ ($R^{25}$ is as defined above) or —$NHR^{26}$ ($R^{26}$ is a hydrogen atom, a $C_1$–$C_6$ alkyl group, a $C_2$–$C_7$ acyl group, a $C_2$–$C_7$ alkoxycarbonyl group or a 5-$C_1$–$C_3$ alkyl-1,3-dioxol-2-on-4-ylmethyl group; provided that $R^3$ is —$C(=NR^{25})NH_2$ when A is a nitrogen atom or a salt and pharmaceutical use thereof.

DETAILED DESCRIPTION OF THE INVENTION

The prolineamide derivative of the present invention is represented by the above formula (I). Examples of the optionally branched $C_1$–$C_6$ alkylene group in the above definition include —$CH_2$—, —$(CH_2)_2$—, —$(CH_2)_3$—, —$(CH_2)_4$—, —$(CH_2)_5$—, —$(CH_2)_6$—, —$CH(CH_3)$—, —$C(CH_3)_2$—, —$CH(CH_3)CH_2$—, —$CH_2CH(CH_3)$—, —$C(CH_3)_2CH_2$—, —$CH_2C(CH_3)_2$—, —$CH(CH_3)CH(CH_3)$— and the like. Examples of the $C_1$–$C_6$ alkyl group include methyl group, ethyl group, n-propyl group, i-propyl group, n-butyl group, s-butyl group, i-butyl group, t-butyl group, n-pentyl group, n-hexyl group and the like. Examples of the $C_1$–$C_3$ alkyl group include those having three carbon atoms or less among those illustrated above. Examples of the $C_1$–$C_6$ alkoxy group include methoxy group, ethoxy group, n-propoxy group, i-propoxy group, n-butyloxy group, s-butyloxy group, i-butyloxy group, t-butyloxy group, n-pentyloxy group, n-hexyloxy group and the like. Examples of the $C_2$–$C_7$ alkoxycarbonyl group include methoxycarbonyl group, ethoxycarbonyl group, n-propoxycarbonyl group, i-propoxycarbonyl group, n-butyloxycarbonyl group, t-butyloxycarbonyl group, n-pentyloxycarbonyl group, n-hexyloxycarbonyl group and the like. Examples of the $C_3$–$C_8$ cycloalkyl group include cyclopropyl group, cyclobutyl group, cyclopentyl group, cyclohexyl group, cycloheptyl group, cyclooctyl group and the like. Examples of the $C_6$–$C_{10}$ aryl group include phenyl group, tolyl group, naphthyl group and the like. Examples of the $C_7$–$C_{12}$ aralkyl group include benzyl group, phenylethyl group, phenylpropyl group, naphthylmethyl group and the like. Examples of the $C_6$–$C_{10}$ aryloxy group include phenyloxy group, naphthyloxy group and the like. Examples of the $C_7$–$C_{12}$ aralkyloxy group include benzyloxy group, phenylethyloxy group, phenylpropyloxy group, naphthylmethyloxy group and the like. Examples of the heterocyclic group include those contain 1 to 4 heteroatoms selected from an oxygen atom, a sulfur atom and a nitrogen atom and the total number of atoms constituting the ring is 5 to 10, specifically, respective residues of furan ring, tetrahydrofuran ring, pyran ring, benzofuran ring, chroman ring, thiophene ring, benzothiophene ring, pyrrole ring, imidazole ring, pyrazole ring, triazole ring, pyridine ring, piperidine ring, pyrazine ring, piperazine ring, pyrimidine ring, indole ring, benzimidazole ring, purine ring, quinoline ring, phthalazine ring, quinazoline ring, cinnoline ring, oxazole ring, thiazole ring, morpholine ring and the like. Examples of the $C_1$–$C_6$ haloalkyl group include chloromethyl group, bromomethyl group, dichloromethyl group, 1-chloroethyl group, 2-chloroethyl group, 3-chloropropyl group, 4-chlorobutyl group, 5-chloropentyl group, 6-chlorohexyl group, difluoromethyl group, trifluoromethyl group and the like. Examples of the $C_2$–$C_7$ carboxyalkyl group include carboxymethyl group, 2-carboxyethyl group, 3-carboxypropyl group, 4-carboxybutyl group, 5-carboxypentyl group, 6-carboxyhexyl group and the like. Examples of the $C_2$–$C_7$ carboxyalkyloxy group include carboxymethoxy group, 2-carboxyethoxy group, 3-carboxypropoxy group, 4-carboxybutyloxy group, 5-carboxypentyloxy group, 6-carboxyhexyloxy group and the like. Examples of the $C_2$–$C_7$ alkenyloxy group include vinyloxy group, aryloxy group, 2-propenyloxy group, isopropenyloxy group, 3-butenyloxy group, 4-pentenyloxy group, 5-hexenyloxy group and the like. Examples of the $C_2$–$C_7$ alkenylamino group include vinylamino group, arylamino group, 2-propenylamino group, isopropenylamino group, 3-butenylamino group, 4-pentenylamino group, 5-hexenylamino group and the like. Examples of the $C_1$–$C_6$ alkylamino group include methylamino group, ethylamino group, n-propylamino group, n-butylamino group and the like. Examples of the $C_2$–$C_{12}$ dialkylamino group include dimethylamino group, methylethylamino group, diethylamino group, di-n-propylamino group and the like. Examples of the $C_2$–$C_7$ acyl group include acetyl group, propionyl group, butyryl group, isobutyryl group, valeryl group, isovaleryl group, pivaroyl group, hexanoyl group, heptanoyl group and the like. Examples of the $C_2$–$C_7$ acyloxy group include acetyloxy group, propionyloxy group, butyryloxy group, isobutyryloxy group, valeryloxy group, isovaleryloxy group, pivaroyloxy group, hexanoyloxy group, heptanoyloxy group and the like. Examples of the $C_2$–$C_7$ alkokycarbonyloxy group include methoxycarbonyloxy group, ethoxycarbonyloxy group, n-propoxycarbonyloxy group, n-butyloxycarbonyloxy group, n-pentyloxycarbonyloxy group, n-hexyloxycarbonyloxy group and the like. Examples of the $C_2$–$C_7$ hydroxyalkylcarbonyloxy group include hydroxymethylcarbonyloxy group, 2-hydroxyethylcarbonyloxy group, 3 hydroxypropylcarbonyloxy group, 4-hydroxybutylcarbonyloxy group, 5hydroxypentylcarbonyloxy group, 6-hydroxyhexylcarbonyloxy group and the like. Examples of the $C_3$–$C_9$ alkoxycarbonylalkoxy group include methoxycarbonylmethoxy group, ethoxycarbonylmethoxy group, propoxycarbonylmethoxy group, methoxycarbonylethoxy group, ethoxycarbonylethoxy group, propoxycarbonylethoxy group and the like. Examples of the $C_3$–$C_9$ alkoxycarbonylalkyl group include methoxycarbonylmethyl group, ethoxycarbonylmethyl group, propoxycarbonylmethyl group, methoxycarbonylethyl group, methoxycarbonylmethyl group, propoxycarbonylethyl group and the like.

Examples of the substituent in the above definition of "optionally substituted (with substituent)" include above-described $C_1$–$C_6$ alkyl group; above-described $C_1$–$C_6$ haloalkyl group; above-described $C_1$–$C_6$ alkoxy group; hydroxyl group; carboxyl group; above-described $C_2$–$C_7$ carboxyalkyl group; above-described $C_2$–$C_7$ carboxyalkyloxy group; above-described $C_2$–$C_7$ acyl group; above-described $C_2$–$C_7$ acyloxy group; above-described $C_2$–$C_7$ alkoxycarbonyl group; above-described $C_2$–$C_7$ alkoxycarbonyloxy group; $C_8$–$C_{13}$ aralkyloxycarbonyl group such as benzyloxycarbonyl group, phenylethyloxycarbonyl group, phenylpropyloxycarbonyl group, naphthylmethyloxycarbonyl group, etc.; halogen atoms such as fluorine atom, chlorine atom, bromine atom and the like.

In the compound represented by the above formula (I), it is preferred that the 5- to 6-membered contains 1 to 4 heteroatoms selected from the group consisting of an oxygen atom, a sulfur atom and a nitrogen atom and the total number of atoms constituting the ring is 5 to 10. Further, as the substituent of the respective groups, a group(s) selected from $C_1$–$C_6$ alkyl group, $C_1$–$C_6$ haloalkyl group, $C_1$–$C_6$ alkoxy group, hydroxyl group, carboxyl group, $C_2$–$C_7$ carboxyalkyl group, $C_2$–$C_7$ carboxyalkyloxy group, $C_2$–$C_7$ acyl group, $C_2$–$C_7$ acyloxy group, $C_2$–$C_7$ alkoxycarbonyl group, $C_2$–$C_7$ alkoxycarbonyloxy group, $C_8$–$C_{13}$ aralkyloxycarbonyl group, $C_3$–$C_9$ alkoxycarbonylalkoxy group and halogen atoms is preferred.

In the compound represented by the above formula (I) of the present invention, a carbon atom is preferred as A.

Examples of preferred compounds of the present invention include those of the formula (I), wherein A is a carbon atom; n is 1 or 2; $R^1$ is

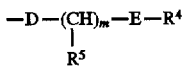

{wherein D and E independently indicate a single bond or an optionally branched $C_1$–$C_6$ alkylene group;

$R^4$ is a $C_1$–$C_6$ alkyl group: —$OR^6$ ($R^6$ is a $C_1$–$C_6$ alkyl group; a $C_6$–$C_{10}$ aryl group which may be substituted with at least one substituent selected from the group consisting of a $C_1$–$C_6$ alkyl group, a $C_1$–$C_6$ alkoxy group, a halogen atom, a hydroxyl group, a carboxyl group, a $C_2$–$C_7$ alkoxycarbonyl group, a $C_2$–$C_7$ carboxyalkyl group, a $C_2$–$C_7$ acyl group, a $C_2$–$C_7$ acyloxy group, a $C_2$–$C_7$ alkoxycarbonyloxy group, a $C_3$–$C_9$ alkoxycarbonylalkoxy group and a benzyloxycarbonyl group; or a $C_7$–$C_{12}$ aralkyl group which may be substituted with at least one substituent selected from the group consisting of a $C_1$–$C_6$ alkyl group, a $C_1$–$C_6$ alkoxy group, a halogen atom, a hydroxyl group, a carboxyl group, a $C_2$–$C_7$ alkoxycarbonyl group, a $C_2$–$C_7$ carboxyalkyl group, a $C_2$–$C_7$ acyl group, a $C_2$–$C_7$ acyloxy group, a $C_2$–$C_7$ alkoxycarbonyloxy group, a $C_3$–$C_9$ alkoxycarbonylalkoxy group and a benzyloxycarbonyl group): —$SR^7$ ($R^7$ is a $C_1$–$C_6$ alkyl group, a $C_6$–$C_{10}$ aryl group which may be substituted with at least one substituent selected from the group consisting of a $C_1$–$C_6$ alkyl group, a $C_1$–$C_6$ alkoxy group, a halogen atom, a hydroxyl group, a carboxyl group, a $C_2$–$C_7$ alkoxycarbonyl group, a $C_2$–$C_7$ carboxyalkyl group, a $C_2$–$C_7$ acyl group, a $C_2$–$C_7$ acyloxy group, a $C_2$–$C_7$ alkoxycarbonyloxy group, a $C_3$–$C_9$ alkoxycarbonylalkoxy group and a benzyloxycarbonyl group; or a $C_7$–$C_{12}$ aralkyl group which may be substituted with at least one substituent selected from the group consisting of a $C_1$–$C_6$ alkyl group, a $C_1$–$C_6$ alkoxy group, a halogen atom, a hydroxyl group, a carboxyl group, a $C_2$–$C_7$ alkoxycarbonyl group, a $C_2$–$C_7$ carboxyalkyl group, a $C_2$–$C_7$ acyl group, a $C_2$–$C_7$ acyloxy group, a $C_2$–$C_7$ alkoxycarbonyloxy group, a $C_3$–$C_9$ alkoxycarbonylalkoxy group and a benzyloxycarbonyl group): —COOH: a $C_6$–$C_{10}$ aryl group which may be substituted with at least one substituent selected from the group consisting of a $C_1$–$C_6$ alkyl group, a $C_1$–$C_6$ alkoxy group, a halogen atom, a hydroxyl group, a carboxyl group, a $C_2$–$C_7$ alkoxycarbonyl group, a $C_2$–$C_7$ carboxyalkyl group, a $C_2$–$C_7$ acyl group, a $C_2$–$C_7$ acyloxy group, a $C_2$–$C_7$ alkoxycarbonyloxy group, a $C_3$–$C_9$ alkoxycarbonylalkoxy group and a benzyloxycarbonyl group: a $C_3$–$C_8$ cycloalkyl group: or —$SiR^{14}R^{15}R^{16}$ ($R^{14}$, $R^{15}$, and $R^{16}$ independently indicate a $C_1$–$C_6$ alkyl group);

$R^5$ is —OH, —$OCOR^{18}$ ($R^{18}$ is a $C_1$–$C_6$ alkoxy group or a $C_2$–$C_7$ alkenylamino group), —$NH_2$, —$NHCOR^{20}$ ($R^{20}$ is a $C1$-$C_6$ alkoxy group, a $C_6$–$C_{10}$ aryloxy group, a $C_3$–$C_9$ alkoxycarbonylalkoxy group, a $C_2$–$C_{12}$ dialkylamino group or a $C_7$–$C_{12}$ aralkyloxy group) or —$NHSO_2R^{21}$ ($R^{21}$ is a $C_1$–$C_6$ alkyl group, a $C_2$–$C_7$ carboxyalkyl group, a $C_6$–C10 aryl group, a $C_3$–$C_9$ alkoxycarbonylalkyl group or a $C_7$–$C_{12}$ aralkyl group); and m is 0 or 1};

$R^2$ is a hydrogen atom; and $R^3$ is —$C(=NR^{25})NH_2$ ($R^{25}$ is a hydrogen atom, a $C_2$–$C_7$ alkoxycarbonyl group or a hydroxyl group), —NH—$C(=NR^{25})NH_2$ ($R^{25}$ is as defined above) or —$NHR^{26}$ ($R^{26}$ is a hydrogen atom, a $C_2$–$C_7$ alkoxycarbonyl group or a 5–$C_1$–$C_3$ alkyl-1,3-dioxol-2-on-4-yl methyl group).

As the more preferred compound of the present invention, there is a compound of the formula (I), wherein A is a carbon atom; n is 1; $R^1$ is

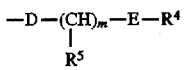

{(wherein D and E independently indicate a single bond or an optionally branched $C_1$–$C_6$ alkylene group;

$R^4$ is a $C_1$–$C_6$ alkyl group; —$OR^6$ ($R^6$ is a $C_6$–$C_{10}$ aryl or $C_7$–$C_{12}$ aralkyl group which may be substituted with at least one substituent selected from the group consisting of a $C_1$–$C_6$ alkyl group, a halogen atom, a carboxyl group, a $C_2$–$C_7$ carboxyalkyl group and a benzyloxycarbonyl group); —$SR^7$ ($R^7$ is a $C_1$–$C_6$ alkyl group); a $C_6$–$C_{10}$ aryl group which may be substituted with at least one substituent selected from the group consisting of a $C_1$–$C_6$ alkyl group, a halogen atom, a carboxyl group, a $C_2$–$C_7$ carboxyalkyl group and a benzyloxycarbonyl group; or a $C_3$–$C_6$ cycloalkyl group;

$R^5$ is —OH, —$NH_2$, —$NHCOR^{20}$ ($R^{20}$ is a $C_1$–$C_6$ alkoxy group or a $C_7$–$C_{12}$ aralkyloxy group) or —$NHSO_2R^{21}$ ($R^{21}$ is a $C_1$–$C_6$ alkyl group or a $C_6$–$C_{10}$aryl group); and m is 1};

$R^2$ is a hydrogen atom; and $R^3$ is —$C(=NR^{25})NH_2$ ($R^{25}$ is a hydrogen atom or a hydroxyl group) or —$NH_2$.

As the more preferred compound of the present invention, there is a compound of the formula (I), wherein A is a carbon atom; n is 1; $R^1$ is

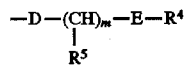

{wherein D is a single bond and E is a single bond or a $C_1$–$C_6$ alkylene group;

$R^4$ is a $C_1$–$C_6$ alkyl group; —$OR^6$ ($R^6$ is a $C_6$–$C_{10}$ aryl or $C_7$–$C_{12}$ aralkyl group which may be substituted with at least one substituent selected from the group consisting of a $C_1$–$C_6$ alkyl group, a halogen atom, a carboxyl group, a $C_2$–$C_7$ carboxyalkyl group and a benzyloxycarbonyl group); —$SR^7$ ($R^7$ is a $C_1$–$C_6$ alkyl group); a $C_6$–$C_{10}$ aryl group which may be substituted with at least one substituent selected from the group consisting of a $C_1$–$C_6$ alkyl group, a halogen atom, a carboxyl group, a $C_2$–$C_7$ carboxyalkyl group and a benzyloxycarbonyl group; or a $C_3$–$C_6$ cycloalkyl group;

$R^5$ is —$NH_2$, —$NHCOR^{20}$ ($R^{20}$ is a $C_1$–$C_6$ alkoxy group or a $C_7$–$C_{12}$ aralkyloxy group) or —$NHSO_2R^{21}$ ($R^{21}$ is a $C_1$–$C_6$ alkyl group or a $C_6$–$C_{10}$ aryl group); and m is 1};

$R^2$ is a hydrogen atom; and $R^3$ is —$C(=NR^{25})NH_2$ ($R^{25}$ is a hydrogen atom or a hydroxyl group) or —$NH_2$.

As the still more preferred compound of the present invention, there is a compound of the formula (I), wherein A is a carbon atom; n is 1; $R^1$ is

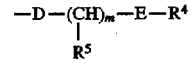

{wherein D is a single bond; E is a single bond or a $C_1$–$C_3$ alkylene group; $R^4$ is a $C_3$–$C_6$ alkyl group, —$OR^6$ ($R^6$ is a $C_1$–$C_6$ alkyl group), a phenyl group or a $C_3$–$C_6$ cycloalkyl group; $R_{20}^5$ is —OH, —NHR$^{19}$ (R$^{19}$ is a hydrogen atom), NHCOR$^{20}$ (R$^{20}$ is a C$_1$–C$_6$ alkoxy group) or —NHSO$_2$R$^{21}$ (R$^{21}$ is a C$_1$–C$_3$ alkyl group); and m is 1};

R$^2$ is a hydrogen atom; and

R$^3$ is —C(=NR$^{25}$)NH$_2$ (R$^{25}$ is a hydrogen atom or a hydroxyl group) or —NH$_2$.

As the particularly preferred compound of the present invention, there is a compound of the formula (I), wherein A is a carbon atom; n is 1; R$^1$ is $$-D-(CH)_m-E-R^4$$
$$\quad\quad\quad\;|$$
$$\quad\quad\quad R^5$$

{wherein D is a single bond; E is a single bond or a C$_1$–C$_6$ alkylene group;

R$^4$ is a C$_1$–C$_6$ alkyl group; R$^5$ is —NHCOR$^{20}$ (R$^{20}$ is a C$_1$–C$_6$ alkoxy group); and m is 1};

R$^2$ is a hydrogen atom; and

R$^3$ is —C(=NR$^{25}$)NH$_2$ (R$^{25}$ is a hydrogen atom or a hydroxyl group)).

As the most preferred compound of the present invention, there is trans-4-[(S)-N-((R)-2-ethoxycarbonylamino-4,4-dimethylpentanoyl) prolyl] aminomethylcyclohexanecarboxamidoxime (compound No. 461 in Table 1 in Example 33).

The prolineamide derivatives represented by the above formula (I) can afford various stereoisomers. For example, concerning asymmetric carbon atoms, the absolute configuration may be D-configuration, L-configuration or DL configuration and all types thereof are included in the compounds of the present invention.

Examples of the salt which can be formed with the compounds of the above formula (I) of the present invention include inorganic acid salts such as hydrochloride, hydrobromide, hydroiodide, sulfate, nitrate, phosphate, etc.; organic acid salts such as succinate, oxalate, fumarate, maleate, lactate, tartrate, citrate, acetate, glycolate, methanesulfonate, toluenesulfonate, etc. Further, the proline derivatives of the above formula (I) containing a free carboxyl group can also form a salt with a pharmaceutically acceptable base.

Examples of the salt include alkaline metal salt, alkaline earth metal salt, ammonium salt, alkyl ammonium salt and the like.

Further, the prolineamide derivatives of the above formula (I) and the salts thereof can also form a hydrate.

Hereinafter, examples of the compounds of the present invention will be described.

TABLE 1

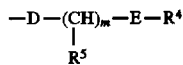

| Compound No. | $-R^1 \begin{pmatrix} -D-(CH)_m-E-R^4 \\ \| \\ R^5 \end{pmatrix}$ | $-R^2$ | $-R^3$ | n | A | Broken line |
|---|---|---|---|---|---|---|
| 1 | —CH$_2$—⟨phenyl⟩ | —H | —C(=NH)NH$_2$ | 1 | C | Single bond |
| 2 | —(CH$_2$)$_2$—⟨phenyl⟩ | —H | —C(=NH)NH$_2$ | 1 | C | Single bond |
| 3 | —(CH$_2$)$_3$—⟨phenyl⟩ | —H | —C(=NH)NH$_2$ | 1 | C | Single bond |
| 4 | —(CH$_2$)$_5$—⟨phenyl⟩ | —H | —C(=NH)NH$_2$ | 1 | C | Single bond |
| 5 | —(CH$_2$)$_8$—⟨phenyl⟩ | —H | —C(=NH)NH$_2$ | 1 | C | Single bond |

TABLE 1-continued

Structure: pyrrolidine with (CH₂)ₙ substituent, N-C(=O)-R¹, and α-carbon bearing -C(=O)-N(R²)-CH₂-[aryl]-A-R³

| Compound No. | -R¹ (-D-(CH)ₘ-E-R⁴ / R⁵) | -R² | -R³ | n | A | Broken line |
|---|---|---|---|---|---|---|
| 6 | -(CH₂)- (1-naphthyl) | -H | -C(=NH)NH₂ | 1 | C | Single bond |
| 7 | -(CH₂)₂-(2-CH₃-phenyl) | -H | -C(=NH)NH₂ | 1 | C | Single bond |
| 8 | -(CH₂)₂-(3-CH₃-phenyl) | -H | -C(=NH)NH₂ | 1 | C | Single bond |
| 9 | -(CH₂)₂-(4-CH₃-phenyl) | -H | -C(=NH)NH₂ | 1 | C | Single bond |
| 10 | -(CH₂)₂-(2-OCH₃-phenyl) | -H | -C(=NH)NH₂ | 1 | C | Single bond |
| 11 | -(CH₂)₂-(3-OCH₃-phenyl) | -H | -C(=NH)NH₂ | 1 | C | Single bond |
| 12 | -(CH₂)₂-(4-OCH₃-phenyl) | -H | -C(=NH)NH₂ | 1 | C | Single bond |
| 13 | -(CH₂)₂-(2-Cl-phenyl) | -H | -C(=NH)NH₂ | 1 | C | Single bond |
| 14 | -(CH₂)₂-(3-Cl-phenyl) | -H | -C(=NH)NH₂ | 1 | C | Single bond |

TABLE 1-continued

Structure: (CH₂)ₘ-pyrrolidine-N(C=O-R¹)-CH(R²)-C(=O)-NCH₂-[ring A]-R³

| Compound No. | -R¹ (-D-(CH)ₘ-E-R⁴ / R⁵) | -R² | -R³ | n | A | Broken line |
|---|---|---|---|---|---|---|
| 15 | -(CH₂)₂-C₆H₄-Cl (4-Cl) | -H | -C(=NH)NH₂ | 1 | C | Single bond |
| 16 | -(CH₂)₂-C₆H₄-F (2-F) | -H | -C(=NH)NH₂ | 1 | C | Single bond |
| 17 | -(CH₂)₂-C₆H₄-F (3-F) | -H | -C(=NH)NH₂ | 1 | C | Single bond |
| 18 | -(CH₂)₂-C₆H₄-F (4-F) | -H | -C(=NH)NH₂ | 1 | C | Single bond |
| 19 | -(CH₂)₂-C₆H₄-CF₃ (2-CF₃) | -H | -C(=NH)NH₂ | 1 | C | Single bond |
| 20 | -(CH₂)₂-C₆H₄-CF₃ (3-CF₃) | -H | -C(=NH)NH₂ | 1 | C | Single bond |
| 21 | -(CH₂)₂-C₆H₄-CF₃ (4-CF₃) | -H | -C(=NH)NH₂ | 1 | C | Single bond |
| 22 | -(CH₂)₂-C₆H₄-OH (2-OH) | -H | -C(=NH)NH₂ | 1 | C | Single bond |
| 23 | -(CH₂)₂-C₆H₄-OH (3-OH) | -H | -C(=NH)NH₂ | 1 | C | Single bond |
| 24 | -(CH₂)₂-C₆H₄-OH (4-OH) | -H | -C(=NH)NH₂ | 1 | C | Single bond |

TABLE 1-continued

Structure: pyrrolidine with (CH₂)ₘ substituent, N-C(=O)-R¹, central carbon with side chain -C(=O)-N(R²)-CH₂-[ring A]-R³

| Compound No. | -R¹ ( -D-C(R⁵)H-(CH)ₘ-E-R⁴ ) | -R² | -R³ | n | A | Broken line |
|---|---|---|---|---|---|---|
| 25 | -(CH₂)₂-[2-COOH-phenyl] | -H | -C(=NH)NH₂ | 1 | C | Single bond |
| 26 | -(CH₂)₂-[3-COOH-phenyl] | -H | -C(=NH)NH₂ | 1 | C | Single bond |
| 27 | -(CH₂)₂-[4-COOH-phenyl] | -H | -C(=NH)NH₂ | 1 | C | Single bond |
| 28 | -(CH₂)₂-[4-CH₂COOH-phenyl] | -H | -C(=NH)NH₂ | 1 | C | Single bond |
| 29 | -(CH₂)₂-[4-OCH₂COOH-phenyl] | -H | -C(=NH)NH₂ | 1 | C | Single bond |
| 30 | -(CH₂)₂-[4-COOCH₃-phenyl] | -H | -C(=NH)NH₂ | 1 | C | Single bond |
| 31 | -(CH₂)₂-[4-COOCH₂-phenyl]-phenyl | -H | -C(=NH)NH₂ | 1 | C | Single bond |
| 32 | -(CH₂)₂-[4-COCH₃-phenyl] | -H | -C(=NH)NH₂ | 1 | C | Single bond |
| 33 | -CH₂-cyclopentyl(H) | -H | -C(=NH)NH₂ | 1 | C | Single bond |
| 34 | -(CH₂)₂-cyclohexyl(H) | -H | -C(=NH)NH₂ | 1 | C | Single bond |
| 35 | -(CH₂)₂-[1,1-(CH₃)₂-cyclohexyl(H)] | -H | -C(=NH)NH₂ | 1 | C | Single bond |

TABLE 1-continued

Structure: (CH₂)ₘ-pyrrolidine with N-C(=O)-R¹, α-carbon bearing -C(=O)N(R²)CH₂-phenyl(A-R³), with broken line in ring.

| Compound No. | -R¹ (-D-(CH)ₘ-E-R⁴ / R⁵) | -R² | -R³ | n | A | Broken line |
|---|---|---|---|---|---|---|
| 36 | -(CH₂)₂-(2-thienyl) | -H | -C(=NH)NH₂ | 1 | C | Single bond |
| 37 | -(CH₂)₂-(2-furyl) | -H | -C(=NH)NH₂ | 1 | C | Single bond |
| 38 | -(CH₂)₂-(1H-pyrrol-2-yl) | -H | -C(=NH)NH₂ | 1 | C | Single bond |
| 39 | -(CH₂)₂-N(CH₂CH₂)₂N-CH₃ | -H | -C(=NH)NH₂ | 1 | C | Single bond |
| 40 | -(CH₂)₂-(1H-indol-3-yl) | -H | -C(=NH)NH₂ | 1 | C | Single bond |
| 41 | -CH₃ | -H | -C(=NH)NH₂ | 1 | C | Single bond |
| 42 | -CH₂CH₃ | -H | -C(=NH)NH₂ | 1 | C | Single bond |
| 43 | -(CH₂)₂CH₃ | -H | -C(=NH)NH₂ | 1 | C | Single bond |
| 44 | -CH(CH₃)₂ | -H | -C(=NH)NH₂ | 1 | C | Single bond |
| 45 | -(CH₂)₃CH₃ | -H | -C(=NH)NH₂ | 1 | C | Single bond |
| 46 | -C(CH₃)₃ | -H | -C(=NH)NH₂ | 1 | C | Single bond |

TABLE 1-continued

| Compound No. | -R¹ ( -D-(CH)ₘ-E-R⁴ with R⁵ ) | -R² | -R³ | n | A | Broken line |
|---|---|---|---|---|---|---|
| 47 | -(CH₂)₄CH₃ | -H | -C(=NH)NH₂ | 1 | C | Single bond |
| 48 | -CH₂CH₂C(CH₃)₃ | -H | -C(=NH)NH₂ | 1 | C | Single bond |
| 49 | -(CH₂)₉CH₃ | -H | -C(=NH)NH₂ | 1 | C | Single bond |
| 50 | -CH₂Si(CH₃)₃ | -H | -C(=NH)NH₂ | 1 | C | Single bond |
| 51 | -CH₂CH₂Si(CH₃)₃ | -H | -C(=NH)NH₂ | 1 | C | Single bond |
| 52 | -CH₂OCH₃ | -H | -C(=NH)NH₂ | 1 | C | Single bond |
| 53 | -CH₂O-C₆H₅ | -H | -C(=NH)NH₂ | 1 | C | Single bond |
| 54 | -CH₂O-C₆H₁₁ | -H | -C(=NH)NH₂ | 1 | C | Single bond |
| 55 | -CH₂CO₂-C₆H₅ | -H | -C(=NH)NH₂ | 1 | C | Single bond |
| 56 | -CH₂OH | -H | -C(=NH)NH₂ | 1 | C | Single bond |
| 57 | -CH₂SCH₃ | -H | -C(=NH)NH₂ | 1 | C | Single bond |
| 58 | -CH₂S-C₆H₅ | -H | -C(=NH)NH₂ | 1 | C | Single bond |

TABLE 1-continued

[Structure shown at top of table with (CH₂)ₙ, N-C(=O)-R¹, CNCH₂-R², and A-R³ groups]

| Compound No. | $-R^1 \left( \begin{array}{c} -D-(CH)_m-E-R^4 \\ R^5 \end{array} \right)$ | $-R^2$ | $-R^3$ | n | A | Broken line |
|---|---|---|---|---|---|---|
| 59 | $-CH_2S-$⟨cyclohexyl-H⟩ | $-H$ | $-C(=NH)NH_2$ | 1 | C | Single bond |
| 60 | $-CH_2SCH_2-$⟨phenyl⟩ | $-H$ | $-C(=NH)NH_2$ | 1 | C | Single bond |
| 61 | $-CH_2SO-$⟨phenyl⟩ | $-H$ | $-C(=NH)NH_2$ | 1 | C | Single bond |
| 62 | $-CH_2SO-$⟨cyclohexyl-H⟩ | $-H$ | $-C(=NH)NH_2$ | 1 | C | Single bond |
| 63 | $-CH_2SO_2-$⟨phenyl⟩ | $-H$ | $-C(=NH)NH_2$ | 1 | C | Single bond |
| 64 | $-CH_2SO_2-$⟨cyclohexyl-H⟩ | $-H$ | $-C(=NH)NH_2$ | 1 | C | Single bond |
| 65 | $-CH_2CO-$⟨phenyl⟩ | $-H$ | $-C(=NH)NH_2$ | 1 | C | Single bond |
| 66 | $-CH_2CO-$⟨cyclohexyl-H⟩ | $-H$ | $-C(=NH)NH_2$ | 1 | C | Single bond |
| 67 | $-CH_2COOH$ | $-H$ | $-C(=NH)NH_2$ | 1 | C | Single bond |
| 68 | $-CH_2COOCH_3$ | $-H$ | $-C(=NH)NH_2$ | 1 | C | Single bond |
| 69 | $-CH_2NHCH_3$ | $-H$ | $-C(=NH)NH_2$ | 1 | C | Single bond |

TABLE 1-continued

| Compound No. | −R¹ ( −D−(CH)ₘ−E−R⁴ / R⁵ ) | −R² | −R³ | n | A | Broken line |
|---|---|---|---|---|---|---|
| 70 | −CH₂NH−C₆H₅ | −H | −C(=NH)NH₂ | 1 | C | Single bond |
| 71 | −CH₂NH−C₆H₁₁ | −H | −C(=NH)NH₂ | 1 | C | Single bond |
| 72 | −CH₂NHCH₂−C₆H₅ | −H | −C(=NH)NH₂ | 1 | C | Single bond |
| 73 | −CH₂NHCOOCH₃ | −H | −C(=NH)NH₂ | 1 | C | Single bond |
| 74 | −CH₂NHCO−C₆H₅ | −H | −C(=NH)NH₂ | 1 | C | Single bond |
| 75 | −CH₂NHCO−C₆H₁₁ | −H | −C(=NH)NH₂ | 1 | C | Single bond |
| 76 | −CH₂NHCOOCH₂−C₆H₅ | −H | −C(=NH)NH₂ | 1 | C | Single bond |
| 77 | −CH₂NHSO₂−(2-thienyl) | −H | −C(=NH)NH₂ | 1 | C | Single bond |
| 78 | −CH₂NHSO₂CH₃ | −H | −C(=NH)NH₂ | 1 | C | Single bond |
| 79 | −CH₂NHSO₂−C₆H₅ | −H | −C(=NH)NH₂ | 1 | C | Single bond |
| 80 | −CH₂NHSO₂CH₂−C₆H₅ | −H | −C(=NH)NH₂ | 1 | C | Single bond |
| 81 | −CH₂NHSO₂−C₆H₁₁ | −H | −C(=NH)NH₂ | 1 | C | Single bond |

TABLE 1-continued

| Compound No. | $-R^1 \left( \begin{array}{c} -D-(CH)_m-E-R^4 \\ R^5 \end{array} \right)$ | $-R^2$ | $-R^3$ | n | A | Broken line |
|---|---|---|---|---|---|---|
| 82 | -CH(cyclohexyl)-OH | -H | -C(=NH)NH₂ | 1 | C | Single bond |
| 83 | -CHCH₂C(CH₃)₃ with OH | -H | -C(=NH)NH₂ | 1 | C | Single bond |
| 84 | -CH(phenyl)-OSi(CH₃)₃ | -H | -C(=NH)NH₂ | 1 | C | Single bond |
| 85 | -CHCH₂C(CH₃)₃ with O-CH₃ | -H | -C(=NH)NH₂ | 1 | C | Single bond |
| 86 | -CHCH₂C(CH₃)₃ with O-tetrahydropyranyl | -H | -C(=NH)NH₂ | 1 | C | Single bond |
| 87 | -CH(cyclohexyl)-OCHO | -H | -C(=NH)NH₂ | 1 | C | Single bond |
| 88 | -CH(phenyl)-OCOCH₃ | -H | -C(=NH)NH₂ | 1 | C | Single bond |
| 89 | -CHCH₂C(CH₃)₃ with OCOOCH₃ | -H | -C(=NH)NH₂ | 1 | C | Single bond |
| 90 | -CH(cyclohexyl)-OCONH₂ | -H | -C(=NH)NH₂ | 1 | C | Single bond |
| 91 | -CH(phenyl)-OCONHCH₃ | -H | -C(=NH)NH₂ | 1 | C | Single bond |

TABLE 1-continued

Structure (header): pyrrolidine ring with $(CH_2)_n$ substitution, N-C(=O)-R¹, with -C(=O)-N(R²)-CH₂- linker to cyclohexyl/phenyl ring bearing A-R³

| Compound No. | -R¹ ( -D-(CH)ₘ-E-R⁴ with R⁵ ) | -R² | -R³ | n | A | Broken line |
|---|---|---|---|---|---|---|
| 92 | -CHCH₂C(CH₃)₃<br>\|<br>OCON(CH₃)₂ | -H | -C(=NH)NH₂ | 1 | C | Single bond |
| 93 | -CH₂CH(cyclohexyl)<br>\|<br>OCONHCH₂CH=CH₂ | -H | -C(=NH)NH₂ | 1 | C | Single bond |
| 94 | -CHCH₂-phenyl<br>\|<br>NHCHO | -H | -C(=NH)NH₂ | 1 | C | Single bond |
| 95 | -CHCH₂C(CH₃)₃<br>\|<br>NHCOCH₃ | -H | -C(=NH)NH₂ | 1 | C | Single bond |
| 96 | -CHCH₂-cyclohexyl<br>\|<br>NHCOCF₃ | -H | -C(=NH)NH₂ | 1 | C | Single bond |
| 97 | -CHCH₂-phenyl<br>\|<br>NHCOOCH₃ | -H | -C(=NH)NH₂ | 1 | C | Single bond |
| 98 | -CHC(SCH₃)(CH₃)₂<br>\|<br>NHCOOC₂H₅ | -H | -C(=NH)NH₂ | 1 | C | Single bond |
| 99 | -CH(cyclohexyl)<br>\|<br>NHCO-phenyl | -H | -C(=NH)NH₂ | 1 | C | Single bond |
| 100 | -CH₂CH(phenyl)<br>\|<br>NHCO-cyclohexyl | -H | -C(=NH)NH₂ | 1 | C | Single bond |
| 101 | -CHCH₂C(CH₃)₃<br>\|<br>NHCOOCH₂-phenyl | -H | -C(=NH)NH₂ | 1 | C | Single bond |

TABLE 1-continued

Structure: (CH₂)ₙ-N(C(=O)R¹)-CH(CNCH₂-R²)-C(=O)- linked to aryl-A-R³

| Compound No. | -R¹ (-D-(CH)ₘ-E-R⁴ / R⁵) | -R² | -R³ | n | A | Broken line |
|---|---|---|---|---|---|---|
| 102 | -CHCH₂-(cyclohexyl-H) / NHCOOCH₂CH=CH₂ | -H | -C(=NH)NH₂ | 1 | C | Single bond |
| 103 | -CHCH₂-(C₆H₄-COOH) / NHCOOCH₂COOH | -H | -C(=NH)NH₂ | 1 | C | Single bond |
| 104 | -CHCH₂C(CH₃)₃ / NHSO₂CH₃ | -H | -C(=NH)NH₂ | 1 | C | Single bond |
| 105 | -CH-(cyclohexyl-H) / NHSO₂CH₃ | -H | -C(=NH)NH₂ | 1 | C | Single bond |
| 106 | -CHCH₂-(cyclohexyl-H) / NHSO₂CH₃ | -H | -C(=NH)NH₂ | 1 | C | Single bond |
| 107 | -CH-(phenyl) / NHSO₂CH₃ | -H | -C(=NH)NH₂ | 1 | C | Single bond |
| 108 | -CHCH₂-(phenyl) / NHSO₂CH₃ | -H | -C(=NH)NH₂ | 1 | C | Single bond |
| 109 | -CH(CH₂)₃CH₃ / NHSO₂CH₃ | -H | -C(=NH)NH₂ | 1 | C | Single bond |
| 110 | -CHCH₂CH₂SCH₃ / NHSO₂CH₃ | -H | -C(=NH)NH₂ | 1 | C | Single bond |
| 111 | -CH₂CH-(phenyl) / NHSO₂CH₃ | -H | -C(=NH)NH₂ | 1 | C | Single bond |
| 112 | -CHCH₂CH(CH₃)₂ / NHSO₂CH₃ | -H | -C(=NH)NH₂ | 1 | C | Single bond |

TABLE 1-continued

| Compound No. | -R¹ (-D-(CH)ₘ-E-R⁴ / R⁵) | -R² | -R³ | n | A | Broken line |
|---|---|---|---|---|---|---|
| 113 | -CHCH(CH₃)₂ / NHSO₂CH₃ | -H | -C(=NH)NH₂ | 1 | C | Single bond |
| 114 | -CHC(CH₃)₃ / NHSO₂CH₃ | -H | -C(=NH)NH₂ | 1 | C | Single bond |
| 115 | -CHCH(CH₃)CH₂CH₃ / NHSO₂CH₃ | -H | -C(=NH)NH₂ | 1 | C | Single bond |
| 116 | -CHCH₂-C₆H₄-F / NHSO₂CH₃ | -H | -C(=NH)NH₂ | 1 | C | Single bond |
| 117 | -CH(CH₂)₄COOEt / NHSO₂Me | -H | -C(=NH)NH₂ | 1 | C | Single bond |
| 118 | -CH(CH₂)₂-C₆H₄-COOCH₂-C₆H₅ / NHSO₂CH₃ | -H | -C(=NH)NH₂ | 1 | C | Single bond |
| 119 | -CH(CH₂)₂-C₆H₄-COOH / NHSO₂CH₃ | -H | -C(=NH)NH₂ | 1 | C | Single bond |
| 120 | -CH(CH₂)₂-C₆H₄-COOH / NHSO₂CH₃ | -H | -C(=NH)NH₂ | 1 | C | Single bond |
| 121 | -CHCH₂O-C₆H₄-COOCH₂-C₆H₅ / NHSO₂CH₃ | -H | -C(=NH)NH₂ | 1 | C | Single bond |
| 122 | -CHCH₂O-C₆H₄-COOH / NHSO₂CH₃ | -H | -C(=NH)NH₂ | 1 | C | Single bond |

TABLE 1-continued

[Structure: (CH₂)ₙ-pyrrolidine-N-C(=O)-R¹, with C(=O)-N(R²)-CH₂-phenyl-A-R³]

| Compound No. | -R¹ ( -D-(CH)ₘ-E-R⁴ / R⁵ ) | -R² | -R³ | n | A | Broken line |
|---|---|---|---|---|---|---|
| 123 | -CHCH₂O-(2-COOCH₂Ph-phenyl) / NHSO₂CH₃ | -H | -C(=NH)NH₂ | 1 | C | Single bond |
| 124 | -CHCH₂O-(2-COOH-phenyl) / NHSO₂CH₃ | -H | -C(=NH)NH₂ | 1 | C | Single bond |
| 125 | -CHCH₂CH₂-(3-CH₃-phenyl) / NHSO₂CH₃ | -H | -C(=NH)NH₂ | 1 | C | Single bond |
| 126 | -CHCH₂-(4-Cl-phenyl) / NHSO₂CH₃ | -H | -C(=NH)NH₂ | 1 | C | Single bond |
| 127 | -CHCH₂CH₂-(4-COOCH₃-phenyl) / NHSO₂CH₃ | -H | -C(=NH)NH₂ | 1 | C | Single bond |
| 128 | -CHCH₂-(2-COOH-phenyl) / NHSO₂CH₃ | -H | -C(=NH)NH₂ | 1 | C | Single bond |
| 129 | -CHCH₂O-(4-CH₃-phenyl) / NHSO₂CH₃ | -H | -C(=NH)NH₂ | 1 | C | Single bond |
| 130 | -CHCH₂O-(3-COOH-phenyl) / NHSO₂CH₃ | -H | -C(=NH)NH₂ | 1 | C | Single bond |
| 131 | -CHCH₂O-(3-COOCH₂Ph-phenyl) / NHSO₂CH₃ | -H | -C(=NH)NH₂ | 1 | C | Single bond |

TABLE 1-continued
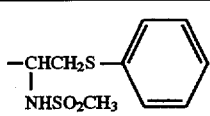
| Compound No. | $-R^1 \left( \begin{array}{c} -D-(CH)_m-E-R^4 \\ | \\ R^5 \end{array} \right)$ | $-R^2$ | $-R^3$ | n | A | Broken line |
|---|---|---|---|---|---|---|
| 132 | 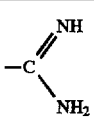 | —H | 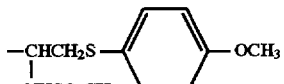 | 1 | C | Single bond |
| 133 |  | —H | 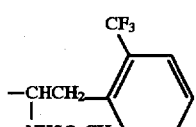 | 1 | C | Single bond |
| 134 | 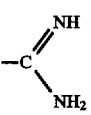 | —H | 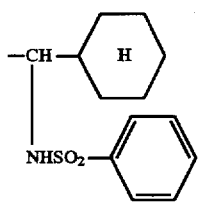 | 1 | C | Single bond |
| 135 | 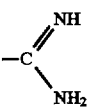 | —H | 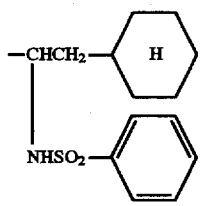 | 1 | C | Single bond |
| 136 | 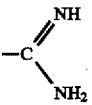 | —H | 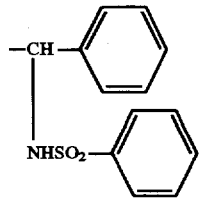 | 1 | C | Single bond |
| 137 | 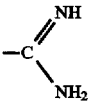 | —H | 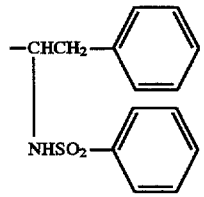 | 1 | C | Single bond |
| 138 | 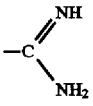 | —H | | 1 | C | Single bond |

TABLE 1-continued

| Compound No. | -R¹ (-D-(CH)ₘ-E-R⁴ with R⁵) | -R² | -R³ | n | A | Broken line |
|---|---|---|---|---|---|---|
| 139 | -CHCH₂-(C₆H₄)-CH₃ with NHSO₂-C₆H₅ | -H | -C(=NH)NH₂ | 1 | C | Single bond |
| 140 | -CHCH₂-(C₆H₄)-OH with NHSO₂-C₆H₅ | -H | -C(=NH)NH₂ | 1 | C | Single bond |
| 141 | -CHCH₂-(C₆H₄)-COOH with NHSO₂-C₆H₅ | -H | -C(=NH)NH₂ | 1 | C | Single bond |
| 142 | -CHCH₂C(CH₃)₃ with NHSO₂-C₆H₅ | -H | -C(=NH)NH₂ | 1 | C | Single bond |
| 143 | -CHCH₂OCH₃ with NHSO₂-C₆H₅ | -H | -C(=NH)NH₂ | 1 | C | Single bond |
| 144 | -CHCH₂O-C₆H₅ with NHSO₂-C₆H₅ | -H | -C(=NH)NH₂ | 1 | C | Single bond |
| 145 | -CHCH₂O-(C₆H₄)-COOH with NHSO₂-C₆H₅ | -H | -C(=NH)NH₂ | 1 | C | Single bond |

TABLE 1-continued

| Compound No. | -R¹ ( -D-(CH)ₘ-E-R⁴ / R⁵ ) | -R² | -R³ | n | A | Broken line |
|---|---|---|---|---|---|---|
| 146 | -CHCH₂SCH₃ / NHSO₂-Ph | -H | -C(=NH)NH₂ | 1 | C | Single bond |
| 147 | -CHCH₂S-Ph / NHSO₂-Ph | -H | -C(=NH)NH₂ | 1 | C | Single bond |
| 148 | -CHCH₂-Cyclohexyl / NHSO₂CH₂COOH | -H | -C(=NH)NH₂ | 1 | C | Single bond |
| 149 | -CHCH₂-Ph / NHSO₂CH₂COOH | -H | -C(=NH)NH₂ | 1 | C | Single bond |
| 150 | -CHCH₂-C₆H₄-OH / NHSO₂CH₂COOH | -H | -C(=NH)NH₂ | 1 | C | Single bond |
| 151 | -CHCH₂C(CH₃)₃ / NHSO₂CH₂COOH | -H | -C(=NH)NH₂ | 1 | C | Single bond |
| 152 | -CH(CH₂)₄CH₃ / NHSO₂CH₂COOH | -H | -C(=NH)NH₂ | 1 | C | Single bond |
| 153 | -CHCH₂O-Ph / NHSO₂CH₂COOH | -H | -C(=NH)NH₂ | 1 | C | Single bond |
| 154 | -CHCH₂O-Cyclohexyl / NHSO₂CH₂COOH | -H | -C(=NH)NH₂ | 1 | C | Single bond |
| 155 | -CHCH₂S-Ph / NHSO₂CH₂COOH | -H | -C(=NH)NH₂ | 1 | C | Single bond |

TABLE 1-continued

| Compound No. | $-R^1 \left( \begin{array}{c} -D-(CH)_m-E-R^4 \\ R^5 \end{array} \right)$ | $-R^2$ | $-R^3$ | n | A | Broken line |
|---|---|---|---|---|---|---|
| 156 | -CHCH$_2$S-C$_6$H$_{11}$ (cyclohexyl, H); NHSO$_2$CH$_2$COOH | -H | -C(=NH)NH$_2$ | 1 | C | Single bond |
| 157 | -CHCH$_2$-C$_6$H$_{11}$ (cyclohexyl, H); NHSO$_2$CF$_3$ | -H | -C(=NH)NH$_2$ | 1 | C | Single bond |
| 158 | -CHCH$_2$-phenyl; NHSO$_2$CF$_3$ | -H | -C(=NH)NH$_2$ | 1 | C | Single bond |
| 159 | -CHCH$_2$-(2-CF$_3$-phenyl); NHSO$_2$CF$_3$ | -H | -C(=NH)NH$_2$ | 1 | C | Single bond |
| 160 | -CHCH$_2$-(3-OCH$_3$-phenyl); NHSO$_2$CF$_3$ | -H | -C(=NH)NH$_2$ | 1 | C | Single bond |
| 161 | -CHCH$_2$-(4-F-phenyl); NHSO$_2$CF$_3$ | -H | -C(=NH)NH$_2$ | 1 | C | Single bond |
| 162 | -CHCH$_2$-(2-COOH-phenyl); NHSO$_2$CF$_3$ | -H | -C(=NH)NH$_2$ | 1 | C | Single bond |
| 163 | -CHCH$_2$-(3-OH-phenyl); NHSO$_2$CF$_3$ | -H | -C(=NH)NH$_2$ | 1 | C | Single bond |
| 164 | -CH$_2$CH(CH$_2$)$_3$CH$_3$; NHSO$_2$CF$_3$ | -H | -C(=NH)NH$_2$ | 1 | C | Single bond |
| 165 | -CHCH$_2$C(CH$_3$)$_3$; NHSO$_2$CF$_3$ | -H | -C(=NH)NH$_2$ | 1 | C | Single bond |

TABLE 1-continued

Structure at top of table:
$(CH_2)_n$ group attached to pyrrolidine ring with N-C(=O)-R¹ substituent; the ring carbon bears -C(=O)-N(R²)-CH₂- connected to a phenyl ring (with dashed bond) bearing A-R³.

| Compound No. | -R¹ $\left(-D-(CH)_m-E-R^4 \atop R^5\right)$ | -R² | -R³ | n | A | Broken line |
|---|---|---|---|---|---|---|
| 166 | -CHCH₂O-(phenyl)<br>\|<br>NHSO₂CF₃ | -H | -C(=NH)NH₂ | 1 | C | Single bond |
| 167 | -CHCH₂S-(phenyl)<br>\|<br>NHSO₂CF₃ | -H | -C(=NH)NH₂ | 1 | C | Single bond |
| 168 | -CHCH₂-(cyclohexyl-H)<br>\|<br>NHSO₂CH₂-(phenyl) | -H | -C(=NH)NH₂ | 1 | C | Single bond |
| 169 | -CHCH₂-(phenyl)<br>\|<br>NHSO₂CH₂-(phenyl) | -H | -C(=NH)NH₂ | 1 | C | Single bond |
| 170 | -CHCH₂C(CH₃)₃<br>\|<br>NHSO₂CH₂-(phenyl) | -H | -C(=NH)NH₂ | 1 | C | Single bond |
| 171 | -CHCH₂O-(cyclohexyl-H)<br>\|<br>NHSO₂CH₂-(phenyl) | -H | -C(=NH)NH₂ | 1 | C | Single bond |
| 172 | -CHCH₂S-(cyclohexyl-H)<br>\|<br>NHSO₂CH₂-(phenyl) | -H | -C(=NH)NH₂ | 1 | C | Single bond |
| 173 | -CHCH₂-(cyclohexyl-H)<br>\|<br>NH₂ | -H | -C(=NH)NH₂ | 1 | C | Single bond |

TABLE 1-continued

Structure:
(CH₂)ₘ on pyrrolidine ring; N-C(=O)-R¹; α-carbon bears -C(O)-N(R²)-CH₂-[aryl]-A-R³

| Compound No. | -R¹ (-D-(CH)ₘ-E-R⁴ / R⁵) | -R² | -R³ | n | A | Broken line |
|---|---|---|---|---|---|---|
| 174 | -CHCH₂-C₆H₅ \| NH₂ | -H | -C(=NH)NH₂ | 1 | C | Single bond |
| 175 | -CHCH₂-(C₆H₄-COOCH₃) \| NH₂ | -H | -C(=NH)NH₂ | 1 | C | Single bond |
| 176 | -CHCH₂-(C₆H₄-CH₂COOH) \| NH₂ | -H | -C(=NH)NH₂ | 1 | C | Single bond |
| 177 | -CHCH₂-(C₆H₄-CH₂COOH) \| NH₂ | -H | -C(=NH)NH₂ | 1 | C | Single bond |
| 178 | -CHCH₂-(C₆H₄-COOH) \| NH₂ | -H | -C(=NH)NH₂ | 1 | C | Single bond |
| 179 | -CHCH(CH₂)₄CH₃ \| NH₂ | -H | -C(=NH)NH₂ | 1 | C | Single bond |
| 180 | -CHCH₂C(CH₃)₃ \| NH₂ | -H | -C(=NH)NH₂ | 1 | C | Single bond |
| 181 | -CHCH₂O-C₆H₅ \| NH₂ | -H | -C(=NH)NH₂ | 1 | C | Single bond |
| 182 | -CHCH₂O-(C₆H₄-OH) \| NH₂ | -H | -C(=NH)NH₂ | 1 | C | Single bond |
| 183 | -CHCH₂O-(cyclohexyl, H) \| NH₂ | -H | -C(=NH)NH₂ | 1 | C | Single bond |
| 184 | -CHCH₂S-C₆H₅ \| NH₂ | -H | -C(=NH)NH₂ | 1 | C | Single bond |

TABLE 1-continued

| Compound No. | —R¹ (—D—(CH)ₘ—E—R⁴ with R⁵) | —R² | —R³ | n | A | Broken line |
|---|---|---|---|---|---|---|
| 185 | —CHCH₂S—(3-Cl-phenyl), NH₂ | —H | —C(=NH)NH₂ | 1 | C | Single bond |
| 186 | —CHCH₂S—(cyclohexyl), NH₂ | —H | —C(=NH)NH₂ | 1 | C | Single bond |
| 187 | —CH—(cyclohexyl), NHCH₃ | —H | —C(=NH)NH₂ | 1 | C | Single bond |
| 188 | —CHCH₂—(cyclohexyl), NHC₂H₅ | —H | —C(=NH)NH₂ | 1 | C | Single bond |
| 189 | —CHCH₂—(phenyl), NHCH₃ | —H | —C(=NH)NH₂ | 1 | C | Single bond |
| 190 | —CHCH₂—(phenyl-OCH₂COOH), NHCH₃ | —H | —C(=NH)NH₂ | 1 | C | Single bond |
| 191 | —CHCH₂—(phenyl-COOH), NHCH₃ | —H | —C(=NH)NH₂ | 1 | C | Single bond |
| 192 | —CHCH₂C(CH₃)₃, NHCH₃ | —H | —C(=NH)NH₂ | 1 | C | Single bond |
| 193 | —CHCH₂O—(phenyl), NHCH₃ | —H | —C(=NH)NH₂ | 1 | C | Single bond |
| 194 | —CHCH₂S—(cyclohexyl), NHCH₃ | —H | —C(=NH)NH₂ | 1 | C | Single bond |

TABLE 1-continued

| Compound No. | $-R^1 \left( \begin{array}{c} -D-(CH)_m-E-R^4 \\ R^5 \end{array} \right)$ | $-R^2$ | $-R^3$ | n | A | Broken line |
|---|---|---|---|---|---|---|
| 195 | -CHCH₂-(C₆H₁₁), NHCH₂-(C₆H₅) | -H | -C(=NH)NH₂ | 1 | C | Single bond |
| 196 | -CHCH₂-(C₆H₅), NHCH₂-(C₆H₅) | -H | -C(=NH)NH₂ | 1 | C | Single bond |
| 197 | -CH₂CH(CH₂)₃CH₃, NHCH₂-(C₆H₅) | -H | -C(=NH)NH₂ | 1 | C | Single bond |
| 198 | -CHCH₂C(CH₃)₃, NHCH₂-(C₆H₅) | -H | -C(=NH)NH₂ | 1 | C | Single bond |
| 199 | -CHCH₂OCH₂H₅, NHCH₂-(C₆H₅) | -H | -C(=NH)NH₂ | 1 | C | Single bond |
| 200 | -CHCH₂SCH₃, NHCH₂-(C₆H₅) | -H | -C(=NH)NH₂ | 1 | C | Single bond |
| 201 | -(C₆H₅) | -H | -C(=NH)NH₂ | 1 | C | — |
| 202 | -CH₂-(C₆H₅) | -H | -C(=NH)NH₂ | 1 | C | — |
| 203 | -CH₂-(C₆H₁₁) | -H | -C(=NH)NH₂ | 1 | C | — |

TABLE 1-continued

| Compound No. | -R¹ ( -D-(CH)ₘ-E-R⁴ / R⁵ ) | -R² | -R³ | n | A | Broken line |
|---|---|---|---|---|---|---|
| 204 | -(CH₂)₂CH₃ | -H | -C(=NH)NH₂ | 1 | C | — |
| 205 | -CH₂O-C₆H₅ | -H | -C(=NH)NH₂ | 1 | C | — |
| 206 | -CH₂O-C₆H₄-CH₃ (o) | -H | -C(=NH)NH₂ | 1 | C | — |
| 207 | -CH₂O-C₆H₄-OCH₃ | -H | -C(=NH)NH₂ | 1 | C | — |
| 208 | -CH₂O-C₆H₄-Cl | -H | -C(=NH)NH₂ | 1 | C | — |
| 209 | -CH₂O-C₆H₄-CF₃ | -H | -C(=NH)NH₂ | 1 | C | — |
| 210 | -CH₂O-C₆H₄-OH | -H | -C(=NH)NH₂ | 1 | C | — |
| 211 | -CH₂O-C₆H₄-CH₂COOH | -H | -C(=NH)NH₂ | 1 | C | — |
| 212 | -CH₂O-C₆H₄-OCH₂COOH | -H | -C(=NH)NH₂ | 1 | C | — |
| 213 | -CH₂O-C₆H₄-COOH | -H | -C(=NH)NH₂ | 1 | C | — |

TABLE 1-continued

| Compound No. | $-R^1 \left( \begin{array}{c} -D-(CH)_m-E-R^4 \\ R^5 \end{array} \right)$ | $-R^2$ | $-R^3$ | n | A | Broken line |
|---|---|---|---|---|---|---|
| 214 | $-CH_2O-\langle C_6H_4\rangle-COOCH_3$ | $-H$ | $-C(=NH)NH_2$ | 1 | C | — |
| 215 | $-CH_2O-\langle C_6H_4\rangle-COOCH_2-\langle C_6H_5\rangle$ (ortho) | $-H$ | $-C(=NH)NH_2$ | 1 | C | — |
| 216 | $-CH_2O-\langle C_6H_4\rangle-COCH_3$ | $-H$ | $-C(=NH)NH_2$ | 1 | C | — |
| 217 | $-CH_2S-\langle C_6H_5\rangle$ | $-H$ | $-C(=NH)NH_2$ | 1 | C | — |
| 218 | $-CH_2S-\langle C_6H_4\rangle-OH$ | $-H$ | $-C(=NH)NH_2$ | 1 | C | — |
| 219 | $-CH_2S-\langle C_6H_4\rangle-COOH$ | $-H$ | $-C(=NH)NH_2$ | 1 | C | — |
| 220 | $-CH_2S-\langle C_6H_4\rangle-COCH_3$ | $-H$ | $-C(=NH)NH_2$ | 1 | C | — |
| 221 | $-CH(OH)-\langle C_6H_{11}\rangle$ | $-H$ | $-C(=NH)NH_2$ | 1 | C | — |
| 222 | $-CH(OCOCH_3)CH_2-\langle C_6H_{11}\rangle$ | $-H$ | $-C(=NH)NH_2$ | 1 | C | — |
| 223 | $-CH(OCOC_2H_5)CH_2-\langle C_6H_{11}\rangle$ | $-H$ | $-C(=NH)NH_2$ | 1 | C | — |
| 224 | $-CH(OCOOCH_3)CH_2-\langle C_6H_{11}\rangle$ | $-H$ | $-C(=NH)NH_2$ | 1 | C | — |

TABLE 1-continued

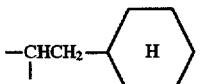

| Compound No. | -R¹ ( -D-(CH)ₘ-E-R⁴ / R⁵ ) | -R² | -R³ | n | A | Broken line |
|---|---|---|---|---|---|---|
| 225 | -CHCH₂-⟨H⟩ <br> \| <br> NHCHO | -H | -C(=NH)NH₂ | 1 | C | — |
| 226 | -CHCH₂-⟨H⟩ <br> \| <br> NHCOOCH₃ | -H | -C(=NH)NH₂ | 1 | C | — |
| 227 | -CHCH₂-⟨H⟩ <br> \| <br> NHCOOC₂H₅ | -H | -C(=NH)NH₂ | 1 | C | — |
| 228 | -CH-⟨H⟩ <br> \| <br> NHCOOCH(CH₃)₂ | -H | -C(=NH)NH₂ | 1 | C | — |
| 229 | -CHCH₂-⟨H⟩ <br> \| <br> NHCOOCH₂-⟨Ph⟩ | -H | -C(=NH)NH₂ | 1 | C | — |
| 230 | -CHCH₂-⟨H⟩ <br> \| <br> NHSO₂CH₃ | -H | -C(=NH)NH₂ | 1 | C | — |
| 231 | -CHCH₂-⟨H⟩ <br> \| <br> NHSO₂C₂H₅ | -H | -C(=NH)NH₂ | 1 | C | — |
| 232 | -CHCH₂-⟨H⟩ <br> \| <br> NHSO₂-⟨Ph⟩ | -H | -C(=NH)NH₂ | 1 | C | — |
| 233 | -CHCH₂-⟨H⟩ <br> \| <br> NHSO₂COOH | -H | -C(=NH)NH₂ | 1 | C | — |

TABLE 1-continued

[Structure: pyrrolidine with (CH₂)ₘ, N-C(=O)-R¹, and C(=O)N(R²)CH₂-aryl-A-R³]

| Compound No. | -R¹ ( -D-(CH)ₘ-E-R⁴ with R⁵ ) | -R² | -R³ | n | A | Broken line |
|---|---|---|---|---|---|---|
| 234 | -CHCH₂-cyclohexyl, with NH₂ (H on ring) | -H | -C(=NH)NH₂ | 1 | C | — |
| 235 | -CH(OH)-phenyl | -H | -C(=NH)NH₂ | 1 | C | — |
| 236 | -CH(OH)CH₂-C₆H₄-OH (para) | -H | -C(=NH)NH₂ | 1 | C | — |
| 237 | -CH(NHSO₂CH₃)-phenyl | -H | -C(=NH)NH₂ | 1 | C | — |
| 238 | -CH(NHCOOC₂H₅)-phenyl | -H | -C(=NH)NH₂ | 1 | C | — |
| 239 | -CH(NHSO₂CH₃)CH₂C(CH₃)₃ | -H | -C(=NH)NH₂ | 1 | C | — |
| 240 | -CH(NHCOOC₂H₅)CH₂OC(CH₃)₃ | -H | -C(=NH)NH₂ | 1 | C | — |
| 241 | -CH(NHSO₂CH₃)CH(CH₃)₂ | -H | -C(=NH)NH₂ | 1 | C | — |
| 242 | -CH(NHCOOC₂H₅)CH(CH₃)₂ | -H | -C(=NH)NH₂ | 1 | C | — |
| 243 | -CH(NHSO₂CH₃)C(CH₃)₃ | -H | -C(=NH)NH₂ | 1 | C | — |
| 244 | -CH(NHCOOC₂H₅)C(CH₃)₃ | -H | -C(=NH)NH₂ | 1 | C | — |

TABLE 1-continued

| Compound No. | $-R^1 \left( \begin{array}{c} -D-(CH)_m-E-R^4 \\ R^5 \end{array} \right)$ | $-R^2$ | $-R^3$ | n | A | Broken line |
|---|---|---|---|---|---|---|
| 245 | -CH(CH₂)₃CH₃<br>\|<br>NHSO₂CH₃ | -H | -C(=NH)NH₂ | 1 | C | — |
| 246 | -CHCH₂CH₂SCH₃<br>\|<br>NHSO₂CH₃ | -H | -C(=NH)NH₂ | 1 | C | — |
| 247 | -CHCH₂-Ph<br>\|<br>OCOCH₃ | -H | -C(=NH)NH₂ | 1 | C | — |
| 248 | -CHCH₂-Ph<br>\|<br>OCOOC₂H₅ | -H | -C(=NH)NH₂ | 1 | C | — |
| 249 | -CHCH₂-C₆H₄-COOH<br>\|<br>OCOOC₂H₅ | -H | -C(=NH)NH₂ | 1 | C | — |
| 250 | -CHCH₂-Ph<br>\|<br>NHSO₂CH₃ | -H | -C(=NH)NH₂ | 1 | C | — |
| 251 | -CHCH₂CH₂-C₆H₄-COOCH₃<br>\|<br>NHSO₂CH₃ | -H | -C(=NH)NH₂ | 1 | C | — |
| 252 | -CHCH₂-Ph<br>\|<br>NHSO₂-Ph | -H | -C(=NH)NH₂ | 1 | C | — |
| 253 | -CHCH₂-Ph<br>\|<br>NHSO₂CH₂COOH | -H | -C(=NH)NH₂ | 1 | C | — |
| 254 | -CH₂CH-Ph<br>\|<br>NHCHO | -H | -C(=NH)NH₂ | 1 | C | — |

TABLE 1-continued

Structure: pyrrolidine with (CH₂)ₘ, N-C(=O)-R¹, α-carbon with C(=O)-N(R²)-CH₂-phenyl-A-R³

| Compound No. | -R¹ ( -D-(CH)ₘ-E-R⁴ / R⁵ ) | -R² | -R³ | n | A | Broken line |
|---|---|---|---|---|---|---|
| 255 | -CHCH₂-(4-F-C₆H₄)<br>\|<br>NHCOOC₂H₅ | -H | -C(=NH)NH₂ | 1 | C | — |
| 256 | -CHCH₂-(2-CH₃-C₆H₄)<br>\|<br>NHCOOCH₂-C₆H₅ | -H | -C(=NH)NH₂ | 1 | C | — |
| 257 | -CHCH₂-C₆H₅<br>\|<br>NH₂ | -H | -C(=NH)NH₂ | 1 | C | — |
| 258 | -CHCH₂C(CH₃)₃<br>\|<br>OH | -H | -C(=NH)NH₂ | 1 | C | — |
| 259 | -CH(CH₂)₄CH₃<br>\|<br>OCOCH₃ | -H | -C(=NH)NH₂ | 1 | C | — |
| 260 | -CHC(SCH₃)(CH₃)₂<br>\|<br>OCOOC₂H₅ | -H | -C(=NH)NH₂ | 1 | C | — |
| 261 | -CHCH₂C(CH₃)₃<br>\|<br>OCONHCH₂CH=CH₂ | -H | -C(=NH)NH₂ | 1 | C | — |
| 262 | -CH(CH₂)₃CH₃<br>\|<br>NHCOOCH₃ | -H | -C(=NH)NH₂ | 1 | C | — |
| 263 | -CHCH₂C(CH₃)₃<br>\|<br>NHCOOC₂H₅ | -H | -C(=NH)NH₂ | 1 | C | — |
| 264 | -CHCH₂CH(C₂H₅)₂<br>\|<br>NHCOOC₂H₅ | -H | -C(=NH)NH₂ | 1 | C | — |

TABLE 1-continued

| Compound No. | −R¹ (−D−(CH)ₘ−E−R⁴ / R⁵) | −R² | −R³ | n | A | Broken line |
|---|---|---|---|---|---|---|
| 265 | −CHCH₂C(CH₃)₃ \| NHCOOCH(CH₃)₂ | −H | −C(=NH)NH₂ | 1 | C | — |
| 266 | −CHCH₂C(CH₃)₃ \| NHCOOC(CH₃)₃ | −H | −C(=NH)NH₂ | 1 | C | — |
| 267 | −CH(CH₂)₄CH₃ \| NHCOOCH₂−Ph | −H | −C(=NH)NH₂ | 1 | C | — |
| 268 | −CH₂CH(CH₂)₂CH₃ \| NHSO₂CH₃ | −H | −C(=NH)NH₂ | 1 | C | — |
| 269 | −CHCH₂CH(CH₃)₂ \| NHSO₂CH₃ | −H | −C(=NH)NH₂ | 1 | C | — |
| 270 | −CHCH₂C(CH₃)₃ \| NHSO₂−Ph | −H | −C(=NH)NH₂ | 1 | C | — |
| 271 | −CH₂CH(CH₂)₂CH₃ \| NH₂ | −H | −C(=NH)NH₂ | 1 | C | — |
| 272 | −(CH₂)₂−Ph | −H | −C(=NH)NH₂ | 1 | N | — |
| 273 | −CH₂OCH₂−Ph | −H | −C(=NH)NH₂ | 1 | N | — |
| 274 | −CH(−Ph) \| NHSO₂CH₃ | −H | −C(=NH)NH₂ | 1 | N | — |
| 275 | −CHCH₂−Ph \| NHCHO | −H | −C(=NH)NH₂ | 1 | N | — |

TABLE 1-continued

Structure:
(CH₂)ₘ-pyrrolidine with N-C(=O)-R¹, α-carbon bearing -C(=O)N(R²)CH₂-[phenyl/cyclohexyl ring]-A-R³

| Compound No. | -R¹ (-D-(CH₂)ₘ-E-R⁴ / R⁵) | -R² | -R³ | n | A | Broken line |
|---|---|---|---|---|---|---|
| 276 | -CHCH₂-C₆H₅ / NHSO₂CH₃ | -H | -C(=NH)NH₂ | 1 | N | — |
| 277 | -CHCH₂-C₆H₅ / NHCOOC₂H₅ | -H | -C(=NH)NH₂ | 1 | N | — |
| 278 | -CHCH₂-C₆H₅ / NH₂ | -H | -C(=NH)NH₂ | 1 | N | — |
| 279 | -CH₂CH-C₆H₅ / NHSO₂CH₃ | -H | -C(=NH)NH₂ | 1 | N | — |
| 280 | -CHCH₂-C₆H₅ / OCOOC₂H₅ | -H | -C(=NH)NH₂ | 1 | N | — |
| 281 | -CHCH₂-C₆H₅ / OCONHCH₂CH=CH₂ | -H | -C(=NH)NH₂ | 1 | N | — |
| 282 | -CH-C₆H₅ / OH | -H | -C(=NH)NH₂ | 1 | N | — |
| 283 | -CH-C₆H₁₁ / NHSO₂CH₃ | -H | -C(=NH)NH₂ | 1 | N | — |
| 284 | -CHCH₂-C₆H₁₁ / NHSO₂CH₃ | -H | -C(=NH)NH₂ | 1 | N | — |
| 285 | -CHCH₂-C₆H₁₁ / NHCOOC₂H₅ | -H | -C(=NH)NH₂ | 1 | N | — |
| 286 | -CH-C₆H₁₁ / NHCOOCH(CH₃)₂ | -H | -C(=NH)NH₂ | 1 | N | — |

TABLE 1-continued

Structure header:

$$\text{Structure: pyrrolidine with (CH}_2)_n\text{, N-C(=O)-R}^1\text{, CH(R}^2\text{)-C(=O)-NCH}_2\text{-phenyl-A-R}^3$$

| Compound No. | $-R^1\left(\begin{array}{c}-D-(CH)_m-E-R^4\\|\\R^5\end{array}\right)$ | $-R^2$ | $-R^3$ | n | A | Broken line |
|---|---|---|---|---|---|---|
| 287 | -CH(NHCOOC(CH$_3$)$_3$)-C$_6$H$_{11}$ | -H | -C(=NH)NH$_2$ | 1 | N | — |
| 288 | -CHCH$_2$(NHCOOC(CH$_3$)$_3$)-C$_6$H$_{11}$ | -H | -C(=NH)NH$_2$ | 1 | N | — |
| 289 | -CH(NHCOOCH(CH$_3$)$_2$)-C$_5$H$_9$ | -H | -C(=NH)NH$_2$ | 1 | N | — |
| 290 | -CH(OH)-C$_6$H$_{11}$ | -H | -C(=NH)NH$_2$ | 1 | N | — |
| 291 | -CHCH$_2$C(CH$_3$)$_3$<br>\|<br>NHSO$_2$CH$_3$ | -H | -C(=NH)NH$_2$ | 1 | N | — |
| 292 | -CH(CH$_2$)$_2$SCH$_3$<br>\|<br>NHSO$_2$CH$_3$ | -H | -C(=NH)NH$_2$ | 1 | N | — |
| 293 | -CH(CH$_2$)$_3$CH$_3$<br>\|<br>NHSO$_2$CH$_3$ | -H | -C(=NH)NH$_2$ | 1 | N | — |
| 294 | -CHC(SCH$_3$)(CH$_3$)$_2$<br>\|<br>NHCOOC$_2$H$_5$ | -H | -C(=NH)NH$_2$ | 1 | N | — |
| 295 | -CH(CH$_2$)$_4$CH$_3$<br>\|<br>NHSO$_2$CH$_2$COOH | -H | -C(=NH)NH$_2$ | 1 | N | — |
| 296 | -CHCH$_2$C(CH$_3$)$_3$<br>\|<br>NHCOOC$_2$H$_5$ | -H | -C(=NH)NH$_2$ | 1 | N | — |
| 297 | -CHCH$_2$C(CH$_3$)$_3$<br>\|<br>NHCOOCH(CH$_3$)$_2$ | -H | -C(=NH)NH$_2$ | 1 | N | — |

TABLE 1-continued

| Compound No. | $-R^1 \left( \begin{array}{c} -D-(CH)_m-E-R^4 \\ R^5 \end{array} \right)$ | $-R^2$ | $-R^3$ | n | A | Broken line |
|---|---|---|---|---|---|---|
| 298 | —CHCH$_2$CH(C$_2$H$_5$)$_2$<br>\|<br>NHCOOC$_2$H$_5$ | —H | —C(=NH)NH$_2$ | 1 | N | — |
| 299 | —CHCH$_2$C(CH$_3$)$_3$<br>\|<br>NHCOOC(CH$_3$)$_3$ | —H | —C(=NH)NH$_2$ | 1 | N | — |
| 300 | —CHCH$_2$C(CH$_3$)$_3$<br>\|<br>NHCOOCH$_2$C$_6$H$_5$ | —H | —C(=NH)NH$_2$ | 1 | N | — |
| 301 | —CHCH$_2$C(CH$_3$)$_3$<br>\|<br>OH | —H | —C(=NH)NH$_2$ | 1 | N | — |
| 302 | —CH(CH$_2$)CH$_2$COOH<br>\|<br>NHSO$_2$C$_6$H$_5$ | —H | —C(=NH)NH$_2$ | 1 | N | — |
| 303 | —CH-C$_6$H$_{11}$<br>\|<br>NHSO$_2$CH$_3$ | —H | —C(=NH)NH$_2$ | 2 | C | Single bond |
| 304 | —CHCH$_2$C(CH$_3$)$_3$<br>\|<br>NHSO$_2$CH$_3$ | —H | —C(=NH)NH$_2$ | 2 | C | Single bond |
| 305 | —CHCH$_2$C$_6$H$_5$<br>\|<br>NHSO$_2$CH$_3$ | —H | —C(=NH)NH$_2$ | 2 | C | Single bond |
| 306 | —CHCH$_2$-C$_6$H$_{11}$<br>\|<br>NHCOOC$_2$H$_5$ | —H | —C(=NH)NH$_2$ | 2 | C | Single bond |
| 307 | —CHCH$_2$C(CH$_3$)$_3$<br>\|<br>NHCOOC$_2$H$_5$ | —H | —C(=NH)NH$_2$ | 2 | C | Single bond |
| 308 | —CHCH$_2$C$_6$H$_5$<br>\|<br>NHCOOC$_2$H$_5$ | —H | —C(=NH)NH$_2$ | 2 | C | Single bond |

TABLE 1-continued

[Structure: pyrrolidine ring with (CH₂)ₙ, N-C(=O)-R¹, α-carbon with C(=O)NCH₂-phenyl(A-R³), R²]

| Compound No. | -R¹ (−D−CH(R⁵)−(CH)ₘ−E−R⁴) | -R² | -R³ | n | A | Broken line |
|---|---|---|---|---|---|---|
| 309 | -(CH₂)₃-phenyl | -H | -C(=NH)NH₂ | 2 | C | Single bond |
| 310 | -CH(NH₂)CH₂-phenyl | -H | -C(=NH)NH₂ | 2 | C | Single bond |
| 311 | -CH(NHCOOCH(CH₃)₂)-cyclohexyl | -H | -C(=NH)NH₂ | 2 | C | Single bond |
| 312 | -CHCH₂C(C₂H₅)₂ with NHCOOC(CH₃)₃ | -H | -C(=NH)NH₂ | 2 | C | Single bond |
| 313 | -CHCH₂C(CH₃)₃ with OH | -H | -C(=NH)NH₂ | 2 | C | Single bond |
| 314 | -CH₂CH(NHSO₂CH₃)-phenyl | -H | -C(=NH)NH₂ | 2 | C | Single bond |
| 315 | -CHCH₂-phenyl with OCOOC₂H₅ | -H | -C(=NH)NH₂ | 2 | C | Single bond |
| 316 | -CH(OH)-cyclohexyl | -H | -C(=NH)NH₂ | 2 | C | Single bond |
| 317 | -CHCH₂-cyclohexyl with NHSO₂CH₃ | -H | -C(=NH)NH₂ | 2 | C | — |
| 318 | -CH-cyclohexyl with NHCOOCH(CH₃)₂ | -H | -C(=NH)NH₂ | 2 | C | — |
| 319 | -CHCH₂-phenyl with NHSO₂CH₃ | -H | -C(=NH)NH₂ | 2 | C | — |

TABLE 1-continued

[Structure: pyrrolidine with (CH₂)ₘ, N-C(=O)-R¹, α-C(=O)NCH₂-phenyl (with broken lines)-A-R³, R² on N]

| Compound No. | -R¹ ( -D-(CH)ₘ-E-R⁴ / R⁵ ) | -R² | -R³ | n | A | Broken line |
|---|---|---|---|---|---|---|
| 320 | -CHCH₂-phenyl / NHCOOC₂H₅ | -H | -C(=NH)NH₂ | 2 | C | — |
| 321 | -CHCH₂C(CH₃)₃ / NHSO₂CH₃ | -H | -C(=NH)NH₂ | 2 | C | — |
| 322 | -CHCH₂CH(C₂H₅)₂ / NHCOOC(CH₃)₃ | -H | -C(=NH)NH₂ | 2 | C | — |
| 323 | -CHCH₂C(CH₃)₃ / OH | -H | -C(=NH)NH₂ | 2 | C | — |
| 324 | -CH-cyclohexyl(H) / NHSO₂CH₃ | -H | -C(=NH)NH₂ | 2 | N | — |
| 325 | -CHCH₂-cyclohexyl(H) / NHCOOC(CH₃)₃ | -H | -C(=NH)NH₂ | 2 | N | — |
| 326 | -CHCH₂-phenyl / NHSO₂CH₃ | -H | -C(=NH)NH₂ | 2 | N | — |
| 327 | -CHCH₂-phenyl / OCOOC₂H₅ | -H | -C(=NH)NH₂ | 2 | N | — |
| 328 | -CHCH₂C(CH₃)₃ / NHSO₂CH₃ | -H | -C(=NH)NH₂ | 2 | N | — |
| 329 | -CH(CH₂)₂SCH₃ / NHCOOCH(CH₃)₂ | -H | -C(=NH)NH₂ | 2 | N | — |
| 330 | -CHCH₂C(CH₃)₃ / OH | -H | -C(=NH)NH₂ | 2 | N | — |

TABLE 1-continued $$\begin{array}{c}\text{structure with }(CH_2)_m\text{, N-C(=O)-R}^1\text{, CNCH}_2\text{-ring-A-R}^3\text{, R}^2\end{array}$$

| Compound No. | $-R^1 \left( \begin{array}{c} -D-(CH)_m-E-R^4 \\ \phantom{-D-(CH)_m-}R^5 \end{array} \right)$ | $-R^2$ | $-R^3$ | n | A | Broken line |
|---|---|---|---|---|---|---|
| 331 | -CHCH$_2$-(cyclohexyl, H) / NHSO$_2$CH$_3$ | -CH$_3$ | -C(=NH)NH$_2$ | 1 | C | Single bond |
| 332 | -CH-(cyclohexyl, H) / NHCOOCH(CH$_3$)$_2$ | -CH$_3$ | -C(=NH)NH$_2$ | 1 | C | Single bond |
| 333 | -CHCH$_2$-(phenyl) / NHSO$_2$CH$_3$ | -CH$_3$ | -C(=NH)NH$_2$ | 1 | C | Single bond |
| 334 | -CHCH$_2$-(phenyl) / OCOOC$_2$H$_5$ | -CH$_3$ | -C(=NH)NH$_2$ | 1 | C | Single bond |
| 335 | -CHCH$_2$C(CH$_3$) / OH | -CH$_3$ | -C(=NH)NH$_2$ | 1 | C | Single bond |
| 336 | -CHCH$_2$CH(C$_2$H$_5$)$_2$ / NHCOOC(CH$_3$)$_3$ | -CH$_3$ | -C(=NH)NH$_2$ | 1 | C | Single bond |
| 337 | -CHCH$_2$C(CH$_3$)$_3$ / NHSO$_2$CH$_3$ | -CH$_3$ | -C(=NH)NH$_2$ | 1 | C | Single bond |
| 338 | -CHCH$_2$-(cyclohexyl, H) / NHSO$_2$CH$_3$ | -CH$_3$ | -C(=NH)NH$_2$ | 1 | C | — |
| 339 | -CH-(cyclohexyl, H) / NHCOOCH(CH$_3$)$_2$ | -CH$_3$ | -C(=NH)NH$_2$ | 1 | C | — |
| 340 | -CHCH$_2$-(phenyl) / NHSO$_2$CH$_3$ | -CH$_3$ | -C(=NH)NH$_2$ | 1 | C | — |
| 341 | -CH$_2$CH-(phenyl) / OCOOC$_2$H$_5$ | -CH$_3$ | -C(=NH)NH$_2$ | 1 | C | — |

TABLE 1-continued

| Compound No. | $-R^1 \left( \begin{array}{c} -D-(CH)_m-E-R^4 \\ R^5 \end{array} \right)$ | $-R^2$ | $-R^3$ | n | A | Broken line |
|---|---|---|---|---|---|---|
| 342 | —CHCH$_2$CH(C$_2$H$_5$)$_2$<br>\|<br>NHCOOC(CH$_3$)$_3$ | —CH$_3$ | $-C\begin{smallmatrix}\nearrow NH \\ \searrow NH_2\end{smallmatrix}$ | 1 | C | — |
| 343 | —CHCH$_2$C(CH$_3$)$_3$<br>\|<br>NHSO$_2$CH$_3$ | —CH$_3$ | $-C\begin{smallmatrix}\nearrow NH \\ \searrow NH_2\end{smallmatrix}$ | 1 | C | — |
| 344 | —CHCH$_2$C(CH$_3$)$_3$<br>\|<br>OH | —CH$_3$ | $-C\begin{smallmatrix}\nearrow NH \\ \searrow NH_2\end{smallmatrix}$ | 1 | C | — |
| 345 | —CHCH$_2$—cyclohexyl(H)<br>\|<br>NHSO$_2$CH$_3$ | —CH$_3$ | $-C\begin{smallmatrix}\nearrow NH \\ \searrow NH_2\end{smallmatrix}$ | 1 | N | — |
| 346 | —CH$_2$CH—phenyl<br>\|<br>NHCOOCH(CH$_3$)$_2$ | —CH$_3$ | $-C\begin{smallmatrix}\nearrow NH \\ \searrow NH_2\end{smallmatrix}$ | 1 | N | — |
| 347 | —CHCH$_2$—phenyl<br>\|<br>NHSO$_2$CH$_3$ | —CH$_3$ | $-C\begin{smallmatrix}\nearrow NH \\ \searrow NH_2\end{smallmatrix}$ | 1 | N | — |
| 348 | —CH—phenyl<br>\|<br>OCOOC$_2$H$_5$ | —CH$_3$ | $-C\begin{smallmatrix}\nearrow NH \\ \searrow NH_2\end{smallmatrix}$ | 1 | N | — |
| 349 | —CHCH$_2$C(CH$_3$)$_3$<br>\|<br>NHSO$_2$CH$_3$ | —CH$_3$ | $-C\begin{smallmatrix}\nearrow NH \\ \searrow NH_2\end{smallmatrix}$ | 1 | N | — |
| 350 | —CHCH$_2$CH(C$_2$H$_5$)$_2$<br>\|<br>NHCOOC(CH$_3$)$_3$ | —CH$_3$ | $-C\begin{smallmatrix}\nearrow NH \\ \searrow NH_2\end{smallmatrix}$ | 1 | N | — |
| 351 | —CHCH$_2$C(CH$_3$)$_3$<br>\|<br>OH | —CH$_3$ | $-C\begin{smallmatrix}\nearrow NH \\ \searrow NH_2\end{smallmatrix}$ | 1 | N | — |
| 352 | —CH—cyclohexyl(H)<br>\|<br>NHSO$_2$CH$_3$ | —CH$_3$ | $-C\begin{smallmatrix}\nearrow NH \\ \searrow NH_2\end{smallmatrix}$ | 2 | C | Single bond |

TABLE 1-continued

| Compound No. | -R¹ (-D-(CH)ₘ-E-R⁴ / R⁵) | -R² | -R³ | n | A | Broken line |
|---|---|---|---|---|---|---|
| 353 | -CHCH₂-(C₆H₁₁, H) / NHCOOCH(CH₃)₂ | -CH₃ | -C(=NH)NH₂ | 2 | C | Single bond |
| 354 | -CHCH₂-Ph / NHSO₂CH₃ | -CH₃ | -C(=NH)NH₂ | 2 | C | Single bond |
| 355 | -CH₂CH(Ph) / OCOOC₂H₅ | -CH₃ | -C(=NH)NH₂ | 2 | C | Single bond |
| 356 | -CHCH₂C(CH₃)₃ / NHSO₂CH₃ | -CH₃ | -C(=NH)NH₂ | 2 | C | Single bond |
| 357 | -CH(CH₂)₄CH₃ / NHCOOC(CH₃)₃ | -CH₃ | -C(=NH)NH₂ | 2 | C | Single bond |
| 358 | -CHCH₂CH(CH₃)₂ / OH | -CH₃ | -C(=NH)NH₂ | 2 | C | Single bond |
| 359 | -CH-(C₆H₁₁, H) / NHSO₂CH₃ | -CH₃ | -C(=NH)NH₂ | 2 | C | — |
| 360 | -CHCH₂-(C₆H₁₁, H) / NHCOOC₂H₅ | -CH₃ | -C(=NH)NH₂ | 2 | C | — |
| 361 | -CHCH₂-Ph / NHSO₂CH₃ | -CH₃ | -C(=NH)NH₂ | 2 | C | — |
| 362 | -CH₂CH(Ph) / OCOOCH(CH₃)₂ | -CH₃ | -C(=NH)NH₂ | 2 | C | — |
| 363 | -CHCH₂C(CH₃)₃ / NHSO₂CH₃ | -CH₃ | -C(=NH)NH₂ | 2 | C | — |

TABLE 1-continued

| Compound No. | -R¹ ( -D-(CH)ₘ-E-R⁴ / R⁵ ) | -R² | -R³ | n | A | Broken line |
|---|---|---|---|---|---|---|
| 364 | -CHC(SCH₃)(CH₃)₂<br>\|<br>NHCOOC(CH₃)₃ | -CH₃ | -C(=NH)NH₂ | 2 | C | — |
| 365 | -CHCH₂CH(CH₃)₃<br>\|<br>NH₂ | -CH₃ | -C(=NH)NH₂ | 2 | C | — |
| 366 | -CHCH₂-C₆H₁₁<br>\|<br>NHCOOC₂H₅ | -CH₃ | -C(=NH)NH₂ | 2 | N | — |
| 367 | -CHCH₂-C₆H₁₁<br>\|<br>NHSO₂CH₃ | -CH₃ | -C(=NH)NH₂ | 2 | N | — |
| 368 | -CH-C₆H₅<br>\|<br>NHSO₂CH₃ | -CH₃ | -C(=NH)NH₂ | 2 | N | — |
| 369 | -CHCH₂-C₆H₄-COOH<br>\|<br>OCOOCH(CH₃)₂ | -CH₃ | -C(=NH)NH₂ | 2 | N | — |
| 370 | -CHCH₂C(CH₃)₃<br>\|<br>NHSO₂CH₂COOH | -CH₃ | -C(=NH)NH₂ | 2 | N | — |
| 371 | -CH(CH₂)₂SCH₃<br>\|<br>NHCOOC(CH₃)₃ | -CH₃ | -C(=NH)NH₂ | 2 | N | — |
| 372 | -CH₂CH(CH₂)₃CH₃<br>\|<br>OH | -CH₃ | -C(=NH)NH₂ | 2 | N | — |
| 373 | -C₆H₅ | -H | -C(=NOH)NH₂ | 1 | C | Single bond |
| 374 | -CH₂-C₆H₅ | -H | -C(=NOH)NH₂ | 1 | C | Single bond |

TABLE 1-continued

| Compound No. | -R¹ (-D-(CH)ₘ-E-R⁴ / R⁵) | -R² | -R³ | n | A | Broken line |
|---|---|---|---|---|---|---|
| 375 | -CH₂-(1-naphthyl) | -H | -C(=NOH)NH₂ | 1 | C | Single bond |
| 376 | -CH₂-cyclohexyl (H) | -H | -C(=NOH)NH₂ | 1 | C | Single bond |
| 377 | -CH₂-(2-thienyl) | -H | -C(=NOH)NH₂ | 1 | C | Single bond |
| 378 | -CH₂O-(2-methoxyphenyl) | -H | -C(=NOH)NH₂ | 1 | C | Single bond |
| 379 | -CH₂OCH₂-C₆H₄-COOH | -H | -C(=NOH)NH₂ | 1 | C | Single bond |
| 380 | -CH₂SC₂H₅ | -H | -C(=NOH)NH₂ | 1 | C | Single bond |
| 381 | -(CH₂)₄COOH | -H | -C(=NOH)NH₂ | 1 | C | Single bond |
| 382 | -CH(NHSO₂CH₃)CH₂-C₆H₅ | -H | -C(=NOH)NH₂ | 1 | C | Single bond |
| 383 | -CH(OH)CH₂-C₆H₅ | -H | -C(=NOH)NH₂ | 1 | C | Single bond |
| 384 | -CH(OCOOC₂H₅)CH₂-C₆H₅ | -H | -C(=NOH)NH₂ | 1 | C | Single bond |

TABLE 1-continued

| Compound No. | $-R^1 \left( \begin{array}{c} -D-(CH)_m-E-R^4 \\ R^5 \end{array} \right)$ | $-R^2$ | $-R^3$ | n | A | Broken line |
|---|---|---|---|---|---|---|
| 385 | −CHCH₂−(phenyl), OCOOCH(CH₃)₂ | −H | −C(=NOH)NH₂ | 1 | C | Single bond |
| 386 | −CH₂CH−(phenyl), NHCHO | −H | −C(=NOH)NH₂ | 1 | C | Single bond |
| 387 | −CHCH₂−(phenyl), NHCOOC₂H₅ | −H | −C(=NOH)NH₂ | 1 | C | Single bond |
| 388 | −CHCH₂−(phenyl), NHCOOCH(CH₃)₂ | −H | −C(=NOH)NH₂ | 1 | C | Single bond |
| 389 | −CHCH₂−(phenyl), NHCOOC(CH₃)₃ | −H | −C(=NOH)NH₂ | 1 | C | Single bond |
| 390 | −CHCH₂−(phenyl), NH₂ | −H | −C(=NOH)NH₂ | 1 | C | Single bond |
| 391 | −CH−(cyclohexyl-H), OH | −H | −C(=NOH)NH₂ | 1 | C | Single bond |
| 392 | −CHCH₂−(cyclohexyl-H), OCOCH₃ | −H | −C(=NOH)NH₂ | 1 | C | Single bond |
| 393 | −CHCH₂−(phenyl), OCOOC₂H₅ | −H | −C(=NOH)NH₂ | 1 | C | Single bond |
| 394 | −CH−(cyclohexyl-H), NHCOOC₂H₅ | −H | −C(=NOH)NH₂ | 1 | C | Single bond |
| 395 | −CHCH₂−(phenyl), NHCOOCH(CH₃)₂ | −H | −C(=NOH)NH₂ | 1 | C | Single bond |

TABLE 1-continued

Structure: pyrrolidine-(CH₂)ₘ with N-C(=O)-R¹, attached via C(=O)N(R²)CH₂ to a six-membered ring A-R³

| Compound No. | -R¹ ( -D-(CH)ₘ-E-R⁴ / R⁵ ) | -R² | -R³ | n | A | Broken line |
|---|---|---|---|---|---|---|
| 396 | -CH(cyclohexyl)-NHCOOC(CH₃)₃ | -H | -C(=NOH)NH₂ | 1 | C | Single bond |
| 397 | -CHCH₂(cyclohexyl)-NHCOOC(CH₃)₃ | -H | -C(=NOH)NH₂ | 1 | C | Single bond |
| 398 | -CH(cyclohexyl)-NHSO₂CH₃ | -H | -C(=NOH)NH₂ | 1 | C | Single bond |
| 399 | -CHCH₂(cyclohexyl)-NHSO₂CH₃ | -H | -C(=NOH)NH₂ | 1 | C | Single bond |
| 400 | -CHCH₂(cyclohexyl)-NH₂ | -H | -C(=NOH)NH₂ | 1 | C | Single bond |
| 401 | -CH(phenyl)-OH | -H | -C(=NOH)NH₂ | 1 | C | Single bond |
| 402 | -CH(phenyl)-NH₂ | -H | -C(=NOH)NH₂ | 1 | C | Single bond |
| 403 | -CH(phenyl)-NHCOOC₂H₅ | -H | -C(=NOH)NH₂ | 1 | C | Single bond |
| 404 | -CH(phenyl)-NHCOOC(CH₃)₃ | -H | -C(=NOH)NH₂ | 1 | C | Single bond |
| 405 | -CHCH₂CH(CH₃)₂ / NHCOOC₂H₅ | -H | -C(=NOH)NH₂ | 1 | C | Single bond |
| 406 | -CHCH₂CH(CH₃)₂ / NHCOOC(CH₃)₃ | -H | -C(=NOH)NH₂ | 1 | C | Single bond |

TABLE 1-continued $$\text{structure with } (CH_2)_n, \text{ N-C(=O)-R}^1, \text{ CNCH}_2\text{(R}^2\text{)-phenyl-A-R}^3$$

| Compound No. | $-R^1\left(\begin{array}{c}-D-(CH)_m-E-R^4\\ |\\ R^5\end{array}\right)$ | $-R^2$ | $-R^3$ | n | A | Broken line |
|---|---|---|---|---|---|---|
| 407 | $-\underset{\underset{NHCOOC_2H_5}{|}}{CHCH(CH_3)_2}$ | $-H$ | $-C\underset{\diagdown NH_2}{\overset{\diagup NOH}{\phantom{C}}}$ | 1 | C | Single bond |
| 408 | $-\underset{\underset{NHCOOC(CH_3)_3}{|}}{CHCH(CH_3)_2}$ | $-H$ | $-C\underset{\diagdown NH_2}{\overset{\diagup NOH}{\phantom{C}}}$ | 1 | C | Single bond |
| 409 | $-\underset{\underset{NHCOOC_2H_5}{|}}{CHC(CH_3)_3}$ | $-H$ | $-C\underset{\diagdown NH_2}{\overset{\diagup NOH}{\phantom{C}}}$ | 1 | C | Single bond |
| 410 | $-\underset{\underset{NHCOOC(CH_3)_3}{|}}{CHC(CH_3)_3}$ | $-H$ | $-C\underset{\diagdown NH_2}{\overset{\diagup NOH}{\phantom{C}}}$ | 1 | C | Single bond |
| 411 | $-\underset{\underset{NHCOOC_2H_5}{|}}{CH(CH_2)_4CH_3}$ | $-H$ | $-C\underset{\diagdown NH_2}{\overset{\diagup NOH}{\phantom{C}}}$ | 1 | C | Single bond |
| 412 | $-\underset{\underset{NHCOOC(CH_3)_3}{|}}{CH(CH_2)_4CH_3}$ | $-H$ | $-C\underset{\diagdown NH_2}{\overset{\diagup NOH}{\phantom{C}}}$ | 1 | C | Single bond |
| 413 | $-\underset{\underset{NHCOOC_2H_5}{|}}{CHCH_2CH_2SCH_3}$ | $-H$ | $-C\underset{\diagdown NH_2}{\overset{\diagup NOH}{\phantom{C}}}$ | 1 | C | Single bond |
| 414 | $-\underset{\underset{NHCOOC(CH_3)_3}{|}}{CHCH_2CH_2SCH_3}$ | $-H$ | $-C\underset{\diagdown NH_2}{\overset{\diagup NOH}{\phantom{C}}}$ | 1 | C | Single bond |
| 415 | $-\underset{\underset{OCOOC_2H_5}{|}}{CH(CH_2)_4CH_3}$ | $-H$ | $-C\underset{\diagdown NH_2}{\overset{\diagup NOH}{\phantom{C}}}$ | 1 | C | Single bond |
| 416 | $-\underset{\underset{OCOOC_2H_5}{|}}{CHCH_2C(CH_3)_3}$ | $-H$ | $-C\underset{\diagdown NH_2}{\overset{\diagup NOH}{\phantom{C}}}$ | 1 | C | Single bond |
| 417 | $-\underset{\underset{NHCOOC_2H_5}{|}}{CHCH_2CH(C_2H_5)_2}$ | $-H$ | $-C\underset{\diagdown NH_2}{\overset{\diagup NOH}{\phantom{C}}}$ | 1 | C | Single bond |

TABLE 1-continued

| Compound No. | $-R^1$ $\left(\begin{array}{c}-D-(CH)_m-E-R^4\\ \|\\ R^5\end{array}\right)$ | $-R^2$ | $-R^3$ | n | A | Broken line |
|---|---|---|---|---|---|---|
| 418 | —CHCH$_2$C(CH$_3$)$_3$<br>\|<br>NHCOOC$_2$H$_5$ | —H | —C(=NOH)NH$_2$ | 1 | C | Single bond |
| 419 | —CHC(SCH$_3$)(CH$_3$)$_2$<br>\|<br>NHCOOC$_2$H$_5$ | —H | —C(=NOH)NH$_2$ | 1 | C | Single bond |
| 420 | —CHCH$_2$C(CH$_3$)$_3$<br>\|<br>NHCOOCH(CH$_3$)$_2$ | —H | —C(=NOH)NH$_2$ | 1 | C | Single bond |
| 421 | —CHCH$_2$C(CH$_3$)$_3$<br>\|<br>NH$_2$ | —H | —C(=NOH)NH$_2$ | 1 | C | Single bond |
| 422 | —CH(OH)—C$_6$H$_{11}$ | —H | —C(=NOH)NH$_2$ | 1 | C | — |
| 423 | —CHCH$_2$—C$_6$H$_{11}$<br>\|<br>OCOCH$_3$ | —H | —C(=NOH)NH$_2$ | 1 | C | — |
| 424 | —CHCH$_2$—C$_6$H$_{11}$<br>\|<br>OCOOC$_2$H$_5$ | —H | —C(=NOH)NH$_2$ | 1 | C | — |
| 425 | —CH(NH$_2$)—C$_5$H$_9$ | —H | —C(=NOH)NH$_2$ | 1 | C | — |
| 426 | —CHCH$_2$—C$_6$H$_{11}$<br>\|<br>NH$_2$ | —H | —C(=NOH)NH$_2$ | 1 | C | — |
| 427 | —CH(NHCHO)—C$_6$H$_{11}$ | —H | —C(=NOH)NH$_2$ | 1 | C | — |
| 428 | —CHCH$_2$—C$_6$H$_{11}$<br>\|<br>NHCOOC$_2$H$_5$ | —H | —C(=NOH)NH$_2$ | 1 | C | — |

TABLE 1-continued

| Compound No. | -R¹ ( -D-(CH)ₘ-E-R⁴ / R⁵ ) | -R² | -R³ | n | A | Broken line |
|---|---|---|---|---|---|---|
| 429 | -CH(cyclopentyl-H) / NHCOOCH(CH₃)₂ | -H | -C(=NOH)NH₂ | 1 | C | — |
| 430 | -CH(cyclohexyl-H) / NHCOOCH(CH₃)₂ | -H | -C(=NOH)NH₂ | 1 | C | — |
| 431 | -CHCH₂(cyclohexyl-H) / NHCOOCH(CH₃)₂ | -H | -C(=NOH)NH₂ | 1 | C | — |
| 432 | -CH(cyclopentyl-H) / NHCOOC(CH₃)₃ | -H | -C(=NOH)NH₂ | 1 | C | — |
| 433 | -CH(cyclohexyl-H) / NHCOOC(CH₃)₃ | -H | -C(=NOH)NH₂ | 1 | C | — |
| 434 | -CHCH₂(cyclopentyl-H) / NHCOOC(CH₃)₃ | -H | -C(=NOH)NH₂ | 1 | C | — |
| 435 | -CHCH₂(cyclohexyl-H) / NHCOOC(CH₃)₃ | -H | -C(=NOH)NH₂ | 1 | C | — |
| 436 | -CH(cyclohexyl-H) / NHCOOCH₂(phenyl) | -H | -C(=NOH)NH₂ | 1 | C | — |
| 437 | -CH(cyclopentyl-H) / NHSO₂CH₃ | -H | -C(=NOH)NH₂ | 1 | C | — |
| 438 | -CH(cyclohexyl-H) / NHSO₂CH₃ | -H | -C(=NOH)NH₂ | 1 | C | — |

TABLE 1-continued

| Compound No. | -R$^1$ $\left(\begin{array}{c}-D-(CH)_m-E-R^4\\R^5\end{array}\right)$ | -R$^2$ | -R$^3$ | n | A | Broken line |
|---|---|---|---|---|---|---|
| 439 | -CHCH$_2$-(cyclohexyl), NHSO$_2$CH$_3$ | -H | -C(=NOH)NH$_2$ | 1 | C | — |
| 440 | -CH(cyclohexyl), NHSO$_2$-phenyl | -H | -C(=NOH)NH$_2$ | 1 | C | — |
| 441 | -CHCH$_2$-(cyclohexyl), NHSO$_2$-phenyl | -H | -C(=NOH)NH$_2$ | 1 | C | — |
| 442 | -CHCH$_2$-(cyclohexyl), NHSO$_2$CH$_2$COOH | -H | -C(=NOH)NH$_2$ | 1 | C | — |
| 443 | -CH(phenyl), OH | -H | -C(=NOH)NH$_2$ | 1 | C | — |
| 444 | -CHCH$_2$-phenyl, NH$_2$ | -H | -C(=NOH)NH$_2$ | 1 | C | — |
| 445 | -CH$_2$CH(phenyl), OCOCH$_3$ | -H | -C(=NOH)NH$_2$ | 1 | C | — |
| 446 | -CHCH$_2$-phenyl, OCOOC$_2$H$_5$ | -H | -C(=NOH)NH$_2$ | 1 | C | — |
| 447 | -CHCH$_2$-phenyl, NHCOOC$_2$H$_5$ | -H | -C(=NOH)NH$_2$ | 1 | C | — |
| 448 | -CHCH$_2$-phenyl, NHCOOCH(CH$_3$)$_2$ | -H | -C(=NOH)NH$_2$ | 1 | C | — |

TABLE 1-continued

| Compound No. | $-R^1 \left( \begin{array}{c} -D-(CH)_m-E-R^4 \\ R^5 \end{array} \right)$ | $-R^2$ | $-R^3$ | n | A | Broken line |
|---|---|---|---|---|---|---|
| 449 | -CHCH$_2$-C$_6$H$_5$<br>\|<br>NHCOOC(CH$_3$)$_3$ | -H | -C(=NOH)NH$_2$ | 1 | C | — |
| 450 | -CHCH$_2$-C$_6$H$_5$<br>\|<br>NHCOOCH$_2$-C$_6$H$_5$ | -H | -C(=NOH)NH$_2$ | 1 | C | — |
| 451 | -CH$_2$CH-C$_6$H$_5$<br>\|<br>NHSO$_2$CH$_3$ | -H | -C(=NOH)NH$_2$ | 1 | C | — |
| 452 | -CHCH$_2$-C$_6$H$_5$<br>\|<br>NHSO$_2$CH$_3$ | -H | -C(=NOH)NH$_2$ | 1 | C | — |
| 453 | -CH(CH$_2$)$_4$CH$_3$<br>\|<br>OH | -H | -C(=NOH)NH$_2$ | 1 | C | — |
| 454 | -CHCH$_2$C(CH$_3$)$_3$<br>\|<br>OH | -H | -C(=NOH)NH$_2$ | 1 | C | — |
| 455 | -CHCH$_2$CH(C$_2$H$_5$)$_2$<br>\|<br>OCOCH$_3$ | -H | -C(=NOH)NH$_2$ | 1 | C | — |
| 456 | -CHCH$_2$C(CH$_3$)$_3$<br>\|<br>OCOOC$_2$H$_5$ | -H | -C(=NOH)NH$_2$ | 1 | C | — |
| 457 | -CH$_2$CH(CH$_2$)$_2$CH$_3$<br>\|<br>NHCHO | -H | -C(=NOH)NH$_2$ | 1 | C | — |
| 458 | -CHCH$_2$C(CH$_3$)$_3$<br>\|<br>NHCOOCH$_3$ | -H | -C(=NOH)NH$_2$ | 1 | C | — |
| 459 | -CH(CH$_2$)$_4$CH$_3$<br>\|<br>NHCOOC$_2$H$_5$ | -H | -C(=NOH)NH$_2$ | 1 | C | — |

TABLE 1-continued

Structure header: pyrrolidine with (CH$_2$)$_m$, N-C(=O)-R$^1$, carbonyl-CNCH$_2$ to phenyl with A-R$^3$, R$^2$ on N.

| Compound No. | -R$^1$ ( -D-(CH)$_m$-E-R$^4$ / R$^5$ ) | -R$^2$ | -R$^3$ | n | A | Broken line |
|---|---|---|---|---|---|---|
| 460 | -CHCH$_2$CH(C$_2$H$_5$)$_2$ / NHCOOC$_2$H$_5$ | -H | -C(=NOH)NH$_2$ | 1 | C | — |
| 461 | -CHCH$_2$C(CH$_3$)$_3$ / NHCOOC$_2$H$_5$ | -H | -C(=NOH)NH$_2$ | 1 | C | — |
| 462 | -CH(CH$_2$)$_4$CH$_3$ / NHCOOCH(CH$_3$)$_2$ | -H | -C(=NOH)NH$_2$ | 1 | C | — |
| 463 | -CHCH$_2$CH(C$_2$H$_5$)$_2$ / NHCOOCH(CH$_3$)$_2$ | -H | -C(=NOH)NH$_2$ | 1 | C | — |
| 464 | -CHCH$_2$C(CH$_3$)$_3$ / NHCOOCH(CH$_3$)$_2$ | -H | -C(=NOH)NH$_2$ | 1 | C | — |
| 465 | -CH(CH$_2$)$_4$CH$_3$ / NHCOOC(CH$_3$)$_3$ | -H | -C(=NOH)NH$_2$ | 1 | C | — |
| 466 | -CHCH$_2$CH(C$_2$H$_5$)$_2$ / NHCOOC(CH$_3$)$_3$ | -H | -C(=NOH)NH$_2$ | 1 | C | — |
| 467 | -CHCH$_2$C(CH$_3$)$_3$ / NHCOOC(CH$_3$)$_3$ | -H | -C(=NOH)NH$_2$ | 1 | C | — |
| 468 | -CH(CH$_2$)$_2$SCH$_3$ / NHCOOC(CH$_3$)$_3$ | -H | -C(=NOH)NH$_2$ | 1 | C | — |
| 469 | -CHCH$_2$C(CH$_3$)$_3$ / NHCOOCH$_2$-C$_6$H$_5$ | -H | -C(=NOH)NH$_2$ | 1 | C | — |
| 470 | -CHCH$_2$C(CH$_3$)$_3$ / NH$_2$ | -H | -C(=NOH)NH$_2$ | 1 | C | — |

TABLE 1-continued

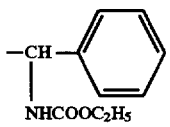

| Compound No. | -R¹ (-D-(CH)ₘ-E-R⁴ / R⁵) | -R² | -R³ | n | A | Broken line |
|---|---|---|---|---|---|---|
| 471 | -CH(C₆H₅)<br>NHCOOC₂H₅ | -H | -C(=NOH)NH₂ | 1 | C | — |
| 472 | -CH(C₆H₅)<br>NHCOOC(CH₃)₃ | -H | -C(=NOH)NH₂ | 1 | C | — |
| 473 | -CHCH₂CH(CH₃)₂<br>NHCOOC₂H₅ | -H | -C(=NOH)NH₂ | 1 | C | — |
| 474 | -CHCH₂CH(CH₃)₂<br>NHCOOC(CH₃)₃ | -H | -C(=NOH)NH₂ | 1 | C | — |
| 475 | -CH(CH₂)₂CH₃<br>NHCOOCH(CH₃)₂ | -H | -C(=NOH)NH₂ | 1 | C | — |
| 476 | -CH(CH₂)₂CH₃<br>NHCOOC(CH₃)₃ | -H | -C(=NOH)NH₂ | 1 | C | — |
| 477 | -CHCH(CH₃)₂<br>NHCOOCH(CH₃)₂ | H | -C(=NOH)NH₂ | 1 | C | — |
| 478 | -CHCH(CH₃)₂<br>NHCOOC(CH₃)₃ | -H | -C(=NOH)NH₂ | 1 | C | — |
| 479 | -CHC(CH₃)₃<br>NHCOOCH(CH₃)₂ | -H | -C(=NOH)NH₂ | 1 | C | — |
| 480 | -CHC(CH₃)₃<br>NHCOOC(CH₃)₃ | -H | -C(=NOH)NH₂ | 1 | C | — |
| 481 | -CHCH₂Si(CH₃)₃<br>NHCOOC₂H₅ | -H | -C(=NOH)NH₂ | 1 | C | — |

TABLE 1-continued

| Compound No. | $-R^1 \left( \begin{array}{c} -D-(CH)_m-E-R^4 \\ \| \\ R^5 \end{array} \right)$ | $-R^2$ | $-R^3$ | n | A | Broken line |
|---|---|---|---|---|---|---|
| 482 | —CHCH$_2$Si(CH$_3$)$_3$<br>\|<br>NHCOOCH(CH$_3$)$_2$ | —H | —C(=NOH)NH$_2$ | 1 | C | — |
| 483 | —CHCH$_2$CH$_2$SCH$_3$<br>\|<br>NHCOOC$_2$H$_5$ | —H | —C(=NOH)NH$_2$ | 1 | C | — |
| 484 | —CHCH$_2$CH$_2$SCH$_3$<br>\|<br>NHCOOCH(CH$_3$)$_2$ | —H | —C(=NOH)NH$_2$ | 1 | C | — |
| 485 | —CHCH$_2$OC(CH$_3$)$_3$<br>\|<br>NHCOOC$_2$H$_5$ | —H | —C(=NOH)NH$_2$ | 1 | C | — |
| 486 | —CHCH$_2$OC(CH$_3$)$_3$<br>\|<br>NHCOOCH(CH$_3$)$_2$ | —H | —C(=NOH)NH$_2$ | 1 | C | — |
| 487 | —CHCH$_2$OC(CH$_3$)$_2$C$_2$H$_5$<br>\|<br>NHCOOC$_2$H$_5$ | —H | —C(=NOH)NH$_2$ | 1 | C | — |
| 488 | —CHCH$_2$OC(CH$_3$)$_2$C$_2$H$_5$<br>\|<br>NHCOOCH(CH$_3$)$_2$ | —H | —C(=NOH)NH$_2$ | 1 | C | — |
| 489 | —CHCH$_2$OC(C$_2$H$_5$)$_2$CH$_3$<br>\|<br>NHCOOC$_2$H$_5$ | —H | —C(=NOH)NH$_2$ | 1 | C | — |
| 490 | —CHCH$_2$OC(C$_2$H$_5$)$_2$CH$_3$<br>\|<br>NHCOOCH(CH$_3$)$_2$ | —H | —C(=NOH)NH$_2$ | 1 | C | — |
| 491 | —CHCH$_2$OC(CH$_3$)$_2$CH(CH$_3$)$_2$<br>\|<br>NHCOOCH(CH$_3$)$_2$ | —H | —C(=NOH)NH$_2$ | 1 | C | — |
| 492 | —CHCH$_2$SC(C$_3$)$_3$<br>\|<br>NHCOOC$_2$H$_5$ | —H | —C(=NOH)NH$_2$ | 1 | C | — |
| 493 | —CHCH$_2$SC(CH$_3$)$_2$C$_2$H$_5$<br>\|<br>NHCOOC$_2$H$_5$ | —H | —C(=NOH)NH$_2$ | 1 | C | — |

TABLE 1-continued

| Compound No. | $-R^1 \left( \begin{array}{c} -D-(CH)_m-E-R^4 \\ \| \\ R^5 \end{array} \right)$ | $-R^2$ | $-R^3$ | n | A | Broken line |
|---|---|---|---|---|---|---|
| 494 | $-CHCH_2SC(CH_3)_2C_2H_5$<br>$\|$<br>$NHCOOCH(CH_3)_2$ | $-H$ | $-C \begin{array}{c} NOH \\ \backslash NH_2 \end{array}$ | 1 | C | — |
| 495 | $-CHC(CH_3)_2SC_2H_5$<br>$\|$<br>$NHCOOC_2H_5$ | $-H$ | $-C \begin{array}{c} NOH \\ \backslash NH_2 \end{array}$ | 1 | C | — |
| 496 | $-CHC(CH_3)_2SC_2H_5$<br>$\|$<br>$NHCOOCH(CH_3)_2$ | $-H$ | $-C \begin{array}{c} NOH \\ \backslash NH_2 \end{array}$ | 1 | C | — |
| 497 | $-CHC(CH_3)_2SCH(CH_3)_2$<br>$\|$<br>$NHCOOC_2H_5$ | $-H$ | $-C \begin{array}{c} NOH \\ \backslash NH_2 \end{array}$ | 1 | C | — |
| 498 | $-CHC(CH_3)_2SCH(CH_3)_2$<br>$\|$<br>$NHCOOCH(CH_3)_2$ | $-H$ | $-C \begin{array}{c} NOH \\ \backslash NH_2 \end{array}$ | 1 | C | — |
| 499 | $-CHC(CH_3)_2SCH(C_2H_5)_2$<br>$\|$<br>$NHCOOC_2H_5$ | $-H$ | $-C \begin{array}{c} NOH \\ \backslash NH_2 \end{array}$ | 1 | C | — |
| 500 | $-CHC(CH_3)_2SCH(C_2H_5)_2$<br>$\|$<br>$NHCOOCH(CH_3)_2$ | $-H$ | $-C \begin{array}{c} NOH \\ \backslash NH_2 \end{array}$ | 1 | C | — |
| 501 | $-CH(CH_2)_4CH_3$<br>$\|$<br>$NHSO_2CH_3$ | $-H$ | $-C \begin{array}{c} NOH \\ \backslash NH_2 \end{array}$ | 1 | C | — |
| 502 | $-CHCH_2C(CH_3)_3$<br>$\|$<br>$NHSO_2CH_3$ | $-H$ | $-C \begin{array}{c} NOH \\ \backslash NH_2 \end{array}$ | 1 | C | — |
| 503 | $-CHCH_2CH(C_2H_5)_2$<br>$\|$<br>$NHSO_2$-Ph | $-H$ | $-C \begin{array}{c} NOH \\ \backslash NH_2 \end{array}$ | 1 | C | — |
| 504 | $-CHCH_2C(CH_3)_3$<br>$\|$<br>$NHSO_2$-Ph | $-H$ | $-C \begin{array}{c} NOH \\ \backslash NH_2 \end{array}$ | 1 | C | — |

TABLE 1-continued

| Compound No. | -R¹ ( -D-(CH)ₘ-E-R⁴ / R⁵ ) | -R² | -R³ | n | A | Broken line |
|---|---|---|---|---|---|---|
| 505 | -CH(cyclopentyl-H)-NHCOOCH(CH₃)₂ | -H | -C(=NOH)NH₂ | 1 | N | — |
| 506 | -CHCH₂(cyclohexyl-H)-NHCOOC₂H₅ | -H | -C(=NOH)NH₂ | 1 | N | — |
| 507 | -CH₂CH(phenyl)-NH | -H | -C(=NOH)NH₂ | 1 | N | — |
| 508 | -CHCH₂(phenyl)-NHCOOCCH₃)₃ | -H | -C(=NOH)NH₂ | 1 | N | — |
| 509 | -CHCH₂C(CH₃)₃-NHCOOC₂H₅ | -H | -C(=NOH)NH₂ | 1 | N | — |
| 510 | -CH(CH₂)₂SCH₃-NHSO₂CH₃ | -H | -C(=NOH)NH₂ | 1 | N | — |
| 511 | -CHCH₂(cyclohexyl-H)-NHCOOCH(CH₃)₂ | -CH₃ | -C(=NOH)NH₂ | 2 | C | Single bond |
| 512 | -CHCH₂(phenyl)-NHCOOC(CH₃)₃ | -CH₃ | -C(=NOH)NH₂ | 2 | C | Single bond |
| 513 | -CHCH₂C(CH₃)₃-NHCOOCH(CH₃)₂ | -CH₃ | -C(=NOH)NH₂ | 2 | C | Single bond |
| 514 | -CHCH₂C(CH₃)₃-NHCOOC(CH₃)₃ | -CH₃ | -C(=NOH)NH₂ | 2 | C | Single bond |
| 515 | -CH(cyclohexyl-H)-NHCOOC(CH₃)₃ | -H | -C(=NOCOOCH₃)NH₂ | 1 | C | Single bond |

TABLE 1-continued

Structure:

$$\text{Core structure with } (CH_2)_n \text{ ring, N-C(=O)-R}^1, \text{ -CNCH}_2\text{-phenyl-A-R}^3, \text{ with R}^2$$

| Compound No. | $-R^1 \left( \begin{array}{c} -D-(CH)_m-E-R^4 \\ | \\ R^5 \end{array} \right)$ | $-R^2$ | $-R^3$ | n | A | Broken line |
|---|---|---|---|---|---|---|
| 516 | -CHCH₂-(cyclohexyl-H) / NHCOOCH(CH₃)₂ | -H | -C(=NOCOOCH₃)NH₂ | 1 | C | Single bond |
| 517 | -CHCH₂-(cyclohexyl-H) / OH | -H | -C(=NOCOOCH₃)NH₂ | 1 | C | Single bond |
| 518 | -CHCH₂-(phenyl) / NHCOOC₂H₅ | -H | -C(=NOCOOCH₃)NH₂ | 1 | C | Single bond |
| 519 | -CHCH₂-(phenyl) / NHSO₂CH₃ | -H | -C(=NOCOOCH₃)NH₂ | 1 | C | Single bond |
| 520 | -CH-(phenyl) / OH | -H | -C(=NOCOOCH₃)NH₂ | 1 | C | Single bond |
| 521 | -CHCH₂C(CH₃)₃ / NHCOOC₂H₅ | -H | -C(=NOCOOCH₃)NH₂ | 1 | C | Single bond |
| 522 | -CHCH₂C(CH₃)₃ / NHCOOCH(CH₃)₂ | -H | -C(=NOCOOCH₃)NH₂ | 1 | C | Single bond |
| 523 | -CHCH₂C(CH₃)₃ / NHCOOC(CH₃)₃ | -H | -C(=NOCOOCH₃)NH₂ | 1 | C | Single bond |
| 524 | -CHCH₂C(CH₃)₃ / OH | -H | -C(=NOCOOCH₃)NH₂ | 1 | C | Single bond |
| 525 | -CH-(cyclohexyl-H) / NHCOOC(CH₃)₃ | -H | -C(=NOCOOCH₃)NH₂ | 1 | C | — |
| 526 | -CHCH₂-(cyclohexyl-H) / NHCOOCH(CH₃)₂ | -H | -C(=NOCOOCH₃)NH₂ | 1 | C | — |

TABLE 1-continued $$\text{structure with } (CH_2)_n, \text{ N-C(=O)-R}^1, \text{ CH(R}^2\text{)-C(=O)-NCH}_2\text{-ring-A-R}^3$$

| Compound No. | $-R^1$ $\left(\begin{array}{c}-D-(CH)_m-E-R^4\\R^5\end{array}\right)$ | $-R^2$ | $-R^3$ | n | A | Broken line |
|---|---|---|---|---|---|---|
| 527 | $-\underset{OH}{CH}-\text{cyclohexyl(H)}$ | $-H$ | $-C(=NOCOOCH_3)NH_2$ | 1 | C | — |
| 528 | $-\underset{NHCOOC_2H_5}{CHCH_2}-\text{phenyl}$ | $-H$ | $-C(=NOCOOCH_3)NH_2$ | 1 | C | — |
| 529 | $-\underset{NHSO_2CH_3}{CHCH_2}-\text{phenyl}$ | $-H$ | $-C(=NOCOOCH_3)NH_2$ | 1 | C | — |
| 530 | $-\underset{OH}{CH}-\text{phenyl}$ | $-H$ | $-C(=NOCOOCH_3)NH_2$ | 1 | C | — |
| 531 | $-\underset{NHCOOC_2H_5}{CHCH_2C(CH_3)_3}$ | $-H$ | $-C(=NOCOOCH_3)NH_2$ | 1 | C | — |
| 532 | $-\underset{NHCOOCH(CH_3)_2}{CHCH_2C(CH_3)_3}$ | $-H$ | $-C(=NOCOOCH_3)NH_2$ | 1 | C | — |
| 533 | $-\underset{NHCOOC_3H_5}{CHCH_2C(CH_3)_3}$ | $-H$ | $-C(=NOCOOCH_3)NH_2$ | 1 | C | — |
| 534 | $-\underset{OH}{CHCH_2C(CH_3)_3}$ | $-H$ | $-C(=NOCOOCH_3)NH_2$ | 1 | C | — |
| 535 | $-\underset{NHCOOC_2H_5}{CH}-\text{cyclohexyl(H)}$ | $-H$ | $-C(=NOCOOCH_3)NH_2$ | 1 | C | — |
| 536 | $-\underset{NHCOOCH(CH_3)_2}{CH}-\text{cyclohexyl(H)}$ | $-H$ | $-C(=NOCOOCH_3)NH_2$ | 1 | C | — |
| 537 | $-\underset{NHCOOC_2H_5}{CHCH_2}-\text{cyclohexyl(H)}$ | $-H$ | $-C(=NOCOOCH_3)NH_2$ | 1 | C | — |

TABLE 1-continued

[Structure: pyrrolidine with (CH2)m substituent, N-C(=O)-R1, α-carbon with C(=O)N(R2)CH2-phenyl-A-R3]

| Compound No. | -R1 $\left(\begin{array}{c}-D-(CH)_m-E-R^4\\ \| \\ R^5\end{array}\right)$ | -R2 | -R3 | n | A | Broken line |
|---|---|---|---|---|---|---|
| 538 | -CHCH2-(cyclohexyl, H) / NHCOOC(CH3)3 | -H | -C(=NOCOOCH3)NH2 | 1 | C | — |
| 539 | -CHCH2CH(CH3)2 / NHCOOC2H5 | -H | -C(=NOCOOCH3)NH2 | 1 | C | — |
| 540 | -CHCH2CH(CH3)2 / NHCOOCH(CH3)2 | -H | -C(=NOCOOCH3)NH2 | 1 | C | — |
| 541 | -CH-(cyclohexyl, H) / NHCOOC(CH3)3 | -H | -C(=NOCOOCH3)NH2 | 1 | C | Single bond |
| 542 | -CHCH2-(cyclohexyl, H) / NHCOOCH(CH3)2 | -H | -C(=NOCOOCH3)NH2 | 1 | C | Single bond |
| 543 | -CH-(cyclohexyl, H) / OH | -H | -C(=NOCOOCH3)NH2 | 1 | C | Single bond |
| 544 | -CHCH2-phenyl / NHCOOC2H5 | -H | -C(=NOCOOCH3)NH2 | 1 | C | Single bond |
| 545 | -CHCH2-phenyl / NHSO2CH3 | -H | -C(=NOCOOCH3)NH2 | 1 | C | Single bond |
| 546 | -CH-phenyl / OH | -H | -C(=NOCOOCH3)NH2 | 1 | C | Single bond |
| 547 | -CHCH2C(CH3)3 / NHCOOCH(CH3)2 | -H | -C(=NOCOOCH3)NH2 | 1 | C | Single bond |
| 548 | -CHCH2C(CH3)3 / OH | -H | -C(=NOCOOCH3)NH2 | 1 | C | Single bond |

TABLE 1-continued

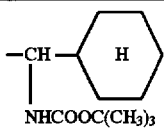

| Compound No. | -R¹ ( -D-(CH)ₘ-E-R⁴ / R⁵ ) | -R² | -R³ | n | A | Broken line |
|---|---|---|---|---|---|---|
| 549 | -CH(NHCOOC(CH₃)₃)-C₆H₁₁ | -H | -C(=NOCOOCH₃)NH₂ | 1 | C | — |
| 550 | -CHCH₂(NHCOOCH(CH₃)₂)-C₆H₁₁ | -H | -C(=NOCOOCH₃)NH₂ | 1 | C | — |
| 551 | -CH(OH)-C₆H₁₁ | -H | -C(=NOCOOCH₃)NH₂ | 1 | C | — |
| 552 | -CHCH₂(NHCOOC₂H₅)-C₆H₅ | -H | -C(=NOCOOCH₃)NH₂ | 1 | C | — |
| 553 | -CHCH₂(NHSO₂CH₃)-C₆H₅ | -H | -C(=NOCOOCH₃)NH₂ | 1 | C | — |
| 554 | -CH(OH)-C₆H₅ | -H | -C(=NOCOOCH₃)NH₂ | 1 | C | — |
| 555 | -CHCH₂C(CH₃)₃ \| NHCOOCH(CH₃)₂ | -H | -C(=NOCOOCH₃)NH₂ | 1 | C | — |
| 556 | -CHCH₂C(CH₃)₃ \| OH | -H | -C(=NOCOOCH₃)NH₂ | 1 | C | — |
| 557 | -CHCH₂(NHCOOC(CH₃)₃)-C₆H₁₁ | -H | -C(=NOCOOCH₃)NH₂ | 1 | C | — |
| 558 | -CHCH₂(NHCOOC₂H₅)-C₆H₁₁ | -H | -C(=NOCOOCH₃)NH₂ | 1 | C | — |
| 559 | -CH(NHCOOCH(CH₃)₂)-C₆H₁₁ | -H | -C(=NOCOOCH₃)NH₂ | 1 | C | — |

TABLE 1-continued

[Structure: (CH₂)ₘ-substituted pyrrolidine with N-C(=O)-R¹, connected via C(=O)-N(R²)-CH₂- to a cyclohexene/benzene ring bearing A-R³]

$$-R^1 \left( \begin{array}{c} -D-(CH)_m-E-R^4 \\ | \\ R^5 \end{array} \right)$$

| Compound No. | -R¹ | -R² | -R³ | n | A | Broken line |
|---|---|---|---|---|---|---|
| 560 | -CH(NHCOOC₂H₅)(C₆H₁₁) | -H | -C(=NOCOOCH₃)NH₂ | 1 | C | — |
| 561 | -CHCH₂C(CH₃)₃ \| NHCOOC₂H₅ | -H | -C(=NOCOOCH₃)NH₂ | 1 | C | — |
| 562 | -CHCH₂C(CH₃)₃ \| NHCOOC(CH₃)₃ | -H | -C(=NOCOOCH₃)NH₂ | 1 | C | — |
| 563 | -CHCH₂C(CH₃)₂ \| OCOOC₂H₅ | -H | -C(=NOCOOCH₃)NH₂ | 1 | C | — |
| 564 | -CHCH₂CH(CH₃)₂ \| NHCOOCH(CH₃)₂ | -H | -C(=NOCOOCH₃)NH₂ | 1 | C | — |
| 565 | -CHCH₂(C₆H₁₁) \| NHCOOC(CH₃)₃ | -H | -C(=NCH₃)NH₂ | 1 | C | Single bond |
| 566 | -CHCH₂(C₆H₁₁) \| NHSO₂CH₃ | -H | -C(=NCH₃)NH₂ | 1 | C | Single bond |
| 567 | -CH(OH)(C₆H₁₁) | -H | -C(=NCH₃)NH₂ | 1 | C | Single bond |
| 568 | -CHCH₂(C₆H₅) \| NHSO₂CH₃ | -H | -C(=NCH₃)NH₂ | 1 | C | Single bond |
| 569 | -CHCH₂C(CH₃)₃ \| NHCOOC₂H₅ | -H | -C(=NCH₃)NH₂ | 1 | C | Single bond |
| 570 | -CHCH₂C(CH₃)₃ \| NHSO₂CH₃ | -H | -C(=NCH₃)NH₂ | 1 | C | Single bond |

TABLE 1-continued

Structure: (CH₂)ₘ-pyrrolidine with N-C(=O)-R¹, α-C(=O)-N(R²)-CH₂-[aryl]-A-R³

| Compound No. | -R¹ ( -D-(CH)ₘ-E-R⁴ / R⁵ ) | -R² | -R³ | n | A | Broken line |
|---|---|---|---|---|---|---|
| 571 | -CHCH₂(cyclohexyl, H) / NHCOOC(CH₃)₃ | -H | -C(=NCH₃)NH₂ | 1 | C | — |
| 572 | -CHCH₂(cyclohexyl, H) / NHSO₂CH₃ | -H | -C(=NCH₃)NH₂ | 1 | C | — |
| 573 | -CH(cyclohexyl, H) / OH | -H | -C(=NCH₃)NH₂ | 1 | C | — |
| 574 | -CHCH₂(phenyl) / NHSO₂CH₃ | -H | -C(=NCH₃)NH₂ | 1 | C | — |
| 575 | -CHCH₂C(CH₃)₃ / NHCOOC₂H₅ | -H | -C(=NCH₃)NH₂ | 1 | C | — |
| 576 | -CHCH₂C(CH₃)₃ / NHSO₂CH₃ | -H | -C(=NCH₃)NH₂ | 1 | C | — |
| 577 | -CHCH₂(cyclohexyl, H) / NHCOOC(CH₃)₃ | -H | -C(=NCOCH₃)NH₂ | 1 | C | Single bond |
| 578 | -CHCH₂(cyclohexyl, H) / NHSO₂CH₃ | -H | -C(=NCOCH₃)NH₂ | 1 | C | Single bond |
| 579 | -CH(cyclohexyl, H) / OH | -H | -C(=NCOCH₃)NH₂ | 1 | C | Single bond |
| 580 | -CHCH₂(phenyl) / NHSO₂CH₃ | -H | -C(=NCOCH₃)NH₂ | 1 | C | Single bond |
| 581 | -CHCH₂C(CH₃)₃ / NHCOOC₂H₅ | -H | -C(=NCOCH₃)NH₂ | 1 | C | Single bond |

TABLE 1-continued

[Structure at top of table: pyrrolidine ring with (CH2)m, N-C(=O)-R1, connected to CH-C(=O)-N(R2)-CH2-phenyl-A-R3]

| Compound No. | -R1 (-D-(CH)m-E-R4 with R5) | -R2 | -R3 | n | A | Broken line |
|---|---|---|---|---|---|---|
| 582 | -CHCH2C(CH3)3, NHSO2CH3 | -H | -C(=NCOCH3)NH2 | 1 | C | Single bond |
| 583 | -CHCH2-C6H11(H), NHCOOC(CH3)3 | -H | -C(=NCOCH3)NH2 | 1 | C | — |
| 584 | -CHCH2-C6H11(H), NHSO2CH3 | -H | -C(=NCOCH3)NH2 | 1 | C | — |
| 585 | -CH(OH)-C6H11(H) | -H | -C(=NCOCH3)NH2 | 1 | C | — |
| 586 | -CHCH2-C6H5, NHSO2CH3 | -H | -C(=NCOCH3)NH2 | 1 | C | — |
| 587 | -CHCH2C(CH3)3, NHCOOC2H5 | -H | -C(=NCOCH3)NH2 | 1 | C | — |
| 588 | -CHCH2C(CH3)3, NHSO2CH3 | -H | -C(=NCOCH3)NH2 | 1 | C | — |
| 589 | -CHCH2-C6H11(H), NHCOOC(CH3)3 | -H | -C(=NCOCH3)NH2 | 1 | C | Single bond |
| 590 | -CHCH2-C6H11(H), NHSO2CH3 | -H | -C(=NCOCH3)NH2 | 1 | C | Single bond |
| 591 | -CH(OH)-C6H11(H) | -H | -C(=NCOCH3)NH2 | 1 | C | Single bond |
| 592 | -CHCH2-C6H5, NHSO2CH3 | -H | -C(=NCOCH3)NH2 | 1 | C | Single bond |

TABLE 1-continued

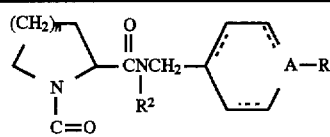

| Compound No. | $-R^1 \left( \begin{array}{c} -D-(CH)_m-E-R^4 \\ \| \\ R^5 \end{array} \right)$ | $-R^2$ | $-R^3$ | n | A | Broken line |
|---|---|---|---|---|---|---|
| 593 | -CHCH$_2$C(CH$_3$)$_3$<br>\|<br>NHCOOC$_2$H$_5$ | -H | -C(=NCOCH$_3$)NH$_2$ | 1 | C | Single bond |
| 594 | -CHCH$_2$C(CH$_3$)$_3$<br>\|<br>NHSO$_2$CH$_3$ | -H | -C(=NCOCH$_3$)NH$_2$ | 1 | C | Single bond |
| 595 | -CHCH$_2$-C$_6$H$_{11}$<br>\|<br>NHCOOC(CH$_3$)$_3$ | -H | -C(=NCOCH$_3$)NH$_2$ | 1 | C | — |
| 596 | -CHCH$_2$-C$_6$H$_{11}$<br>\|<br>NHSO$_2$CH$_3$ | -H | -C(=NCOCH$_3$)NH$_2$ | 1 | C | — |
| 597 | -CH(OH)-C$_6$H$_{11}$ | -H | -C(=NCOCH$_3$)NH$_2$ | 1 | C | — |
| 598 | -CHCH$_2$-C$_6$H$_5$<br>\|<br>NHSO$_2$CH$_3$ | -H | -C(=NCOCH$_3$)NH$_2$ | 1 | C | — |
| 599 | -CHCH$_2$C(CH$_3$)$_3$<br>\|<br>NHCOOC$_2$H$_5$ | -H | -C(=NCOCH$_3$)NH$_2$ | 1 | C | — |
| 600 | -CHCH$_2$C(CH$_3$)$_3$<br>\|<br>NHSO$_2$CH$_3$ | -H | -C(=NCOCH$_3$)NH$_2$ | 1 | C | — |
| 601 | -CHCH$_2$-C$_6$H$_{11}$<br>\|<br>NHCOOC(CH$_3$)$_3$ | -H | -C(=NCOCH$_3$)NH$_2$ | 1 | C | Single bond |
| 602 | -CHCH$_2$-C$_6$H$_{11}$<br>\|<br>NHSO$_2$CH$_3$ | -H | -C(=NCOCH$_3$)NH$_2$ | 1 | C | Single bond |
| 603 | -CH(OH)-C$_6$H$_{11}$ | -H | -C(=NCOCH$_3$)NH$_2$ | 1 | C | Single bond |

TABLE 1-continued

| Compound No. | $-R^1 \left( \begin{array}{c} -D-(CH)_m-E-R^4 \\ R^5 \end{array} \right)$ | $-R^2$ | $-R^3$ | n | A | Broken line |
|---|---|---|---|---|---|---|
| 604 | -CHCH₂-C₆H₅ <br> \|  <br> NHSO₂CH₃ | -H | -C(=NCOCH₃)NH₂ | 1 | C | Single bond |
| 605 | -CHCH₂C(CH₃)₃ <br> \| <br> NHCOOC₂H₅ | -H | -C(=NCOCH₃)NH₂ | 1 | C | Single bond |
| 606 | -CHCH₂C(CH₃)₃ <br> \| <br> NHSO₂CH₃ | -H | -C(=NCOCH₃)NH₂ | 1 | C | Single bond |
| 607 | -CHCH₂-C₆H₁₁ <br> \| <br> NHCOOC(CH₃)₃ | -H | -C(=NCOCH₃)NH₂ | 1 | C | — |
| 608 | -CHCH₂-C₆H₁₁ <br> \| <br> NHSO₂CH₃ | -H | -C(=NCOCH₃)NH₂ | 1 | C | — |
| 609 | -CH-C₆H₁₁ <br> \| <br> OH | -H | -C(=NCOCH₃)NH₂ | 1 | C | — |
| 610 | -CHCH₂-C₆H₅ <br> \| <br> NHSO₂CH₃ | -H | -C(=NCOCH₃)NH₂ | 1 | C | — |
| 611 | -CHCH₂C(CH₃)₃ <br> \| <br> NHCOOC₂H₅ | -H | -C(=NCOCH₃)NH₂ | 1 | C | — |
| 612 | -CHCH₂C(CH₃)₃ <br> \| <br> NHSO₂CH₃ | -H | -C(=NCOCH₃)NH₂ | 1 | C | — |
| 613 | -CHCH₂-C₆H₁₁ <br> \| <br> NHCOOC(CH₃)₃ | -H | -C(=NOCH₃)NH₂ | 1 | C | Single bond |
| 614 | -CHCH₂-C₆H₁₁ <br> \| <br> NHSO₂CH₃ | -H | -C(=NOCH₃)NH₂ | 1 | C | Single bond |

TABLE 1-continued

| Compound No. | $-R^1 \left( \begin{array}{c} -D-(CH)_m-E-R^4 \\ R^5 \end{array} \right)$ | $-R^2$ | $-R^3$ | n | A | Broken line |
|---|---|---|---|---|---|---|
| 615 | -CH(OH)-C₆H₁₁ | -H | -C(=NOCH₃)NH₂ | 1 | C | Single bond |
| 616 | -CHCH₂-C₆H₅ with NHSO₂CH₃ | -H | -C(=NOCH₃)NH₂ | 1 | C | Single bond |
| 617 | -CHCH₂C(CH₃)₃ with NHCOOC₂H₅ | -H | -C(=NOCH₃)NH₂ | 1 | C | Single bond |
| 618 | -CHCH₂C(CH₃)₃ with NHSO₂CH₃ | -H | -C(=NOCH₃)NH₂ | 1 | C | Single bond |
| 619 | -CHCH₂-C₆H₁₁ with NHCOOC(CH₃)₃ | -H | -C(=NOCH₃)NH₂ | 1 | C | — |
| 620 | -CHCH₂-C₆H₁₁ with NHSO₂CH₃ | -H | -C(=NOCH₃)NH₂ | 1 | C | — |
| 621 | -CH(OH)-C₆H₁₁ | -H | -C(=NOCH₃)NH₂ | 1 | C | — |
| 622 | -CHCH₂-C₆H₅ with NHSO₂CH₃ | -H | -C(=NOCH₃)NH₂ | 1 | C | — |
| 623 | -CHCH₂C(CH₃)₃ with NHCOOC₂H₅ | -H | -C(=NOCH₃)NH₂ | 1 | C | — |
| 624 | -CHCH₂C(CH₃)₃ with NHSO₂CH₃ | -H | -C(=NOCH₃)NH₂ | 1 | C | — |
| 625 | -CHCH₂-C₆H₁₁ with NHCOOC(CH₃)₃ | -H | -C(=NOCOCH₂OH)NH₂ | 1 | C | Single bond |

TABLE 1-continued

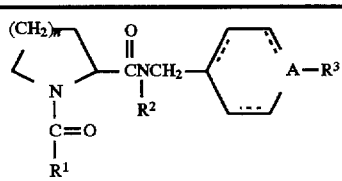

| Compound No. | $-R^1$ $\left(\begin{array}{c}-D-(CH)_m-E-R^4\\ R^5\end{array}\right)$ | $-R^2$ | $-R^3$ | n | A | Broken line |
|---|---|---|---|---|---|---|
| 626 | −CHCH₂−⟨H⟩<br>\|<br>NHSO₂CH₃ | −H | −C(=NOCOCH₂OH)NH₂ | 1 | C | Single bond |
| 627 | −CH−⟨H⟩<br>\|<br>OH | −H | −C(=NOCOCH₂OH)NH₂ | 1 | C | Single bond |
| 628 | −CHCH₂−Ph<br>\|<br>NHSO₂CH₃ | −H | −C(=NOCOCH₂OH)NH₂ | 1 | C | Single bond |
| 629 | −CHCH₂C(CH₃)₃<br>\|<br>NHCOOC₂H₅ | −H | −C(=NOCOCH₂OH)NH₂ | 1 | C | Single bond |
| 630 | −CHCH₂C(CH₃)₃<br>\|<br>NHSO₂CH₃ | −H | −C(=NOCOCH₂OH)NH₂ | 1 | C | Single bond |
| 631 | −CHCH₂−⟨H⟩<br>\|<br>NHCOOC(CH₃)₃ | −H | −C(=NOCOCH₂OH)NH₂ | 1 | C | — |
| 632 | −CHCH₂−⟨H⟩<br>\|<br>NHSO₂CH₃ | −H | −C(=NOCOCH₂OH)NH₂ | 1 | C | — |
| 633 | −CH−⟨H⟩<br>\|<br>OH | −H | −C(=NOCOCH₂OH)NH₂ | 1 | C | — |
| 634 | −CHCH₂−Ph<br>\|<br>NHSO₂CH₃ | −H | −C(=NOCOCH₂OH)NH₂ | 1 | C | — |
| 635 | −CHCH₂C(CH₃)₃<br>\|<br>NHCOOC₂H₅ | −H | −C(=NOCOCH₂OH)NH₂ | 1 | C | — |
| 636 | −CHCH₂C(CH₃)₃<br>\|<br>NHSO₂CH₃ | −H | −C(=NOCOCH₂OH)NH₂ | 1 | C | — |

TABLE 1-continued

Structure:
$$\text{pyrrolidine with } (CH_2)_n, \ N\text{-}C(=O)\text{-}R^1, \ \alpha\text{-}C(R^2)\text{-}C(=O)\text{-}NCH_2\text{-}\text{Ar}\text{-}A\text{-}R^3$$

| Compound No. | $-R^1 \left( \begin{array}{c} -D-(CH)_m-E-R^4 \\ R^5 \end{array} \right)$ | $-R^2$ | $-R^3$ | n | A | Broken line |
|---|---|---|---|---|---|---|
| 637 | $-CHCH_2-\text{(cyclohexyl, H)}$, NHCOOC(CH$_3$)$_3$ | $-H$ | $-NHC(=NH)NH_2$ | 1 | C | Single bond |
| 638 | $-CHCH_2-\text{(cyclohexyl, H)}$, NHSO$_2$CH$_3$ | $-H$ | $-NHC(=NH)NH_2$ | 1 | C | Single bond |
| 639 | $-CH(\text{cyclohexyl, H})$, OH | $-H$ | $-NHC(=NH)NH_2$ | 1 | C | Single bond |
| 640 | $-CHCH_2-\text{phenyl}$, NHSO$_2$CH$_3$ | $-H$ | $-NHC(=NH)NH_2$ | 1 | C | Single bond |
| 641 | $-CHCH_2C(CH_3)_3$, NHCOOC$_2$H$_5$ | $-H$ | $-NHC(=NH)NH_2$ | 1 | C | Single bond |
| 642 | $-CHCH_2C(CH_3)_3$, NHSO$_2$CH$_3$ | $-H$ | $-NHC(=NH)NH_2$ | 1 | C | Single bond |
| 643 | $-CHCH_2-\text{(cyclohexyl, H)}$, NHCOOC(CH$_3$)$_3$ | $-H$ | $-NHC(=NH)NH_2$ | 1 | C | — |
| 644 | $-CHCH_2-\text{(cyclohexyl, H)}$, NHSO$_2$CH$_3$ | $-H$ | $-NHC(=NH)NH_2$ | 1 | C | — |
| 645 | $-CH(\text{cyclohexyl, H})$, OH | $-H$ | $-NHC(=NH)NH_2$ | 1 | C | — |
| 646 | $-CHCH_2-\text{phenyl}$, NHSO$_2$CH$_3$ | $-H$ | $-NHC(=NH)NH_2$ | 1 | C | — |
| 647 | $-CHCH_2C(CH_3)_3$, NHCOOC$_2$H$_5$ | $-H$ | $-NHC(=NH)NH_2$ | 1 | C | — |

TABLE 1-continued

Structure:
$$\text{pyrrolidine-(CH}_2)_n\text{-CH(NC(=O)R}^1\text{)-C(=O)-NR}^2\text{-CH}_2\text{-C}_6\text{H}_4\text{-A-R}^3$$

| Compound No. | $-R^1$ $\left(-D-\underset{R^5}{(CH)_m}-E-R^4\right)$ | $-R^2$ | $-R^3$ | n | A | Broken line |
|---|---|---|---|---|---|---|
| 648 | $-\underset{NHSO_2CH_3}{CHCH_2C(CH_3)_3}$ | $-H$ | $-NHC(=NH)NH_2$ | 1 | C | — |
| 649 | $-\underset{NHCOOC(CH_3)_3}{CHCH_2}-$cyclohexyl(H) | $-H$ | $-NHC(=NCH_3)NH_2$ | 1 | C | Single bond |
| 650 | $-\underset{NHSO_2CH_3}{CHCH_2}-$cyclohexyl(H) | $-H$ | $-NHC(=NCH_3)NH_2$ | 1 | C | Single bond |
| 651 | $-\underset{OH}{CH}-$cyclohexyl(H) | $-H$ | $-NHC(=NCH_3)NH_2$ | 1 | C | Single bond |
| 652 | $-\underset{NHSO_2CH_3}{CHCH_2}-$phenyl | $-H$ | $-NHC(=NCH_3)NH_2$ | 1 | C | Single bond |
| 653 | $-\underset{NHCOOC_2H_5}{CHCH_2C(CH_3)_3}$ | $-H$ | $-NHC(=NCH_3)NH_2$ | 1 | C | Single bond |
| 654 | $-\underset{NHSO_2CH_3}{CHCH_2C(CH_3)_3}$ | $-H$ | $-NHC(=NCH_3)NH_2$ | 1 | C | Single bond |
| 655 | $-\underset{NHCOOC(CH_3)_3}{CHCH_2}-$cyclohexyl(H) | $-H$ | $-NHC(=NCH_3)NH_2$ | 1 | C | — |
| 656 | $-\underset{NHSO_2CH_3}{CHCH_2}-$cyclohexyl(H) | $-H$ | $-NHC(=NCH_3)NH_2$ | 1 | C | — |
| 657 | $-\underset{OH}{CH}-$cyclohexyl(H) | $-H$ | $-NHC(=NCH_3)NH_2$ | 1 | C | — |
| 658 | $-\underset{NHSO_2CH_3}{CHCH_2}-$phenyl | $-H$ | $-NHC(=NCH_3)NH_2$ | 1 | C | — |

TABLE 1-continued

| Compound No. | $-R^1 \left( \begin{array}{c} -D-(CH)_m-E-R^4 \\ \vert \\ R^5 \end{array} \right)$ | $-R^2$ | $-R^3$ | n | A | Broken line |
|---|---|---|---|---|---|---|
| 659 | -CHCH₂C(CH₃)₃<br>\|<br>NHCOOC₂H₅ | -H | -NHC(=NCH₃)NH₂ | 1 | C | — |
| 660 | -CHCH₂C(CH₃)₃<br>\|<br>NHSO₂CH₃ | -H | -NHC(=NCH₃)NH₂ | 1 | C | — |
| 661 | -CHCH₂-(cyclohexyl, H)<br>\|<br>NHCOOC(CH₃)₃ | -H | -NHC(=NCOCH₃)NH₂ | 1 | C | Single bond |
| 662 | -CHCH₂-(cyclohexyl, H)<br>\|<br>NHSO₂CH₃ | -H | -NHC(=NCOCH₃)NH₂ | 1 | C | Single bond |
| 663 | -CH-(cyclohexyl, H)<br>\|<br>OH | -H | -NHC(=NCOCH₃)NH₂ | 1 | C | Single bond |
| 664 | -CHCH₂-(phenyl)<br>\|<br>NHSO₂CH₃ | -H | -NHC(=NCOCH₃)NH₂ | 1 | C | Single bond |
| 665 | -CHCH₂C(CH₃)₃<br>\|<br>NHCOOC₂H₅ | -H | -NHC(=NCOCH₃)NH₂ | 1 | C | Single bond |
| 666 | -CHCH₂C(CH₃)₃<br>\|<br>NHSO₂CH₃ | -H | -NHC(=NCOCH₃)NH₂ | 1 | C | Single bond |
| 667 | -CHCH₂-(cyclohexyl, H)<br>\|<br>NHCOOC(CH₃)₃ | -H | -NHC(=NCOCH₃)NH₂ | 1 | C | — |
| 668 | -CHCH₂-(cyclohexyl, H)<br>\|<br>NHSO₂CH₃ | -H | -NHC(=NCOCH₃)NH₂ | 1 | C | — |
| 669 | -CH-(cyclohexyl, H)<br>\|<br>OH | -H | -NHC(=NCOCH₃)NH₂ | 1 | C | — |

TABLE 1-continued

| Compound No. | —R¹ ( —D—(CH)ₘ—E—R⁴ / R⁵ ) | —R² | —R³ | n | A | Broken line |
|---|---|---|---|---|---|---|
| 670 | —CHCH₂—C₆H₅ / NHSO₂CH₃ | —H | —NHC(=NCOCH₃)NH₂ | 1 | C | — |
| 671 | —CHCH₂C(CH₃)₃ / NHCOOC₂H₅ | —H | —NHC(=NCOCH₃)NH₂ | 1 | C | — |
| 672 | —CHCH₂C(CH₃)₃ / NHSO₂CH₃ | —H | —NHC(=NCOCH₃)NH₂ | 1 | C | — |
| 673 | —CHCH₂—C₆H₁₁(H) / NHCOOC(CH₃)₃ | —H | —NHC(=NOCOCH₃)NH₂ | 1 | C | Single bond |
| 674 | —CHCH₂—C₆H₁₁(H) / NHSO₂CH₃ | —H | —NHC(=NOCOCH₃)NH₂ | 1 | C | Single bond |
| 675 | —CH—C₆H₁₁(H) / OH | —H | —NHC(=NOCOCH₃)NH₂ | 1 | C | Single bond |
| 676 | —CHCH₂—C₆H₅ / NHSO₂CH₃ | —H | —NHC(=NOCOCH₃)NH₂ | 1 | C | Single bond |
| 677 | —CHCH₂C(CH₃)₃ / NHCOOC₂H₅ | —H | —NHC(=NOCOCH₃)NH₂ | 1 | C | Single bond |
| 678 | —CHCH₂C(CH₃)₃ / NHSO₂CH₃ | —H | —NHC(=NOCOCH₃)NH₂ | 1 | C | Single bond |
| 679 | —CHCH₂—C₆H₁₁(H) / NHCOOC(CH₃)₃ | —H | —NHC(=NOCOCH₃)NH₂ | 1 | C | — |
| 680 | —CHCH₂—C₆H₁₁(H) / NHSO₂CH₃ | —H | —NHC(=NOCOCH₃)NH₂ | 1 | C | — |

TABLE 1-continued

| Compound No. | $-R^1 \left( \begin{array}{c} -D-(CH)_m-E-R^4 \\ R^5 \end{array} \right)$ | $-R^2$ | $-R^3$ | n | A | Broken line |
|---|---|---|---|---|---|---|
| 681 | -CH(OH)(C6H11) | -H | -NHC(=NOCOCH3)NH2 | 1 | C | — |
| 682 | -CHCH2(C6H5), NHSO2CH3 | -H | -NHC(=NOCOCH3)NH2 | 1 | C | — |
| 683 | -CHCH2C(CH3)3, NHCOOC2H5 | -H | -NHC(=NOCOCH3)NH2 | 1 | C | — |
| 684 | -CHCH2C(CH3)3, NHSO2CH3 | -H | -NHC(=NOCOCH3)NH2 | 1 | C | — |
| 685 | -CHCH2(C6H11), NHCOOC(CH3)3 | -H | -NHC(=NOCH3)NH2 | 1 | C | Single bond |
| 686 | -CHCH2(C6H11), NHSO2CH3 | -H | -NHC(=NOCH3)NH2 | 1 | C | Single bond |
| 687 | -CH(OH)(C6H11) | -H | -NHC(=NOCH3)NH2 | 1 | C | Single bond |
| 688 | -CHCH2(C6H5), NHSO2CH3 | -H | -NHC(=NOCH3)NH2 | 1 | C | Single bond |
| 689 | -CHCH2C(CH3)3, NHCOOC2H5 | -H | -NHC(=NOCH3)NH2 | 1 | C | Single bond |
| 690 | -CHCH2C(CH3)3, NHSO2CH3 | -H | -NHC(=NOCH3)NH2 | 1 | C | Single bond |
| 691 | -CHCH2(C6H11), NHCOOC(CH3)3 | -H | -NHC(=NOCH3)NH2 | 1 | C | — |

TABLE 1-continued

| Compound No. | $-R^1 \left( \begin{array}{c} -D-(CH)_m-E-R^4 \\ R^5 \end{array} \right)$ | $-R^2$ | $-R^3$ | n | A | Broken line |
|---|---|---|---|---|---|---|
| 692 | —CHCH$_2$—(C$_6$H$_{11}$)<br>\|<br>NHSO$_2$CH$_3$ | —H | —NHC(=NOCH$_3$)NH$_2$ | 1 | C | — |
| 693 | —CH(OH)—(C$_6$H$_{11}$) | —H | —NHC(=NOCH$_3$)NH$_2$ | 1 | C | — |
| 694 | —CHCH$_2$—(C$_6$H$_5$)<br>\|<br>NHSO$_2$CH$_3$ | —H | —NHC(=NOCH$_3$)NH$_2$ | 1 | C | — |
| 695 | —CHCH$_2$C(CH$_3$)$_3$<br>\|<br>NHCOOC$_2$H$_5$ | —H | —NHC(=NOCH$_3$)NH$_2$ | 1 | C | — |
| 696 | —CHCH$_2$C(CH$_3$)$_3$<br>\|<br>NHSO$_2$CH$_3$ | —H | —NHC(=NOCH$_3$)NH$_2$ | 1 | C | — |
| 697 | —CHCH$_2$—(C$_6$H$_{11}$)<br>\|<br>NHCOOC(CH$_3$)$_3$ | —H | —NHC(=NCOOCH$_3$)NH$_2$ | 1 | C | Single bond |
| 698 | —CHCH$_2$—(C$_6$H$_{11}$)<br>\|<br>NHSO$_2$CH$_3$ | —H | —NHC(=NCOOCH$_3$)NH$_2$ | 1 | C | Single bond |
| 699 | —CH(OH)—(C$_6$H$_{11}$) | —H | —NHC(=NCOOCH$_3$)NH$_2$ | 1 | C | Single bond |
| 700 | —CHCH$_2$—(C$_6$H$_5$)<br>\|<br>NHSO$_2$CH$_3$ | —H | —NHC(=NCOOCH$_3$)NH$_2$ | 1 | C | Single bond |
| 701 | —CHCH$_2$C(CH$_3$)$_3$<br>\|<br>NHCOOC$_2$H$_5$ | —H | —NHC(=NCOOCH$_3$)NH$_2$ | 1 | C | Single bond |
| 702 | —CHCH$_2$C(CH$_3$)$_3$<br>\|<br>NHSO$_2$CH$_3$ | —H | —NHC(=NCOOCH$_3$)NH$_2$ | 1 | C | Single bond |

TABLE 1-continued

[Structure: pyrrolidine ring with (CH₂)ₙ, N-C(=O)-R¹, and -C(=O)-N(R²)-CH₂-[ring]-A-R³]

| Compound No. | -R¹ (-D-(CH)ₘ-E-R⁴ / R⁵) | -R² | -R³ | n | A | Broken line |
|---|---|---|---|---|---|---|
| 703 | -CHCH₂-(cyclohexyl, H) / NHCOOC(CH₃)₃ | -H | -NHC(=NCOOCH₃)NH₂ | 1 | C | — |
| 704 | -CHCH₂-(cyclohexyl, H) / NHSO₂CH₃ | -H | -NHC(=NCOOCH₃)NH₂ | 1 | C | — |
| 705 | -CH(OH)-(cyclohexyl, H) | -H | -NHC(=NCOOCH₃)NH₂ | 1 | C | — |
| 706 | -CHCH₂-(phenyl) / NHSO₂CH₃ | -H | -NHC(=NCOOCH₃)NH₂ | 1 | C | — |
| 707 | -CHCH₂C(CH₃)₃ / NHCOOC₂H₅ | -H | -NHC(=NCOOCH₃)NH₂ | 1 | C | — |
| 708 | -CHCH₂C(CH₃)₃ / NHSO₂CH₃ | -H | -NHC(=NCOOCH₃)NH₂ | 1 | C | — |
| 709 | -CHCH₂-(cyclohexyl, H) / NHCOOC(CH₃)₃ | -H | -NHC(=NCOOCH₃)NH₂ | 1 | C | Single bond |
| 710 | -CHCH₂-(cyclohexyl, H) / NHSO₂CH₃ | -H | -NHC(=NCOOCH₃)NH₂ | 1 | C | Single bond |
| 711 | -CH(OH)-(cyclohexyl, H) | -H | -NHC(=NCOOCH₃)NH₂ | 1 | C | Single bond |
| 712 | -CHCH₂-(phenyl) / NHSO₂CH₃ | -H | -NHC(=NCOOCH₃)NH₂ | 1 | C | Single bond |
| 713 | -CHCH₂C(CH₃)₃ / NHCOOC₂H₅ | -H | -NHC(=NCOOCH₃)NH₂ | 1 | C | Single bond |

TABLE 1-continued

| Compound No. | $-R^1$ $\left(\begin{array}{c}-D-(CH)_m-E-R^4\\ \mid \\ R^5\end{array}\right)$ | $-R^2$ | $-R^3$ | n | A | Broken line |
|---|---|---|---|---|---|---|
| 714 | —CHCH$_2$C(CH$_3$)$_3$<br>\|<br>NHSO$_2$CH$_3$ | —H | —NHC(=NCOOCH$_3$)NH$_2$ | 1 | C | Single bond |
| 715 | —CHCH$_2$—(C$_6$H$_{11}$)<br>\|<br>NHCOOC(CH$_3$)$_3$ | —H | —NHC(=NCOOCH$_3$)NH$_2$ | 1 | C | — |
| 716 | —CHCH$_2$—(C$_6$H$_{11}$)<br>\|<br>NHSO$_2$CH$_3$ | —H | —NHC(=NCOOCH$_3$)NH$_2$ | 1 | C | — |
| 717 | —CH—(C$_6$H$_{11}$)<br>\|<br>OH | —H | —NHC(=NCOOCH$_3$)NH$_2$ | 1 | C | — |
| 718 | —CHCH$_2$—(C$_6$H$_5$)<br>\|<br>NHSO$_2$CH$_3$ | —H | —NHC(=NCOOCH$_3$)NH$_2$ | 1 | C | — |
| 719 | —CHCH$_2$C(CH$_3$)$_3$<br>\|<br>NHCOOC$_2$H$_5$ | —H | —NHC(=NCOOCH$_3$)NH$_2$ | 1 | C | — |
| 720 | —CHCH$_2$C(CH$_3$)$_3$<br>\|<br>NHSO$_2$CH$_3$ | —H | —NHC(=NCOOCH$_3$)NH$_2$ | 1 | C | — |
| 721 | —CHCH$_2$—(C$_6$H$_{11}$)<br>\|<br>NHCOOC(CH$_3$)$_3$ | —H | —NHC(=NOH)NH$_2$ | 1 | C | Single bond |
| 722 | —CHCH$_2$—(C$_6$H$_{11}$)<br>\|<br>NHSO$_2$CH$_3$ | —H | —NHC(=NOH)NH$_2$ | 1 | C | Single bond |
| 723 | —CH—(C$_6$H$_{11}$)<br>\|<br>OH | —H | —NHC(=NOH)NH$_2$ | 1 | C | Single bond |
| 724 | —CHCH$_2$—(C$_6$H$_5$)<br>\|<br>NHSO$_2$CH$_3$ | —H | —NHC(=NOH)NH$_2$ | 1 | C | Single bond |

TABLE 1-continued

| Compound No. | -R¹ ( -D-(CH)ₘ-E-R⁴ / R⁵ ) | -R² | -R³ | n | A | Broken line |
|---|---|---|---|---|---|---|
| 725 | -CHCH₂C(CH₃)₃ \| NHCOOC₂H₅ | -H | -NHC(=NOH)NH₂ | 1 | C | Single bond |
| 726 | -CHCH₂C(CH₃)₃ \| NHSO₂CH₃ | -H | -NHC(=NOH)NH₂ | 1 | C | Single bond |
| 727 | -CHCH₂-(C₆H₁₁) \| NHCOOC(CH₃)₃ | -H | -NHC(=NOH)NH₂ | 1 | C | — |
| 728 | -CHCH₂-(C₆H₁₁) \| NHSO₂CH₃ | -H | -NHC(=NOH)NH₂ | 1 | C | — |
| 729 | -CH-(C₆H₁₁) \| OH | -H | -NHC(=NOH)NH₂ | 1 | C | — |
| 730 | -CHCH₂-Ph \| NHSO₂CH₃ | -H | -NHC(=NOH)NH₂ | 1 | C | — |
| 731 | -CHCH₂C(CH₃)₃ \| NHCOOC₂H₅ | -H | -NHC(=NOH)NH₂ | 1 | C | — |
| 732 | -CHCH₂C(CH₃)₃ \| NHSO₂CH₃ | -H | -NHC(=NOH)NH₂ | 1 | C | — |
| 733 | -CHCH₂-(C₆H₁₁) \| NHCOOC(CH₃)₃ | -H | -NHC(=NOCOCH₂OH)NH₂ | 1 | C | Single bond |
| 734 | -CHCH₂-(C₆H₁₁) \| NHSO₂CH₃ | -H | -NHC(=NOCOCH₂OH)NH₂ | 1 | C | Single bond |
| 735 | -CH-(C₆H₁₁) \| OH | -H | -NHC(=NOCOCH₂OH)NH₂ | 1 | C | Single bond |

TABLE 1-continued

| Compound No. | −R¹ ( −D−(CH)ₘ−E−R⁴ / R⁵ ) | −R² | −R³ | n | A | Broken line |
|---|---|---|---|---|---|---|
| 736 | −CHCH₂−C₆H₅ / NHSO₂CH₃ | −H | −NHC(=NOCOCH₂OH)NH₂ | 1 | C | Single bond |
| 737 | −CHCH₂C(CH₃)₃ / NHCOOC₂H₅ | −H | −NHC(=NOCOCH₂OH)NH₂ | 1 | C | Single bond |
| 738 | −CHCH₂C(CH₃)₃ / NHSO₂CH₃ | −H | −NHC(=NOCOCH₂OH)NH₂ | 1 | C | Single bond |
| 739 | −CHCH₂−C₆H₁₁ / NHCOOC(CH₃)₃ | −H | −NHC(=NOCOCH₂OH)NH₂ | 1 | C | — |
| 740 | −CHCH₂−C₆H₁₁ / NHSO₂CH₃ | −H | −NHC(=NOCOCH₂OH)NH₂ | 1 | C | — |
| 741 | −CH−C₆H₁₁ / OH | −H | −NHC(=NOCOCH₂OH)NH₂ | 1 | C | — |
| 742 | −CHCH₂−C₆H₅ / NHSO₂CH₃ | −H | −NHC(=NOCOCH₂OH)NH₂ | 1 | C | — |
| 743 | −CHCH₂C(CH₃)₃ / NHCOOC₂H₅ | −H | −NHC(=NOCOCH₂OH)NH₂ | 1 | C | — |
| 744 | −CHCH₂C(CH₃)₃ / NHSO₂CH₃ | −H | −NHC(=NOCOCH₂OH)NH₂ | 1 | C | — |
| 745 | −CH−C₆H₁₁ / NHSO₂CH₃ | −H | −NH₂ | 1 | C | Single bond |
| 746 | −CHCH₂−C₆H₁₁ / NHSO₂CH₃ | −H | −NH₂ | 1 | C | Single bond |

TABLE 1-continued

[Structure at top of table:
(CH₂)ₙ attached to a pyrrolidine ring with N-C(=O)-R¹, with position bearing -C(=O)-N(R²)-CH₂-[ring]-A-R³]

| Compound No. | -R¹ ( -D-(CH)ₘ-E-R⁴ / R⁵ ) | -R² | -R³ | n | A | Broken line |
|---|---|---|---|---|---|---|
| 747 | -CHCH₂-(cyclohexyl-H) / NHCOOC₂H₅ | -H | -NH₂ | 1 | C | Single bond |
| 748 | -CHCH₂-(cyclohexyl-H) / NHCOOCH(CH₃)₂ | -H | -NH₂ | 1 | C | Single bond |
| 749 | -CHCH₂-(cyclohexyl-H) / NHCOOC(CH₃)₃ | -H | -NH₂ | 1 | C | Single bond |
| 750 | -CH-(cyclohexyl-H) / OH | -H | -NH₂ | 1 | C | Single bond |
| 751 | -CHCH₂-(phenyl) / NHSO₂CH₃ | -H | -NH₂ | 1 | C | Single bond |
| 752 | -CHCH₂-(phenyl) / NHCOOC₂H₅ | -H | -NH₂ | 1 | C | Single bond |
| 753 | -CHCH₂-(phenyl) / NHCOOCH(CH₃)₂ | -H | -NH₂ | 1 | C | Single bond |
| 754 | -CHCH₂-(phenyl) / NHCOOC(CH₃)₃ | -H | -NH₂ | 1 | C | Single bond |
| 755 | -CHCH₂-(phenyl) / OCOOC₂H₅ | -H | -NH₂ | 1 | C | Single bond |
| 756 | -CH-(cyclohexyl-H) / OH | -H | -NH₂ | 1 | C | Single bond |
| 757 | -CHCH₂C(CH₃)₃ / NHCOOC₂H₅ | -H | -NH₂ | 1 | C | Single bond |

TABLE 1-continued

[Structure: (CH₂)ₙ-pyrrolidine with N-C(=O)-R¹, connected via C(=O)-NCH₂(R²) to phenyl-A-R³]

| Compound No. | -R¹ ( -D-(CH)ₘ-E-R⁴ with R⁵ ) | -R² | -R³ | n | A | Broken line |
|---|---|---|---|---|---|---|
| 758 | -CHCH₂C(CH₃)₃ / NHCOOCH(CH₃)₂ | -H | -NH₂ | 1 | C | Single bond |
| 759 | -CH-(C₆H₁₁) / NHSO₂CH₃ | -H | -NH₂ | 1 | C | — |
| 760 | -CHCH₂-(C₆H₁₁) / NHSO₂CH₃ | -H | -NH₂ | 1 | C | — |
| 761 | -CHCH₂-(C₆H₁₁) / NHCOOC₂H₅ | -H | -NH₂ | 1 | C | — |
| 762 | -CH-(C₆H₁₁) / NHCOOCH(CH₃)₂ | -H | -NH₂ | 1 | C | — |
| 763 | -CHCH₂-(C₆H₁₁) / NHCOOCH(CH₃)₂ | -H | -NH₂ | 1 | C | — |
| 764 | -CH-(C₆H₁₁) / NHCOOC(CH₃)₃ | -H | -NH₂ | 1 | C | — |
| 765 | -CHCH₂-(C₆H₁₁) / NHCOOC(CH₃)₃ | -H | -NH₂ | 1 | C | — |
| 766 | -CH-(C₅H₉) / NHCOOCH(CH₃)₂ | -H | -NH₂ | 1 | C | — |
| 767 | -CH-(C₅H₉) / NHCOOC(CH₃)₃ | -H | -NH₂ | 1 | C | — |
| 768 | -CH-(C₆H₁₁) / OH | -H | -NH₂ | 1 | C | — |

TABLE 1-continued

[Structure at top of table showing core scaffold with (CH₂)ₙ, carbonyl, CNCH₂ bridge, R², aromatic ring with A—R³, N—C=O—R¹]

| Compound No. | -R¹ (-D-(CH)ₘ-E-R⁴ with R⁵) | -R² | -R³ | n | A | Broken line |
|---|---|---|---|---|---|---|
| 769 | -CH₂-Ph | -H | -NH₂ | 1 | C | — |
| 770 | -(CH₂)₃-Ph | -H | -NH₂ | 1 | C | — |
| 771 | -CH₂OCH₂-Ph | -H | -NH₂ | 1 | C | — |
| 772 | -CH(NHSO₂CH₃)-Ph | -H | -NH₂ | 1 | C | — |
| 773 | -CH(CH₂)₂(NHSO₂CH₃)-C₆H₄-COOCH₃ | -H | -NH₂ | 1 | C | — |
| 774 | -CHCH₂O(NHSO₂CH₃)-C₆H₄-COOH | -H | -NH₂ | 1 | C | — |
| 775 | -CHCH₂O(NHSO₂CH₃)-C₆H₄-COOCH₂-Ph | -H | -NH₂ | 1 | C | — |
| 776 | -CHCH₂(NHSO₂CH₃)-Ph | -H | -NH₂ | 1 | C | — |
| 777 | -CH₂CH(NHSO₂CH₃)-Ph | -H | -NH₂ | 1 | C | — |
| 778 | -CHCH₂(NHCHO)-Ph | -H | -NH₂ | 1 | C | — |
| 779 | -CHCH₂(NH₂)-Ph | -H | -NH₂ | 1 | C | — |

TABLE 1-continued $$\text{structure with }(CH_2)_m,\ N-C(=O)-R^1,\ -CNCH_2-\text{aryl}-A-R^3,\ R^2$$

| Compound No. | $-R^1\left(\begin{array}{c}-D-(CH)_m-E-R^4\\R^5\end{array}\right)$ | $-R^2$ | $-R^3$ | n | A | Broken line |
|---|---|---|---|---|---|---|
| 780 | $-CHCH_2-C_6H_5$ <br> $\|$ <br> $NHCOOC_2H_5$ | $-H$ | $-NH_2$ | 1 | C | — |
| 781 | $-CHCH_2-C_6H_5$ <br> $\|$ <br> $NHCOOCH(CH_3)_2$ | $-H$ | $-NH_2$ | 1 | C | — |
| 782 | $-CHCH_2-C_6H_5$ <br> $\|$ <br> $NHCOOC(CH_3)_3$ | $-H$ | $-NH_2$ | 1 | C | — |
| 783 | $-CH-C_6H_5$ <br> $\|$ <br> $OH$ | $-H$ | $-NH_2$ | 1 | C | — |
| 784 | $-CHCH_2-C_6H_5$ <br> $\|$ <br> $OCOC_2H_5$ | $-H$ | $-NH_2$ | 1 | C | — |
| 785 | $-CHCH_2-C_6H_5$ <br> $\|$ <br> $OCOOC_2H_5$ | $-H$ | $-NH_2$ | 1 | C | — |
| 786 | $-CHCH_2-C_6H_5$ <br> $\|$ <br> $OCONHCH_3$ | $-H$ | $-NH_2$ | 1 | C | — |
| 787 | $-CHCH_2-C_6H_5$ <br> $\|$ <br> $OCONHCH_2CH=CH_2$ | $-H$ | $-NH_2$ | 1 | C | — |
| 788 | $-CHCH_2C(CH_3)_3$ <br> $\|$ <br> $NHSO_2CH_3$ | $-H$ | $-NH_2$ | 1 | C | — |
| 789 | $-CH(CH_2)_2SCH_3$ <br> $\|$ <br> $NHSO_2CH_3$ | $-H$ | $-NH_2$ | 1 | C | — |
| 790 | $-CH(CH_2)_3CH_3$ <br> $\|$ <br> $NHSO_2CH_3$ | $-H$ | $-NH_2$ | 1 | C | — |
| 791 | $-CH(CH_2)_4CH_3$ <br> $\|$ <br> $NHSO_2CH_2COOH$ | $-H$ | $-NH_2$ | 1 | C | — |

TABLE 1-continued

| Compound No. | −R¹ ( −D−(CH)ₘ−E−R⁴ ) R⁵ | −R² | −R³ | n | A | Broken line |
|---|---|---|---|---|---|---|
| 792 | −CH(CH₂)₂COOH<br>│<br>NHSO₂−C₆H₅ | −H | −NH₂ | 1 | C | — |
| 793 | −CHC(SCH₃)(CH₃)₂<br>│<br>NHCOOC₂H₅ | −H | −NH₂ | 1 | C | — |
| 794 | −CHCH₂C(CH₃)₃<br>│<br>NHCOOC₂H₅ | −H | −NH₂ | 1 | C | — |
| 795 | −CHCH₂CH(C₂H₅)₂<br>│<br>NHCOOC₂H₅ | −H | −NH₂ | 1 | C | — |
| 796 | −CH(CH₂)₄CH₃<br>│<br>NHCOOC₂H₅ | −H | −NH₂ | 1 | C | — |
| 797 | −CHCH₂C(CH₃)₃<br>│<br>NHCOOCH(CH₃)₂ | −H | −NH₂ | 1 | C | — |
| 798 | −CHCH₂CH(C₂H₅)₂<br>│<br>NHCOOCH(CH₃)₂ | −H | −NH₂ | 1 | C | — |
| 799 | −CHCH₂C(CH₃)₃<br>│<br>NHCOOC(CH₃)₃ | −H | −NH₂ | 1 | C | — |
| 800 | −CHCH₂CH(C₂H₅)₂<br>│<br>NHCOOC(CH₃)₃ | −H | −NH₂ | 1 | C | — |
| 801 | −CH(CH₂)₂SCH₃<br>│<br>NHCOOC(CH₃)₃ | −H | −NH₂ | 1 | C | — |
| 802 | −CHCH₂C(CH₃)₃<br>│<br>NHCOOCH₂−C₆H₅ | −H | −NH₂ | 1 | C | — |
| 803 | −CHCH₂C(CH₃)₃<br>│<br>OH | −H | −NH₂ | 1 | C | — |
| 804 | −CHCH₂C(CH₃)₃<br>│<br>OCOOC₂H₅ | −H | −NH₂ | 1 | C | — |
| 805 | −CHCH₂CH(CH₃)₂<br>│<br>NHSO₂CH₃ | −H | −NH₂ | 1 | C | — |
| 806 | −CHCH(CH₃)₂<br>│<br>NHSO₂CH₃ | −H | −NH₂ | 1 | C | — |
| 807 | −CHC(CH₃)₃<br>│<br>NHSO₂CH₃ | −H | −NH₂ | 1 | C | — |

TABLE 1-continued

[Structure: (CH₂)ₙ attached to a pyrrolidine-like ring with N-C(=O)-R¹, bearing a -C(=O)-N(R²)-CH₂-[phenyl/cyclohexyl ring]-A-R³ substituent]

| Compound No. | $-R^1$ $\left(\begin{array}{c}-D-(CH)_m-E-R^4\\ \|\\ R^5\end{array}\right)$ | $-R^2$ | $-R^3$ | n | A | Broken line |
|---|---|---|---|---|---|---|
| 808 | —CHCH₂CH(CH₃)₂<br>\|<br>NHSO₂CH₃ | —H | —NH₂ | 1 | C | — |
| 809 | —CHCH₂OC(CH₃)₃<br>\|<br>NHSO₂CH₃ | —H | —NH₂ | 1 | C | — |
| 810 | —CHCH₂OC(CH₃)₂C₂H₅<br>\|<br>NHSO₂CH₃ | —H | —NH₂ | 1 | C | — |
| 811 | —CHCH₂O(C₂H₅)₂CH₃<br>\|<br>NHSO₂CH₃ | —H | —NH₂ | 1 | C | — |
| 812 | —CHC(CH₃)₂SCH₃<br>\|<br>NHSO₂CH₃ | —H | —NH₂ | 1 | C | — |
| 813 | —CHC(CH₃)₂SC₂H₅<br>\|<br>NHSO₂CH₃ | —H | —NH₂ | 1 | C | — |
| 814 | —CH—(cyclohexyl-H)<br>\|<br>NHSO₂CH₃ | —H | —NH₂ | 2 | C | Single bond |
| 815 | —CHCH₂—(cyclohexyl-H)<br>\|<br>NHSO₂CH₃ | —H | —NH₂ | 2 | C | Single bond |
| 816 | —CHCH₂—(cyclohexyl-H)<br>\|<br>NHCOOC₂H₅ | —H | —NH₂ | 2 | C | Single bond |
| 817 | —CHCH₂—(cyclohexyl-H)<br>\|<br>NHCOOCH(CH₃)₂ | —H | —NH₂ | 2 | C | Single bond |
| 818 | —CHCH₂—(cyclohexyl-H)<br>\|<br>NHCOOC(CH₃)₃ | —H | —NH₂ | 2 | C | Single bond |
| 819 | —CH—(cyclohexyl-H)<br>\|<br>OH | —H | —NH₂ | 2 | C | Single bond |
| 820 | —CHCH₂—(phenyl)<br>\|<br>NHSO₂CH₃ | —H | —NH₂ | 2 | C | Single bond |

TABLE 1-continued

| Compound No. | $-R^1 \left( \begin{array}{c} -D-(CH)_m-E-R^4 \\ R^5 \end{array} \right)$ | $-R^2$ | $-R^3$ | n | A | Broken line |
|---|---|---|---|---|---|---|
| 821 | −CHCH₂−(phenyl), NHCOOC₂H₅ | −H | −NH₂ | 2 | C | Single bond |
| 822 | −CHCH₂−(phenyl), NHCOOCH(CH₃)₂ | −H | −NH₂ | 2 | C | Single bond |
| 823 | −CHCH₂−(phenyl), NHCOOC(CH₃)₃ | −H | −NH₂ | 2 | C | Single bond |
| 824 | −CHCH₂−(phenyl), OCOOC₂H₅ | −H | −NH₂ | 2 | C | Single bond |
| 825 | −CH−(phenyl), OH | −H | −NH₂ | 2 | C | Single bond |
| 826 | −CHCH₂C(CH₃)₃, NHCOOC₂H₅ | −H | −NH₂ | 2 | C | Single bond |
| 827 | −CHCH₂C(CH₃)₃, NHCOOCH(CH₃)₂ | −H | −NH₂ | 2 | C | Single bond |
| 828 | −CH−(cyclohexyl, H), NHSO₂CH₃ | −H | −NH₂ | 2 | C | — |
| 829 | −CHCH₂−(cyclohexyl, H), NHSO₂CH₃ | −H | −NH₂ | 2 | C | — |
| 830 | −CHCH₂−(cyclohexyl, H), NHCOOC₂H₅ | −H | −NH₂ | 2 | C | — |
| 831 | −CHCH₂−(cyclohexyl, H), NHCOOCH(CH₃)₂ | −H | −NH₂ | 2 | C | — |

TABLE 1-continued

[Structure: (CH₂)ₙ-pyrrolidine ring with N-C(=O)-R¹, α-C(=O)-N(R²)-CH₂-[ring]-A-R³]

| Compound No. | -R¹ (-D-(CH)ₘ-E-R⁴ / R⁵) | -R² | -R³ | n | A | Broken line |
|---|---|---|---|---|---|---|
| 832 | -CHCH₂-(cyclohexyl, H) / NHCOOC(CH₃)₃ | -H | -NH₂ | 2 | C | — |
| 833 | -CH-(cyclohexyl, H) / OH | -H | -NH₂ | 2 | C | — |
| 834 | -CHCH₂-(phenyl) / NHSO₂CH₃ | -H | -NH₂ | 2 | C | — |
| 835 | -CHCH₂-(phenyl) / NHCOOC₂H₅ | -H | -NH₂ | 2 | C | — |
| 836 | -CHCH₂-(phenyl) / NHCOOCH(CH₃)₂ | -H | -NH₂ | 2 | C | — |
| 837 | -CHCH₂-(phenyl) / NHCOOC(CH₃)₃ | -H | -NH₂ | 2 | C | — |
| 838 | -CHCH₂-(phenyl) / OCOOC₂H₅ | -H | -NH₂ | 2 | C | — |
| 839 | -CH-(phenyl) / OH | -H | -NH₂ | 2 | C | — |
| 840 | -CHCH₂C(CH₃)₃ / NHCOOC₂H₅ | -H | -NH₂ | 2 | C | — |
| 841 | -CHCH₂C(CH₃)₃ / NHCOOCH(CH₃)₂ | -H | -NH₂ | 2 | C | — |
| 842 | -CH-(cyclohexyl, H) / NHSO₂CH₃ | -CH₃ | -NH₂ | 1 | C | Single bond |
| 843 | -CHCH₂-(cyclohexyl, H) / NHSO₂CH₃ | -CH₃ | -NH₂ | 1 | C | Single bond |

TABLE 1-continued

Structure:
$$\text{(CH}_2)_n\text{-pyrrolidine with N-C(=O)-R}^1, \text{ α-substituent -C(=O)-N(R}^2\text{)-CH}_2\text{-[ring]-A-R}^3$$

| Compound No. | $-R^1$ $\left(-D-(CH)_m-E-R^4 \text{ with } R^5\right)$ | $-R^2$ | $-R^3$ | n | A | Broken line |
|---|---|---|---|---|---|---|
| 844 | $-\text{CHCH}_2-$[cyclohexyl-H], NHCOOC$_2$H$_5$ | $-\text{CH}_3$ | $-\text{NH}_2$ | 1 | C | Single bond |
| 845 | $-\text{CHCH}_2-$[cyclohexyl-H], NHCOOCH(CH$_3$)$_2$ | $-\text{CH}_3$ | $-\text{NH}_2$ | 1 | C | Single bond |
| 846 | $-\text{CHCH}_2-$[cyclohexyl-H], NHCOOC(CH$_3$)$_3$ | $-\text{CH}_3$ | $-\text{NH}_2$ | 1 | C | Single bond |
| 847 | $-\text{CH}-$[cyclohexyl-H], OH | $-\text{CH}_3$ | $-\text{NH}_2$ | 1 | C | Single bond |
| 848 | $-\text{CHCH}_2-$[phenyl], NHSO$_2$CH$_3$ | $-\text{CH}_3$ | $-\text{NH}_2$ | 1 | C | Single bond |
| 849 | $-\text{CHCH}_2-$[phenyl], NHCOOC$_2$H$_5$ | $-\text{CH}_3$ | $-\text{NH}_2$ | 1 | C | Single bond |
| 850 | $-\text{CHCH}_2-$[phenyl], NHCOOCH(CH$_3$)$_2$ | $-\text{CH}_3$ | $-\text{NH}_2$ | 1 | C | Single bond |
| 851 | $-\text{CHCH}_2-$[phenyl], NHCOOC(CH$_3$)$_3$ | $-\text{CH}_3$ | $-\text{NH}_2$ | 1 | C | Single bond |
| 852 | $-\text{CHCH}_2-$[phenyl], OCOOC$_2$H$_5$ | $-\text{CH}_3$ | $-\text{NH}_2$ | 1 | C | Single bond |
| 853 | $-\text{CH}-$[phenyl], OH | $-\text{CH}_3$ | $-\text{NH}_2$ | 1 | C | Single bond |
| 854 | $-\text{CHCH}_2\text{C(CH}_3)_3$, NHCOOC$_2$H$_5$ | $-\text{CH}_3$ | $-\text{NH}_2$ | 1 | C | Single bond |

TABLE 1-continued

| Compound No. | $-R^1 \left( \begin{array}{c} -D-(CH)_m-E-R^4 \\ R^5 \end{array} \right)$ | $-R^2$ | $-R^3$ | n | A | Broken line |
|---|---|---|---|---|---|---|
| 855 | -CHCH$_2$C(CH$_3$)$_3$<br>\|<br>NHCOOCH(CH$_3$)$_2$ | -CH$_3$ | -NH$_2$ | 1 | C | Single bond |
| 856 | -CH-[C$_6$H$_{11}$]<br>\|<br>NHSO$_2$CH$_3$ | -CH$_3$ | -NH$_2$ | 1 | C | — |
| 857 | -CHCH$_2$-[C$_6$H$_{11}$]<br>\|<br>NHSO$_2$CH$_3$ | -CH$_3$ | -NH$_2$ | 1 | C | — |
| 858 | -CHCH$_2$-[C$_6$H$_{11}$]<br>\|<br>NHCOOC$_2$H$_5$ | -CH$_3$ | -NH$_2$ | 1 | C | — |
| 859 | -CHCH$_2$-[C$_6$H$_{11}$]<br>\|<br>NHCOOCH(CH$_3$)$_2$ | -CH$_3$ | -NH$_2$ | 1 | C | — |
| 860 | -CHCH$_2$-[C$_6$H$_{11}$]<br>\|<br>NHCOOC(CH$_3$)$_3$ | -CH$_3$ | -NH$_2$ | 1 | C | — |
| 861 | -CH-[C$_6$H$_{11}$]<br>\|<br>OH | -CH$_3$ | -NH$_2$ | 1 | C | — |
| 862 | -CHCH$_2$-[C$_6$H$_5$]<br>\|<br>NHSO$_2$CH$_3$ | -CH$_3$ | -NH$_2$ | 1 | C | — |
| 863 | -CHCH$_2$-[C$_6$H$_5$]<br>\|<br>NHCOOC$_2$H$_5$ | -CH$_3$ | -NH$_2$ | 1 | C | — |
| 864 | -CHCH$_2$-[C$_6$H$_5$]<br>\|<br>NHCOOCH(CH$_3$)$_2$ | -CH$_3$ | -NH$_2$ | 1 | C | — |
| 865 | -CHCH$_2$-[C$_6$H$_5$]<br>\|<br>NHCOOC(CH$_3$)$_3$ | -CH$_3$ | -NH$_2$ | 1 | C | — |

TABLE 1-continued

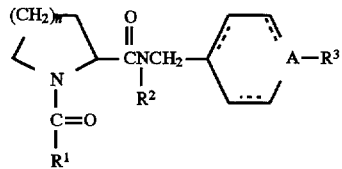

| Compound No. | -R¹ ( -D-(CH)ₘ-E-R⁴ / R⁵ ) | -R² | -R³ | n | A | Broken line |
|---|---|---|---|---|---|---|
| 866 | -CHCH₂-⌬ / OCOOC₂H₅ | -CH₃ | -NH₂ | 1 | C | — |
| 867 | -CH-⬡H / OH | -CH₃ | -NH₂ | 1 | C | — |
| 868 | -CHCH₂C(CH₃)₃ / NHCOOC₂H₅ | -CH₃ | -NH₂ | 1 | C | — |
| 869 | -CHCH₂C(CH₃)₃ / NHCOOCH(CH₃)₂ | -CH₃ | -NH₂ | 1 | C | — |
| 870 | -CH-⬡H / NHSO₂CH₃ | -CH₃ | -NH₂ | 2 | C | Single bond |
| 871 | -CHCH₂-⬡H / NHSO₂CH₃ | -CH₃ | -NH₂ | 2 | C | Single bond |
| 872 | -CHCH₂-⬡H / NHCOOC₂H₅ | -CH₃ | -NH₂ | 2 | C | Single bond |
| 873 | -CHCH₂-⬡H / NHCOOCH(CH₃)₂ | -CH₃ | -NH₂ | 2 | C | Single bond |
| 874 | -CHCH₂-⬡H / NHCOOC(CH₃)₃ | -CH₃ | -NH₂ | 2 | C | Single bond |
| 875 | -CH-⬡H / OH | -CH₃ | -NH₂ | 2 | C | Single bond |
| 876 | -CHCH₂-⌬ / NHSO₂CH₃ | -CH₃ | -NH₂ | 2 | C | Single bond |

TABLE 1-continued

| Compound No. | -R¹ (-D-(CH)ₘ-E-R⁴ / R⁵) | -R² | -R³ | n | A | Broken line |
|---|---|---|---|---|---|---|
| 877 | -CHCH₂-(C₆H₅) / NHCOOC₂H₅ | -CH₃ | -NH₂ | 2 | C | Single bond |
| 878 | -CHCH₂-(C₆H₅) / NHCOOCH(CH₃)₂ | -CH₃ | -NH₂ | 2 | C | Single bond |
| 879 | -CHCH₂-(C₆H₅) / NHCOOC(CH₃)₃ | -CH₃ | -NH₂ | 2 | C | Single bond |
| 880 | -CHCH₂-(C₆H₅) / OCOOC₂H₅ | -CH₃ | -NH₂ | 2 | C | Single bond |
| 881 | -CH-(C₆H₅) / OH | -CH₃ | -NH₂ | 2 | C | Single bond |
| 882 | -CHCH₂C(CH₃)₃ / NHCOOC₂H₅ | -CH₃ | -NH₂ | 2 | C | Single bond |
| 883 | -CHCH₂C(CH₃)₃ / NHCOOCH(CH₃)₂ | -CH₃ | -NH₂ | 2 | C | Single bond |
| 884 | -CH-(C₆H₁₁) / NHSO₂CH₃ | -CH₃ | -NH₂ | 2 | C | — |
| 885 | -CHCH₂-(C₆H₁₁) / NHSO₂CH₃ | -CH₃ | -NH₂ | 2 | C | — |
| 886 | -CHCH₂-(C₆H₁₁) / NHCOOC₂H₅ | -CH₃ | -NH₂ | 2 | C | — |
| 887 | -CHCH₂-(C₆H₁₁) / NHCOOCH(CH₃)₂ | -CH₃ | -NH₂ | 2 | C | — |

TABLE 1-continued

[Structure: (CH₂)ₘ group on pyrrolidine ring with N-C(=O)-R¹, attached to CH with R² and C(=O)N-CH₂-phenyl-A-R³]

| Compound No. | -R¹ ( -D-(CH)ₘ-E-R⁴ / R⁵ ) | -R² | -R³ | n | A | Broken line |
|---|---|---|---|---|---|---|
| 888 | -CHCH₂-(cyclohexyl, H) / NHCOOC(CH₃)₃ | -CH₃ | -NH₂ | 2 | C | — |
| 889 | -CH-(cyclohexyl, H) / OH | -CH₃ | -NH₂ | 2 | C | — |
| 890 | -CHCH₂-(phenyl) / NHSO₂CH₃ | -CH₃ | -NH₂ | 2 | C | — |
| 891 | -CHCH₂-(phenyl) / NHCOOC₂H₅ | -CH₃ | -NH₂ | 2 | C | — |
| 892 | -CHCH₂-(phenyl) / NHCOOCH(CH₃)₂ | -CH₃ | -NH₂ | 2 | C | — |
| 893 | -CHCH₂-(phenyl) / NHCOOC(CH₃)₃ | -CH₃ | -NH₂ | 2 | C | — |
| 894 | -CHCH₂-(phenyl) / OCOOC₂H₅ | -CH₃ | -NH₂ | 2 | C | — |
| 895 | -CH-(phenyl) / OH | -CH₃ | -NH₂ | 2 | C | — |
| 896 | -CHCH₂C(CH₃)₃ / NHCOOC₂H₅ | -CH₃ | -NH₂ | 2 | C | — |
| 897 | -CHCH₂C(CH₃)₃ / NHCOOCH(CH₃)₂ | -CH₃ | -NH₂ | 2 | C | — |
| 898 | -CHCH₂-(cyclohexyl, H) / NHCOOC(CH₃)₃ | -H | -NHCH₃ | 1 | C | Single bond |
| 899 | -CHCH₂-(cyclohexyl, H) / NHSO₂CH₃ | -H | -NHCH₃ | 1 | C | Single bond |

TABLE 1-continued

Structure:
(CH₂)ₘ attached to pyrrolidine ring with N—C(=O)—R¹; α-carbon bears —C(=O)N(R²)CH₂—[ring A]—R³

$$-R^1 \left( -D-(CH)_m-E-R^4 \atop R^5 \right)$$

| Compound No. | —R¹ | —R² | —R³ | n | A | Broken line |
|---|---|---|---|---|---|---|
| 900 | —CH(OH)-cyclohexyl(H) | —H | —NHCH₃ | 1 | C | Single bond |
| 901 | —CH(NHSO₂CH₃)CH₂-phenyl | —H | —NHCH₃ | 1 | C | Single bond |
| 902 | —CH(NHCOOC₂H₅)CH₂C(CH₃)₃ | —H | —NHCH₃ | 1 | C | Single bond |
| 903 | —CH(NHSO₂CH₃)CH₂C(CH₃)₃ | —H | —NHCH₃ | 1 | C | Single bond |
| 904 | —CH(NHCOOC(CH₃)₃)CH₂-cyclohexyl(H) | —H | —NHCH₃ | 1 | C | — |
| 905 | —CH(NHSO₂CH₃)CH₂-cyclohexyl(H) | —H | —NHCH₃ | 1 | C | — |
| 906 | —CH(OH)-cyclohexyl(H) | —H | —NHCH₃ | 1 | C | — |
| 907 | —CH(NHSO₂CH₃)CH₂-phenyl | —H | —NHCH₃ | 1 | C | — |
| 908 | —CH(NHCOOC₂H₅)CH₂C(CH₃)₃ | —H | —NHCH₃ | 1 | C | — |
| 909 | —CH(NHSO₂CH₃)CH₂C(CH₃)₃ | —H | —NHCH₃ | 1 | C | — |
| 910 | —CH(NHCOOC(CH₃)₃)CH₂-cyclohexyl(H) | —H | —NHC₂H₅ | 1 | C | Single bond |
| 911 | —CH(NHSO₂CH₃)CH₂-cyclohexyl(H) | —H | —NHC₂H₅ | 1 | C | Single bond |
| 912 | —CH(OH)-cyclohexyl(H) | —H | —NHC₂H₅ | 1 | C | Single bond |

TABLE 1-continued

| Compound No. | -R¹ ( -D-(CH)ₘ-E-R⁴ / R⁵ ) | -R² | -R³ | n | A | Broken line |
|---|---|---|---|---|---|---|
| 913 | -CHCH₂-(phenyl) / NHSO₂CH₃ | -H | -NHC₂H₅ | 1 | C | Single bond |
| 914 | -CHCH₂C(CH₃)₃ / NHCOOC₂H₅ | -H | -NHC₂H₅ | 1 | C | Single bond |
| 915 | -CHCH₂C(CH₃)₃ / NHSO₂CH₃ | -H | -NHC₂H₅ | 1 | C | Single bond |
| 916 | -CHCH₂-(cyclohexyl, H) / NHCOOC(CH₃)₃ | -H | -NHC₂H₅ | 1 | C | — |
| 917 | -CHCH₂-(cyclohexyl, H) / NHSO₂CH₃ | -H | -NHC₂H₅ | 1 | C | — |
| 918 | -CH-(cyclohexyl, H) / OH | -H | -NHC₂H₅ | 1 | C | — |
| 919 | -CHCH₂-(phenyl) / NHSO₂CH₃ | -H | -NHC₂H₅ | 1 | C | — |
| 920 | -CHCH₂C(CH₃)₃ / NHCOOC₂H₅ | -H | -NHC₂H₅ | 1 | C | — |
| 921 | -CHCH₂C(CH₃)₃ / NHSO₂CH₃ | -H | -NHC₂H₅ | 1 | C | — |
| 922 | -CHCH₂-(cyclohexyl, H) / NHCOOC(CH₃)₃ | -H | -NHCOCH₃ | 1 | C | Single bond |
| 923 | -CHCH₂-(cyclohexyl, H) / NHSO₂CH₃ | -H | -NHCOCH₃ | 1 | C | Single bond |
| 924 | -CH-(cyclohexyl, H) / OH | -H | -NHCOCH₃ | 1 | C | Single bond |
| 925 | -CHCH₂-(phenyl) / NHSO₂CH₃ | -H | -NHCOCH₃ | 1 | C | Single bond |

TABLE 1-continued

| Compound No. | -R¹ ( -D-(CH)$_m$-E-R⁴ / R⁵ ) | -R² | -R³ | n | A | Broken line |
|---|---|---|---|---|---|---|
| 926 | -CHCH₂C(CH₃)₃ / NHCOOC₂H₅ | -H | -NHCOCH₃ | 1 | C | Single bond |
| 927 | -CHCH₂C(CH₃)₃ / NHSO₂CH₃ | -H | -NHCOCH₃ | 1 | C | Single bond |
| 928 | -CHCH₂-[cyclohexyl-H] / NHCOOC(CH₃)₃ | -H | -NHCOCH₃ | 1 | C | — |
| 929 | -CHCH₂-[cyclohexyl-H] / NHSO₂CH₃ | -H | -NHCOCH₃ | 1 | C | — |
| 930 | -CH-[cyclohexyl-H] / OH | -H | -NHCOCH₃ | 1 | C | — |
| 931 | -CHCH₂-[phenyl] / NHSO₂CH₃ | -H | -NHCOCH₃ | 1 | C | — |
| 932 | -CHCH₂C(CH₃)₃ / NHCOOC₂H₅ | -H | -NHCOCH₃ | 1 | C | — |
| 933 | -CHCH₂C(CH₃)₃ / NHSO₂CH₃ | -H | -NHCOCH₃ | 1 | C | — |
| 934 | -CHCH₂-[cyclohexyl-H] / NHCOOC(CH₃)₃ | -H | -NHCOOCH₃ | 1 | C | Single bond |
| 935 | -CHCH₂-[cyclohexyl-H] / NHSO₂CH₃ | -H | -NHCOOCH₃ | 1 | C | Single bond |
| 936 | -CH-[cyclohexyl-H] / OH | -H | -NHCOOCH₃ | 1 | C | Single bond |
| 937 | -CHCH₂-[phenyl] / NHSO₂CH₃ | -H | -NHCOOCH₃ | 1 | C | Single bond |
| 938 | -CHCH₂C(CH₃)₃ / NHCOOC₂H₅ | -H | -NHCOOCH₃ | 1 | C | Single bond |

TABLE 1-continued

| Compound No. | $-R^1 \left( \begin{array}{c} -D-(CH)_m-E-R^4 \\ R^5 \end{array} \right)$ | $-R^2$ | $-R^3$ | n | A | Broken line |
|---|---|---|---|---|---|---|
| 939 | —CHCH$_2$C(CH$_3$)$_3$<br>\|<br>NHSO$_2$CH$_3$ | —H | —NHCOOCH$_3$ | 1 | C | Single bond |
| 940 | —CHCH$_2$—(C$_6$H$_{11}$)<br>\|<br>NHCOOC(CH$_3$)$_3$ | —H | —NHCOOCH$_3$ | 1 | C | — |
| 941 | —CHCH$_2$—(C$_6$H$_{11}$)<br>\|<br>NHSO$_2$CH$_3$ | —H | —NHCOOCH$_3$ | 1 | C | — |
| 942 | —CH—(C$_6$H$_{11}$)<br>\|<br>OH | —H | —NHCOOCH$_3$ | 1 | C | — |
| 943 | —CHCH$_2$—(C$_6$H$_5$)<br>\|<br>NHSO$_2$CH$_3$ | —H | —NHCOOCH$_3$ | 1 | C | — |
| 944 | —CHCH$_2$C(CH$_3$)$_3$<br>\|<br>NHCOOC$_2$H$_5$ | —H | —NHCOOCH$_3$ | 1 | C | — |
| 945 | —CHCH$_2$C(CH$_3$)$_3$<br>\|<br>NHSO$_2$CH$_3$ | —H | —NHCOOCH$_3$ | 1 | C | — |
| 946 | —CHCH$_2$—(C$_6$H$_{11}$)<br>\|<br>NHCOOC(CH$_3$)$_3$ | —H | —NHCOOC(CH$_3$)$_3$ | 1 | C | Single bond |
| 947 | —CHCH$_2$—(C$_6$H$_{11}$)<br>\|<br>NHSO$_2$CH$_3$ | —H | —NHCOOC(CH$_3$)$_3$ | 1 | C | Single bond |
| 948 | —CH—(C$_6$H$_{11}$)<br>\|<br>OH | —H | —NHCOOC(CH$_3$)$_3$ | 1 | C | Single bond |
| 949 | —CHCH$_2$—(C$_6$H$_{11}$)<br>\|<br>NHSO$_2$CH$_3$ | —H | —NHCOOC(CH$_3$)$_3$ | 1 | C | Single bond |
| 950 | —CHCH$_2$C(CH$_3$)$_3$<br>\|<br>NHCOOC$_2$H$_5$ | —H | —NHCOOC(CH$_3$)$_3$ | 1 | C | Single bond |
| 951 | —CHCH$_2$C(CH$_3$)$_3$<br>\|<br>NHSO$_2$CH$_3$ | —H | —NHCOOC(CH$_3$)$_3$ | 1 | C | Single bond |

TABLE 1-continued

| Compound No. | $-R^1 \left( \begin{array}{c} -D-(CH)_m-E-R^4 \\ R^5 \end{array} \right)$ | $-R^2$ | $-R^3$ | n | A | Broken line |
|---|---|---|---|---|---|---|
| 952 | -CHCH₂-(C₆H₁₁)<br>\|<br>NHCOOC(CH₃)₃ | -H | -NHCOOC(CH₃)₃ | 1 | C | — |
| 953 | -CHCH₂-(C₆H₁₁)<br>\|<br>NHSO₂CH₃ | -H | -NHCOOC(CH₃)₃ | 1 | C | — |
| 954 | -CH-(C₆H₁₁)<br>\|<br>OH | -H | -NHCOOC(CH₃)₃ | 1 | C | — |
| 955 | -CHCH₂-C₆H₅<br>\|<br>NHSO₂CH₃ | -H | -NHCOOC(CH₃)₃ | 1 | C | — |
| 956 | -CHCH₂C(CH₃)₃<br>\|<br>NHCOOC₂H₅ | -H | -NHCOOC(CH₃)₃ | 1 | C | — |
| 957 | -CHCH₂C(CH₃)₃<br>\|<br>NHSO₂CH₃ | -H | -NHCOOC(CH₃)₃ | 1 | C | — |
| 958 | -CHCH₂-(C₆H₁₁)<br>\|<br>NHCOOC(CH₃)₃ | -H | -NHCH₂-[methyl-dioxolenone] | 1 | C | Single bond |
| 959 | -CHCH₂-(C₆H₁₁)<br>\|<br>NHSO₂CH₃ | -H | -NHCH₂-[methyl-dioxolenone] | 1 | C | Single bond |
| 960 | -CH-(C₆H₁₁)<br>\|<br>OH | -H | -NHCH₂-[methyl-dioxolenone] | 1 | C | Single bond |
| 961 | -CHCH₂-C₆H₅<br>\|<br>NHSO₂CH₃ | -H | -NHCH₂-[methyl-dioxolenone] | 1 | C | Single bond |
| 962 | -CHCH₂C(CH₃)₃<br>\|<br>NHCOOC₂H₅ | -H | -NHCH₂-[methyl-dioxolenone] | 1 | C | Single bond |

TABLE 1-continued

| Compound No. | $-R^1 \left( \begin{array}{c} -D-(CH)_m-E-R^4 \\ R^5 \end{array} \right)$ | $-R^2$ | $-R^3$ | n | A | Broken line |
|---|---|---|---|---|---|---|
| 963 | —CHCH$_2$C(CH$_3$)$_3$<br>\|<br>NHSO$_2$CH$_3$ | —H | —NHCH$_2$–C(CH$_3$)=C(O-CH(-)-O) (methylenedioxy methine) | 1 | C | Single bond |
| 964 | —CHCH$_2$–C$_6$H$_{11}$<br>\|<br>NHCOOC(CH$_3$)$_3$ | —H | (same as 963) | 1 | C | — |
| 965 | —CHCH$_2$–C$_6$H$_{11}$<br>\|<br>NHSO$_2$CH$_3$ | —H | (same as 963) | 1 | C | — |
| 966 | —CH(OH)–C$_6$H$_{11}$ | —H | (same as 963) | 1 | C | — |
| 967 | —CHCH$_2$–C$_6$H$_5$<br>\|<br>NHSO$_2$CH$_3$ | —H | (same as 963) | 1 | C | — |
| 968 | —CHCH$_2$C(CH$_3$)$_3$<br>\|<br>NHCOOC$_2$H$_5$ | —H | (same as 963) | 1 | C | — |
| 969 | —CHCH$_2$C(CH$_3$)$_3$<br>\|<br>NHSO$_2$CH$_3$ | —H | (same as 963) | 1 | C | — |
| 970 | —CHCH$_2$O–C$_6$H$_4$–COOH<br>\|<br>NHSO$_2$CH$_3$ | —H | —C(=NH)NH$_2$ | 1 | C | Single bond |
| 971 | —CHCH$_2$–C$_6$H$_4$–OCH$_2$COOC$_2$H$_5$<br>\|<br>NHSO$_2$CH$_3$ | —H | —C(=NH)NH$_2$ | 1 | C | Single bond |
| 972 | —CHCH$_2$–C$_6$H$_5$<br>\|<br>NHCOOC$_2$H$_5$ | —H | —C(=NH)NH$_2$ | 1 | C | Single bond |

TABLE 1-continued

[Structure shown at top of table]

| Compound No. | -R¹ ( -D-(CH)ₘ-E-R⁴ / R⁵ ) | -R² | -R³ | n | A | Broken line |
|---|---|---|---|---|---|---|
| 973 | -CH(CH₂)₄CH₃ / NHSO₂CH₃ | -H | -C(=NH)NH₂ | 1 | C | Single bond |
| 974 | -CHCH₂O-[3-CH₂COOH-phenyl] / NHSO₂CH₃ | -H | -C(=NH)NH₂ | 1 | C | Single bond |
| 975 | -CHCH₂O-[4-CH₂COOH-phenyl] / NHSO₂CH₃ | -H | -C(=NH)NH₂ | 1 | C | Single bond |
| 976 | -CH(CH₂)₄CH₃ / NHSO₂CH₂COOC₂H₅ | -H | -C(=NH)NH₂ | 1 | C | Single bond |
| 977 | -CHCH₂OC(CH₃)₂C₂H₅ / NHCOOCH(CH₃)₂ | -H | -C(=NH)NH₂ | 1 | C | — |
| 978 | -CHCH₂OC(CH₃)₂C₂H₅ / NHCOOC₂H₅ | -H | -C(=NH)NH₂ | 1 | C | — |
| 979 | -CHCH₂OC(C₂H₅)₂CH₃ / NHCOOCH(CH₃)₂ | -H | -C(=NH)NH₂ | 1 | C | — |
| 980 | -CHCH₂SC(CH₃)₃ / NHCOOC₂H₅ | -H | -C(=NH)NH₂ | 1 | C | — |
| 981 | -CHCH₂O-[1-CH₃-cyclopentyl] / NHCOOCH(CH₃)₂ | -H | -C(=NH)NH₂ | 1 | C | — |
| 982 | -CHCH(CH₃)OC(CH₃)₃ / NHCOOCH(CH₃)₂ | -H | -C(=NH)NH₂ | 1 | C | — |
| 983 | -CHC(CH₃)₂SCH(CH₃)₂ / NHCOOC₂H₅ | -H | -C(=NH)NH₂ | 1 | C | — |

TABLE 1-continued

| Compound No. | $-R^1 \left( \begin{array}{c} -D-(CH)_m-E-R^4 \\ | \\ R^5 \end{array} \right)$ | $-R^2$ | $-R^3$ | n | A | Broken line |
|---|---|---|---|---|---|---|
| 984 | -CHCH₂-C₆H₅, NHCOOCH₂COOC₂H₅ | -H | -C(=NOH)NH₂ | 1 | C | Single bond |
| 985 | -CH-C₆H₅, NHCOOC₂H₅ | -H | -C(=NOH)NH₂ | 1 | C | Single bond |
| 986 | -CH-(thienyl), NHCOOC₂H₅ | -H | -C(=NOH)NH₂ | 1 | C | Single bond |
| 987 | -CH-C₆H₄-F, NHCOOC₂H₅ | -H | -C(=NOH)NH₂ | 1 | C | Single bond |
| 988 | -CHCH₂-C₆H₅, NHCOOCH₂-C₆H₅ | -H | -C(=NOH)NH₂ | 1 | C | Single bond |
| 989 | -CHCH₂C(CH₃)₃, NHCOOC(CH₃)₃ | -H | -C(=NOH)NH₂ | 1 | C | Single bond |
| 990 | -CHCH₂-C₆H₅, NHCON(CH₃)₂ | -H | -C(=NOH)NH₂ | 1 | C | Single bond |
| 991 | -CHCH₂COOC(CH₃)₃, NHCOOCH₂-C₆H₅ | -H | -C(=NOH)NH₂ | 1 | C | Single bond |
| 992 | -CHCH₂OH, NHCOOC(CH₃)₃ | -H | -C(=NOH)NH₂ | 1 | C | — |
| 993 | -CHCH(CH₃)OC(CH₃)₃, NHCOOCH(CH₃)₂ | -H | -C(=NOH)NH₂ | 1 | C | — |

TABLE 1-continued

| Compound No. | $-R^1 \left( \begin{array}{c} -D-(CH)_m-E-R^4 \\ R^5 \end{array} \right)$ | $-R^2$ | $-R^3$ | n | A | Broken line |
|---|---|---|---|---|---|---|
| 994 | -CH(-cyclohexyl)<br>\|<br>OCOCH₃ | -H | -C(=NOH)NH₂ | 1 | C | — |
| 995 | -CHCH₂O-C(CH₃)(cyclopentyl)<br>\|<br>NHCOOCH(CH₃)₃ | -H | -C(=NOH)NH₂ | 1 | C | — |
| 996 | -CHCH₂OC(CH₃)₃<br>\|<br>NHCOOC₂H₅ | -H | -C(=NOCOOCH₃)NH₂ | 1 | C | — |
| 997 | -CHCH₂CH(CH₃)₂<br>\|<br>OH | -H | -C(=NOCOOC₂H₅)NH₂ | 1 | C | — |
| 998 | -CHCH₂OC(CH₃)₃<br>\|<br>NHCOOC₂H₅ | -H | -C(=NOCOCH₃)NH₂ | 1 | C | — |
| 999 | -CHCH₂OC(CH₃)₃<br>\|<br>NHCOOCH(CH₃)₂ | -H | -C(=NOCOOCH₃)NH₂ | 1 | C | — |
| 1000 | -CHCH₂C(CH₃)₃<br>\|<br>NHSO₂CH₃ | -H | -C(=NOCOOC₂H₅)NH₂ | 1 | C | Single bond |
| 1001 | -CH(-cyclohexyl)<br>\|<br>NHSO₂CH₃ | -H | -C(=NOCOOCH₃)NH₂ | 1 | C | Single bond |
| 1002 | -CHCH₂-(C₆H₄)-OCH₃<br>\|<br>NHSO₂CH₃ | -H | -NH₂ | 1 | C | — |
| 1003 | -CHCH₂OC(CH₃)₃<br>\|<br>NHCOOC₂H₅ | -H | -NH₂ | 1 | C | — |
| 1004 | -CH(-cyclohexyl)<br>\|<br>NHCOOC₂H₅ | -H | -NHCH₂-C(CH₃)=C(O-CH(O-)-O) | 1 | C | — |

TABLE 1-continued

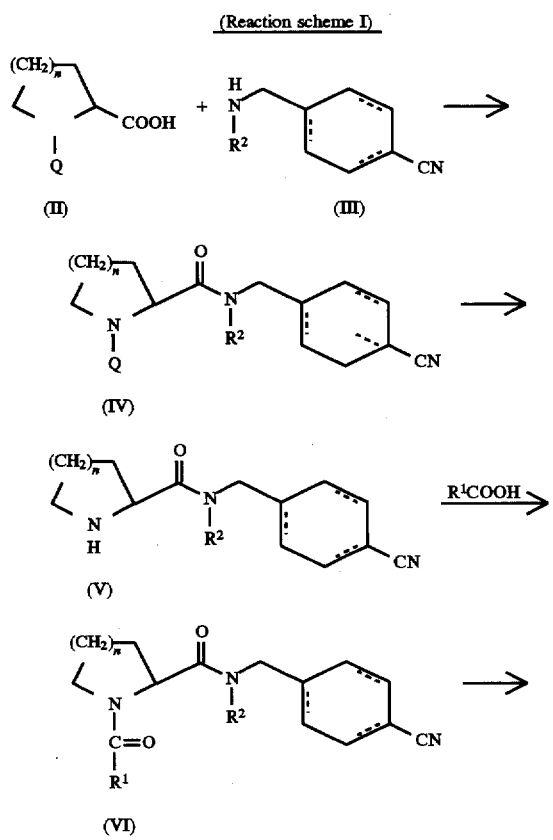

| Compound No. | $-R^1 \begin{pmatrix} -D-(CH)_m-E-R^4 \\ R^5 \end{pmatrix}$ | $-R^2$ | $-R^3$ | n | A | Broken line |
|---|---|---|---|---|---|---|
| 1005 | —CHCH$_2$C(CH$_3$)$_3$<br>\|<br>NHCOOCH(CH$_3$)$_2$ | —H | —NHCH$_2$—[isopropylidene dioxolanone group with CH$_3$] | 1 | C | — |
| 1006 | —CH—cyclohexyl<br>\|<br>NHSO$_2$CH$_3$ | —H | —NHCH$_2$—[isopropylidene dioxolanone group with CH$_3$] | 1 | C | — |

Hereinafter, the production process for the compounds of the present invention will be explained.

The compounds of the present invention can be produced through any combination of reactions suitable for the objective compounds. Typical reaction schemes will be shown below, but they should not be construed to be limiting the scope of the present invention.

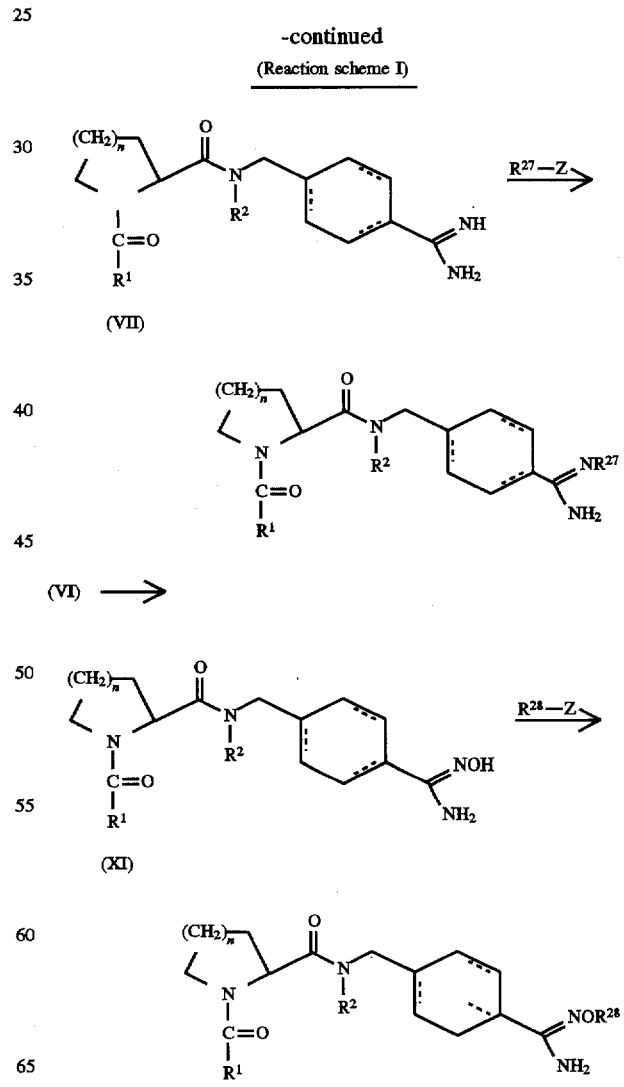

(Reaction Scheme II)

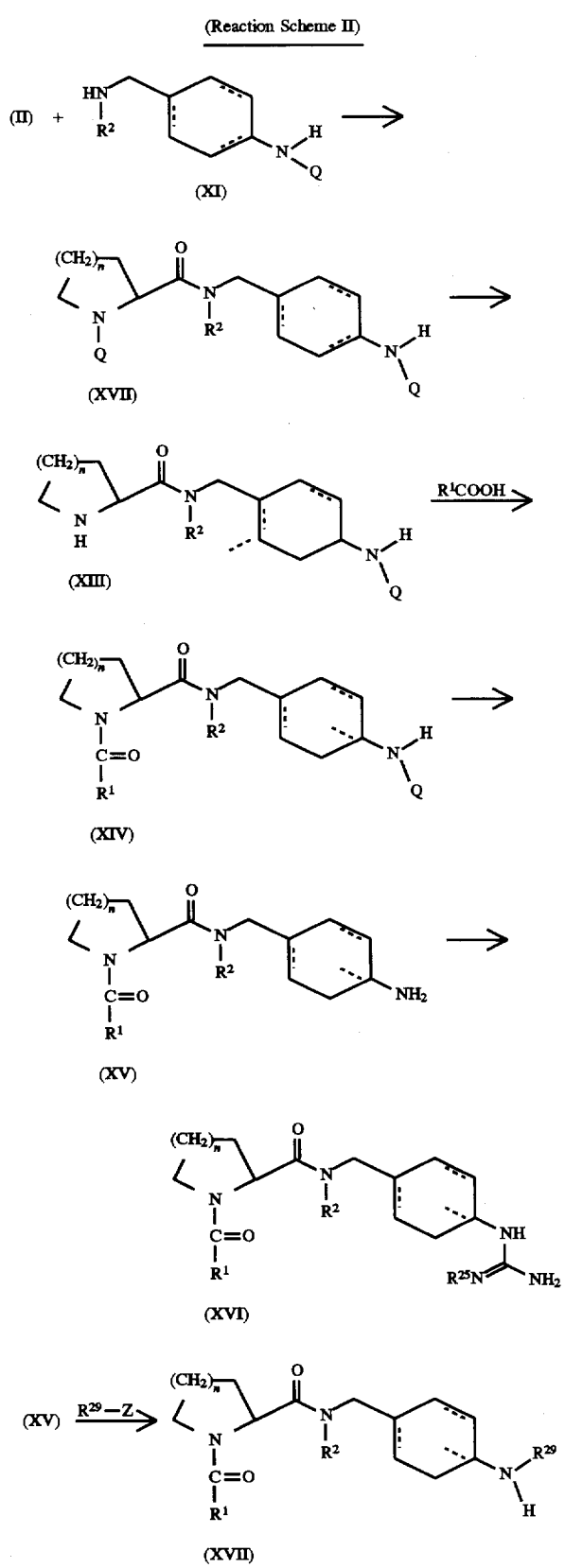

(Reaction scheme III)

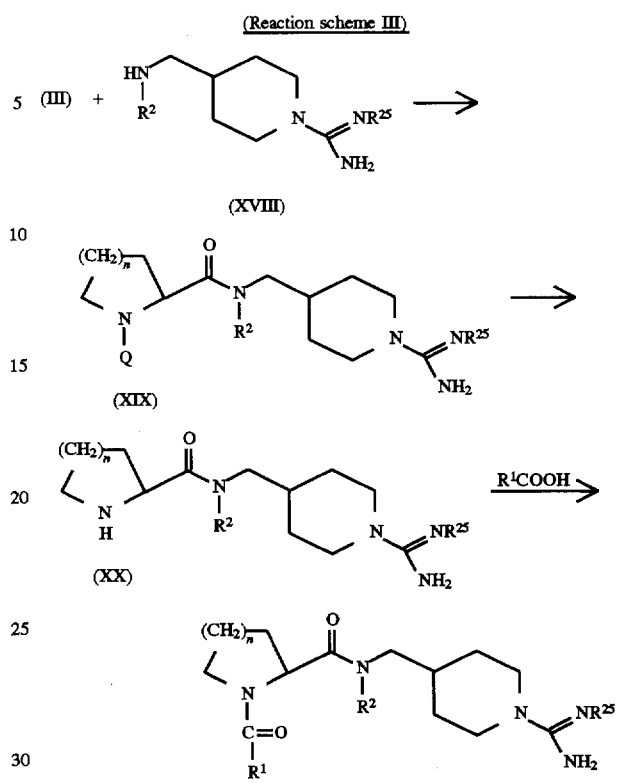

wherein $R^1$, $R^2$, $R^{25}$, n and broken line are as defined above; Q is an amino-protecting group, such as benzyloxycarbonyl group, tertiary butyloxycarbonyl group, etc.; Z is a leaving group such as halogen atom, methanesulfonyloxy group, toluenesulfonyloxy group, trifluoromethylsulfonyloxy group, acetoxy (acetyloxy) group, etc.; $R^{27}$, $R^{28}$ and $R^{29}$ indicate a specific substituent contained in $R^{25}$ and $R^{26}$; $R^{27}$ is a $C_1$–$C_6$ alkyl group, a $C_2$–$C_7$ acyl group or a $C_2$–$C_7$ alkoxycarbonyl group; $R^{28}$ is a $C_1$–$C_6$ alkyl group, a $C_2$–$C_7$ acyl group, a $C_2$–$C_7$ alkoxycarbonyl group or a $C_2$–$C_7$ hydroxyalkylcarbonyl group; $R^{29}$ is a $C_1$–$C_6$ alkyl group, a $C_2$–$C_7$ acyl group, a $C_2$–$C_7$ alkoxycarbonyl group or 5–$C_1$–$C_3$ alkyl-1,3-dioxol-2-on-4-ylmethyl group.

In the above reaction schemes, a known method for synthesizing amide can be used for synthesizing the compounds (IV), (VI), (XII), (XIV), (XIX) and (XXI). There are various conventional methods, for example, a method using dehydrating agents such as dicyclohexylcarbodiimide, 1-ethyl-3-(dimethylaminopropyl)carbodiimide, carbonyldiimidazole, etc., azido method, acid halide method, acid anhydride method, active ester method and the like.(e.g., see, "JIKKEN KAGAKU KOZA, 22, YUKI-GOSEI IV", pp. 259-(1992), ed. "JAPAN Chemical Society", 4th. edition, published by Maruzen). The reaction is conducted under cooling or heating (or at room temperature) using an inert solvent such as tetrahydrofuran, diethyl ether, dichloromethane, etc. in a conventional manner. In the above schemes, the compounds (V), (XIII), (XV) and (XX) can be synthesized by deprotection according to a method known in the peptide chemistry (e.g. see "The Principle and Experimental Procedures of Peptide Synthesis" written by Nobuo IZUMIYA et al., published by Maruzen).

Further, the compound (VII) is synthesized by reacting imidate, which is obtained by reacting the compound (VI)

with alcohol and an inorganic acid such as hydrochloric acid, with ammonia or an ammonium salt; or by reacting a thioamide compound, which is obtained by reacting the compound (VI) with hydrogen sulfide in the presence of an organic base such as triethylamine, pyridine, etc., with a lower alkylhalogen compound such as methyl iodide, etc., followed by reacting the resulting thioimidate compound with ammonia or an ammonium salt. Further, the compound (IX) is synthesized by reacting the compound (VI) with hydroxylamine or acid adduct thereof in a suitable solvent such as water, alcohol, tetrahydrofuran, etc. at room temperature or under heating.

Further, the compounds (VIII), (X) and (XVII) are synthesized by reacting the compounds (VI I), (IX) and (XV) with $R^{27}$—Z, $R^{28}$—Z or $R^{29}$—Z in an inert solvent such as tetrahydrofuran, ether, dichloromethane, etc. in the presence of an organic or inorganic base under cooling or heating (or at room temperature), respectively.

Further, the compound (XVI) is synthesized by reacting the compound (XV) with a guanidizing reagent such as 2-alkylisothiourea derivative or acid adduct thereof in a suitable solvent such as water, alcohol, tetrahydrofuran, etc. at room temperature or under heating.

The respective compounds thus obtained can be isolated and purified by conventional chemical procedures such as extraction, crystallization, recrystallization, various chromatography and the like.

When the compounds of the present invention are used for clinical application, a proportion of a therapeutically active ingredient to a carrier component varies within a range of 1 to 90% by weight. For example, the compounds of the present invention may be orally administered in the dosage form such as granules, fine granules, powders, tablets, hard capsules, soft capsules, syrups, emulsions, suspensions, solutions and the like, or intravenously, intramuscularly or subcutaneously administered in the form of injections. Further, they may also be used in the form of suppositories. They may also be formed into powders which can be converted into solutions or the like for injection before use. There can be used pharmaceutical organic or inorganic solid or liquid carriers or diluents which are suitable for oral, intestinal or parenteral administration for preparing the drugs of the present invention. As the excipient used for preparing solid preparations, for example, there can be used lactose, sucrose, starch, talc, cellulose, dextrin, kaoline, calcium carbonate and the like. Liquid preparations for oral administration, i.e. emulsions, syrups, suspensions, solutions, etc. contain inert diluents which are normally used, e.g. water, vegetable oil, etc. This preparation can contain adjuvants such as humectants, suspension auxiliary agents, sweeteners, aromatics, colorants, preservatives, etc., in addition to inert diluents. The resulting liquid preparations may be contained in a capsule of an absorbable substance such as gelatin. As the solvent or suspending agent used for preparing preparations for parenteral administration, i.e. injections, suppositories, etc., for example, there can be used water, propylene glycol, polyethylene glycol, benzyl alcohol, ethyl oleate, lecithin and the like. As the base used for preparing suppositories, for example, there can be used cacao butter, emulsified cacao butter, laurin tallow, witepsol and the like. Preparations may be prepared by a conventional method.

The clinical dose varies depending upon age, pathology, condition of diseases and the like. For example, in the case of administering orally to an adult patient, the compounds of the present invention are normally administered with a dairy dose of about 0.01 to 1000 mg, preferably 10 to 1000 mg. The pharmaceutical composition of the present invention may be administered 1 to 3 times per day or administered intermittently with the above dairy dose.

When using as injections, it is advantageous that the compounds of the present invention are administered continuously or intermittently to an adult patient with a single dose of 0.001 to 100 mg.

The prolineamide derivatives of the present invention or the salts thereof have a strong inhibition activity to proteases such as thrombin, trypsin and the like. The compounds of the present invention are also superior in oral absorptive action so that they are useful as oral antithrombin agents, i.e. oral anticoagulants, or oral antitrypsin agents, i.e. remedy for pancreas diseases such as pancreatitis.

The following Examples and Experimental Examples further illustrate the present invention in detail but are not to be construed to limit the scope thereof.

The conventional abbreviations used in Examples are as follows: THF: tetrahydrofuran, DMF: N,N-dimethylformamide, DMSO: dimethyl sulfoxide, CDI: carbonyldiimidazole, DPPA: diphenylphosphorylazide, Z: benzyloxycarbonyl, Boc: tertiary butyloxycarbonyl.

Further, NMR in physical properties stands for a nuclear magnetic resonance spectrum and the numeral is ⊕ value in ppm, which is conventionally used for indicating the chemical shift. TMS (tetramethylsilane) was used as the internal standard. Further, the numeral shown in parenthesis following δ value is the number of hydrogen atoms, and the indications following the number of hydrogen atoms mean that s is singlet, d is doublet, t is triplet, q is quartet, m is multiplet, or is broad absorption peak, respectively.

IR stands for an infrared spectrum and measured as potassium bromide tablets unless otherwise stated. The numerical means the wave number in $cm^{-1}$. Only main absorption peak was shown. Further, mp means the non-corrected melting point in °C.

EXAMPLE 1

Synthesis of 4-amidino-[(S)-N-((R)-2-methylsulfonylamino-cyclohexylacetyl) prolyl] aminomethylbenzene (compound No. 105 of Table 1) hydrochloride (a) N-4-cyanobenzylphthalimide To a solution of potassium phthalimide (76 g, 410 mmol) in DMF (250 ml), a solution of 4-cyanobenzyl bromide (73 g, 373 mmol) in THF (250 ml) is added and stirred at 50° C for 3 hours.

Water (500 ml) is added to then mixture and a precipitated crystal was collected. Then, the crystal is washed with water and dried to give 96 g of the titled compound (99%). mp: 189°–191° C.

(b) 4-Cyano-[(S)-prolyl]aminomethylbenzene hydrochloride

To a solution of the compound (39 g, 150 mmol) obtained in the item (a) in methanol (250 ml), hydrazine hydrate (9 ml) is added and refluxed for 6 hours. After the solvent is evaporated, an aqueous 40% sodium hydroxide solution (300 ml) is added to the residue and stirred.

The reaction mixture is extracted with toluene and the organic layer is washed once with water and saturated brine, successively, and then dried over sodium sulfate. The solvent is evaporated and the resulting crude product (15 g, 73%) is used for the next step.

To a solution of (S)-N-Boc-proline (23.7 g, 110 mmol) in THF (250 ml), CDI (17.8 g, 110 mmol) is added at 0° C.

After the reaction solution is stirred for 2 hours, a solution of the crude product obtained in the above reaction in THF (150 ml) is added. After stirring for 6 hours, the solvent is evaporated and water (300 ml) is added to the residue. The mixture is extracted with chloroform and the organic layer is washed three times with water and once with saturated brine, successively. After drying over sodium sulfate, the solvent is evaporated and the residue is purified with silica gel chromatography (hexane-ethyl acetate).

The resulting oily product is dissolved in ethyl acetate (100 ml) and a 4N-hydrochloride in ethyl acetate (69 ml) is added and the mixture is stirred at 0° C. for 3 hours. The precipitated white solid is collected, washed with ethyl acetate and dried under reduced pressure to give 25.9 g of the titled compound (89%).

NMR (DMSO-$d^6$) 1.80–1.96 (m, 3H), 2.30–2.40 (m, 1H), 3.21 (br, 2H), 4.26 (br, 1H), 4.44 (d, 2H), 7.49 (d, 2H), 7.82 (d, 2H), 8.59 (br, 1H), 9.39 (t, 1H), 10.07 (br, (c) 4–Cyano-[(S)-N-((R)-2-t-butyloxycarbonylamino-cyclohexylacetyl) prolyl]aminomethylbenzene To a solution of the product (21 g, 79 mmol) obtained in the item (b) and (R)-N-t-butyloxycarbonylcyclohexylglycine (20.4 g, 79 mmol) in DMF (200 ml), a solution of triethylamine (22 ml, 159 mmol) and DPPA (22 g, 79 mmol) in DMF (50 ml) is added at 0° C. The mixture is allowed to stand at room temperature and then stirred for 12 hours. Water (400 ml) is added to the reaction mixture which is extracted with toluene-ethyl acetate (1:2). The organic layer is washed three times with water and once with saturated brine, successively, and then dried over sodium sulfate. After the solvent is evaporated, the residue is purified with silica gel chromatography (chloroform-methanol) to give 26.7 g of the titled compound (72%).

NMR (CDCl$_3$) 1.01–1.43 (m, 15H), 1.65–2.38 (m, 9H), 3.57 (q, 1H), 3.96–4.06 (m, 2H), 4.47 (dq, 2H), 4.69 (d, 1H), 5.12 (d, 1H), 7.35 (d, 2H), 7.59 (d, 2H), 7.73 (t, 1H)

(d) 4–Cyano-[(S)-N-((R)-2-methylsulfonylamino-cyclohexylacetyl)prolyl]aminomethylbenzene To a solution of the compound (26.7 g, 57 mmol) obtained in the item (c) in chloroform (50 ml), a 4-N hydrochloride in ethyl acetate (30 ml) is added at 0° C. The mixture is stirred for 3 hours and then the solvent is evaporated. The resulting residue was dissolved in dichloromethane (250 ml) and triethylamine (19 ml) is added. Then, a solution of methanesulfonyl chloride (7.9 g, 68 mmol) in dichloromethane (50 ml) is added at 0° C. and the mixture is stirred for 3 hours. The organic layer is washed once with a saturated sodium bicarbonate solution, water and saturated brine, successively, and then dried over sodium sulfate. The resulting residue is purified with silica gel chromatography (hexane-ethyl acetate) to give 18.6 g of the titled compound (73%).

NMR (CDCl$_3$) 0.9–1.29 (m, 5H), 1.60–1.85 (m, 5H), 2.0–2.4 (m, 5H), 2.89 (s, 3H), 3.55 (q, 1H), 3.80–3.88 (m, 2H), 4.43 (d, 2H), 4.61 (d, 2H), 5.60 (d, 2H), 7.31 (t, 1H), 7.37 (d, 2H), 7.60 (d, 2H)

(e) 4-Amidino-[(S)-N-((R)-2-methylsulfonylamino-cyclohexylacetyl) prolyl]aminomethylbenzene chloride To a solution of the compound (18.6 g, 42 mmol) obtained in the item (d) in chloroform (100 ml), a 37% hydrochloride in ethanol (100 ml) is added at 0° C. The mixture is allowed to stand at 0° C. for 48 hours and then the solvent is evaporated. The resulting residue is dissolved in methanol (100 ml) and ammonium carbonate (16 g, 166 mmol) is added at 0° C. After stirring for 6 hours, the solvent is evaporated and the resulting residue is purified with silica gel chromatography (chloroform-methanol) to give 5.2 g of the titled compound (73%).

NMR (DMSO-$d^6$) 9.39 (br, 4H), 8.66 (t, 1H), 7.81 (d, 2H), 7.48 (d, 2H), 7.40 (m, 1H), 4.47–4.14 (m, 3H), 3.90 (m, 1H), 3.71 (m, 1H), 3.59 (m, 1H), 2.79 (s, 3H), 2.13 (m, 1H), 1.88 (m, 3H), 1.69–1.53 (m, 5H), 1.14 (m, 6H)

IR: 3366, 2930, 2855, 1636, 1541, 1489, 1451, 1152

According to the same procedures described above, the compounds shown in the following Examples were synthesized.

EXAMPLE 2

4-Amidino-[(S)-N-[(R)-2-methylsulfonylamino-4,4-dimethylpentanoyl]prolyl]aminomethylbenzene (compound No. 104 of Table 1) methanesulfonate NMR (DMSO-$d^6$) 9.31 (br, 2H), 9.11 (br, 2H), 8.60 (t, 1H), 7.76 (d, 2H), 7.47 (d, 2H), 7.42 (d, 2H), 4.50–4.06 (m, 4H), 3.49 (m, 1H), 3.71 (m, 1H), 2.71 (s, 3H), 2.40 (s, 3H), 2.13 (m, 1H), 1.98 (m, 2H), 1.84 (m, 1H), 1.48 (d, 2H), 0.98 (s, 9H)

IR: 3274, 2957, 1640, 1208, 1150, 1049

EXAMPLE 3

4-Amidino-[(S)-N [(R)-2-methylsulfonylamino-3-cyclohexylpropionyl]prolyl]aminomethylbenzene (compound No. 106 of Table 1) hydrochloride NMR (DMSO-$d^6$) 9.41 (br, 2H), 9.20 (br, 2H), 8.68 (t, 1H), 7.78 (d, 2H), 7.47 (d, 2H), 7.47 (d, 2H), 4.49–4.23 (m, 3H), 4.13 (m, 1H), 3.69 (m, 1H), 3.48 (m, 1H), 2.72 (s, 3H), 2.12 (m, 1H), 1.97 (m, 1H), 1.83 (m, 2H), 1.64 (m, 5H), 1.40 (m, 2H), 1.19 (m, 4H), 0.94 (m, 2H)

IR: 3366, 2924, 1640, 1543, 1489, 1449, 1422

EXAMPLE 4

4-Amidino-[(S)-N [(R)-N'-methylsulfonylphenylalanyl]prolyl] aminomethylbenzene (compound No. 108 of Table 1) methanesulfonate NMR (DMSO-$d^6$) 9.31 (br, 2H), 9.08 (br, 2H), 8.57 (t, 1H), 7.75 (d, 2H), 7.71 (d, 1H), 7.47 (d, 2H), 7.29 (m, 5H), 4.52–4.21 (m, 3H), 3.54 (m, 2H), 3.28 (m, 2H), 3.04 (m, 1H), 2.90 (m, 2H), 2.71 (s, 3H), 2.50 (s, 3H), 1.88 (m, 2H)

IR: 3375, 1663, 1630, 1454, 1327, 1225, 1154, 1046

EXAMPLE 5

4-Amidino-[(S)-N-[(R)-N'-methylsulfonylmethionyl]prolyl] aminomethylbenzene (compound No. 110 of Table 1) hydrochloride NMR (DMSO-$d^6$) 9.45 (br, 2H), 9.26 (br, 2H), 8.68 (t, 1H), 7.80 (d, 2H), 7.55 (d, 2H), 7.48 (d, 2H), 4.44–4.17 (m, 4H), 3.70 (m, 1H), 3.59 (m, 1H), 2.87 (s, 3H), 2.56 (m, 3H), 2.13 (m, 1H), 2.08 (s, 3H), 1.97–1.63 (m, 4H)

IR: 3368, 1638, 1543, 1489, 1426, 1314, 1150

EXAMPLE 6

4-Amidino-[(S)-N-((R)-N'-formylphenylalanyl) prolyl]aminomethylbenzene (compound No. 94 of Table 1) hydrochloride NMR (DMSO-$d^6$) 9.56 (br, 2H), 9.36 (br, 2H), 8.97 (t, 1H), 8.70–8.60 (m, 1H), 7.86 (d, 1H), 7.83 (d, 2H), 7.46 (d, 2H), 7.37–7.17 (m, 5H), 4.36–4.16 (m, 4H), 3.60–2.70 (m, 4H), 2.40–1.20 (m, 4H)

IR: 3370, 1647, 1541, 1489, 1454, 1404, 704

EXAMPLE 7

4-Amidino-[(S)-N-((R)-2-methylsulfonylamino-hexanoyl) prolyl]aminomethylbenzene (compound No. 109 of Table 1) methanesulfonate NMR (DMSO-$d^6$) 9.32 (br, 2H), 9.11 (br, 2H), 8.58 (t, 1H), 7.76 (d, 2H), 7.48 (d, 2H), 7.42 (d, 1H), 4.47–4.23 (m, 2H), 4.20–3.90 (m, 3H), 3.54–3.45 (m, 1H), 3.80–3.66 (m, 1H), 2.74 (s, 3H), 2.43 (s, 3H), 2.20–0.79 (m, 13H)

IR: 3272, 1638, 1543, 1424, 1316, 1206, 1155, 1047

EXAMPLE 8

4-Amidino-[(S)-N-((R)-2-methylsulfonylamino-4-(4'-methoxy-carbonyl-phenyl) butanoyl) prolyl] aminomethylbenzene (compound No.127 of Table 1) hydrochloride NMR (DMSO-$d^6$) 9.35–9.23 (m, 4H), 8.59 (t, 1H), 7.90 (d, 2H), 7.77 (d, 2H), 7.61 (d, 1H ), 7.47 (d, 2H), 7.40 (d, 2H), 4.44–4.21 (m, 3H), 4.07 (m, 1H), 3.84 (s, 3H), 3.48 (m, 2H), 2.92–2.63 (m, 3H), 2.77 (s, 3H), 2.12 (m, 1H), 1.84 (m, 4H)

IR: 3370, 1638, 1541, 1489, 1437, 1287, 1150

EXAMPLE 9

4-Amidino-[(S)-N-[(R)-2-methylsulfonylamino-3-(3'-carboxyphenoxy) propanoyl]prolyl] aminomethylbenzene (compound No. 130 of Table 1) hydrochloride NMR (DMSO-$d^6$) 9.35 (br, 4H), 8.64 (t, 1H), 7.78 (d, 2H), 7.71 (d, 1H), 7.58–7.40 (m, 5H), 7.20 (m, 1H), 4.62 (m, 1H), 4.36 (m, 3H), 4.22 (m, 2H), 3.72 (m, 2H), 2.89 s, 3H), 2.12 (m, 1H), 1.94 (m, 3H)

IR: 3856, 1644, 1543, 1489, 1449, 1316, 1256, 1154

EXAMPLE 10

4-Amidino-[(S)-N-[(R)-2-methylsulfonylamino-3-(2'-benzyloxycarbonylphenoxy) propanoyl]prolyl] aminomethylbenzene (compound No. 123 of Table 1) hydrochloride NMR (DMSO-$d^6$) 9.24 (br, 4H), 8.60 (t, 1H), 7.77 (d, 2H), 7.71 (m, 1H), 7.57 (m, 1H), 7.49–7.35 (m, 8H), 7.16 (d, 1H), 7.07 (t, 1H), 5.29 (s, 2H), 4.62 (t, 1H), 4.37 (m, 3H), 4.28 (m, 1H), 4.17 (t, 1H), 3.67 (m, 2H), 2.91 (s, 3H), 2.15 (m, 1H), 1.88 (m, 3H)

IR: 3366, 1642, 1491, 1451, 1314, 1248, 1082

EXAMPLE 11

4-Amidino-[(S)-N-[(R)-2-ethoxycarbonylamino-3-methyl-3methylthiobutanoyl]prolyl] aminomethylbenzene (compound No. 98 of Table 1) hydrochloride NMR (DMSO-$d^6$) 8.89 (br, 2H), 8.66 (br, 2H), 7.77 (d, 2H), 7.33 (d, 2H), 6.27 (d, 1H), 4.65 (m, 1H), 4.46 (d, 1H), 4.37 (m, 2H), 3.97–3.72 (m, 4H), 2.62 (m, 1H), 2.15 (br, 3H), 2.04 (s, 3H), 1.40 (s, 3H), 1.36 (s, 3H), 1.05 (t, 3H)

IR: 3323, 2926, 1635, 1535, 1439, 1242, 1055

EXAMPLE 12

4-Amidino-[(S)-N-[(R)-2-carboxymethylsulfonylaminoheptanoyl]prolyl] aminomethylbenzene (compound No. 152 of Table 1) hydrochloride NMR (DMSO-$d^6$) 9.80 (br, 2H), 9.23 (br, 2H), 8.80 (t, 1H), 7.69 (d, 2H), 7.42 (d, 2H), 7.23 (d, 1H), 4.51–4.17 (m, 5H), 3.70 (m, H), 2.11 (m, 1H), 1.92 (m, 3H), 1.57–1.28 (m, 8H), 0.87 (m, 3H)

IR: 3366, 2957, 1636, 1543, 1489, 1416, 1318, 1136

EXAMPLE 13

4-Amidino-[(S)-N-(4-phenylbutanoyl)prolyl] aminomethylbenzene (compound No. 3 of Table 1) hydrochloride NMR (DMSO-$d^6$) 9.39 (br, 2H), 9.22 (br, 2H), 8.55 (t, 1H), 7.80 (d, 2H), 7.48 (d, 2H), 7.31–7.13 (m, 5H), 4.37–4.30 (m, 3H), 3.60–3.30 (m, 2H), 2.60 (t, 2H), 2.34–1.75 (m, 8H)

IR: 3264, 1618, 1541, 1491, 1451, 702

EXAMPLE 14

4-Amidino-[(S)-N-(2-benzyloxyacetyl)prolyl] aminomethylbenzene (compound No. 55 of Table 1) hydrochloride NMR (DMSO-$d^6$) 9.41 (br, 2H), 9.23 (br, 2H), 8.66 (t, 1H), 7.80 (d, 2H), 7.49 (d, 2H), 7.42–7.27 (m, 5H), 4.61–4.08 (m, 7H), 3.56–3.40 (m, 2H), 2.20–1.78 (m, 4H)

IR: 3262, 1645, 1539, 1489, 1454, 740

EXAMPLE 15

Trans-4-amidino-[(S)-N-[(R)-2-ethoxycarbonylamino-4,4-dimethylpentanoyl]prolyl] aminomethylcyclohexane (compound No. 263 of Table 1) hydrochloride (a) Trans-4-N-benzyloxycarbonylaminomethyl-cyclohexylnitrile To a solution of trans-4-aminomethylcyclohexanecarboxylic acid (25 g, 159 mmol) and sodium carbonate (20 g, 191 mmol) in water (300 ml), benzyloxycarbonyl chloride (27 ml, 190 mmol) is added at 0° C. After stirring for 6 hours, 1N-hydrochloric acid is added until the pH of the reaction mixture indicates 2, and the precipitated white solid is collected, washed with water and dried. The resulting white solid is dissolved in THF (300 ml) and CDI (21 g, 130 mmol) is added at 0° C. After stirring for 3 hours, the reaction mixture is added dropwise to a mixed solution of 33% ammonia in water (50 ml) and THF (150 ml) at 0° C. After stirring for 5 hours, the solvent is evaporated and water (500 ml) is added, and the precipitated white solid is collected, washed with water and dried.

To a solution of the resulting compound in 1,2-dichloroethane (500 ml), thionyl chloride (19 ml, 260 mmol) is added and heated to an inner temperature of 70° C. After stirring for 5 hours, the reaction mixture is poured into ice water and neutralized with an aqueous 1N-sodium hydroxide solution. After extracting with chloroform, the organic layer is washed twice with water and once with saturated brine, successively, and then dried over sodium sulfate. The solvent is evaporated and the resulting crude product is recrystallized (hexane-ethyl acetate) to give 22.8 g of the titled compound (53%). mp: 90°–92° C.

(b) Trans-4-(S)-prolylaminomethyl-cyclohexylnitrile

The compound obtained in the item (a) is dissolved in ethanol (250 ml) and the catalytic hydrogenation is conducted at room temperature and atomspheric pressure in the presence of palladium black (1 g). After the completion of the reaction, the catalyst is filtered off and the solvent is evaporated.

To a solution of (S)-N-benzyloxycarbonylproline (20.7 g, 83 mmol) in THF (150 ml), CDI (13.5 g, 83 mmol) is added at 0° C. After stirring for 3 hours, a solution of the compound obtained in the above reaction in THF (200 ml) is added at 0° C. After stirring for 12 hours, the solvent is evaporated, and chloroform (400 ml) is added to the resulting residue. The organic layer is washed three times with water and once with saturated brine, successively, and then dried over sodium sulfate. The solvent is evaporated and the resulting residue is purified with silica gel chromatography (chloroform-methanol).

The resulting compound is dissolved in ethanol (250 ml) and the catalytic hydrogenation is conducted at room temperature and atmospheric pressure in the presence of palladium black (1 g). After the completion of the reaction, the catalyst is filtered off and the solvent is evaporated to give 18.8 g of the titled compound (95%).

NMR (DMSO-$d^6$) 0.88–1.06 (m, 2H), 1.38–1.52 (m, 3H), 1.68–2.03 (m, 7H), 2.20–2.40 (m, 1H), 2.52–2.67 (m, 1H), 2.80–3.20 (m, 4H), 4.03–4.10 (m, 1H), 7.53 (br, 1,H), 8.65–8.70 (m, 1H)

(c) Trans-4-amidino-[(S)-N-[(R)-2-ethoxycarbonylamino-4, 4-dimethylpentanoyl]prolyl]aminomethylcyclohexane hydrochloride According to the same manner as that described in the items (c) to (e) of Example 1, the titled compound can be synthesized from the compound obtained in the item (b) and (R)-2-t-butyloxycarbonylamino-4,4-dimethylpentanoic acid.

NMR (DMSO-$d^6$) 8.95 (br, 2H), 8.69 (br, 2H), 7.60 (br, 1H), 6.32 (br, 1H), 4.56 (m, 1H), 4.39 (m, 1H), 4.18 (q, 2H), 4.10 (m, 1H), 3.52 (m, 1H), 3.19 (m, 1H), 2.89 (m, 1H), 2.69 (m, 1H), 2.14–1.59 (m, 12H), 1.26 (t, 3H), 0.98 (s, 9H), 0.98–0.89 (m, 2H)

IR: 3314, 2954, 1686, 1639, 1543, 1449, 1250, 1059

According to the same procedures, the compounds shown in the following Examples were synthesized.

EXAMPLE 16

Trans-4-amidino-[(S)-N-[(R)-2-ethoxycarbonylamino-3-cyclohexylpropanoyl] prolyl]aminoethylcyclohexane (compound No. 227 of Table 1) hydrochloride NMR (DMSO-$d^6$) 8.93 (br, 2H), 8.81 (br, 2H), 7.53 (br, 1H), 7.38 (t, 1H), 4.50–4.15 (m, 1H), 4.10–3.90 (m, 2H), 3.73–3.17 (m, 2H), 3.05–2.80 (m, 3H), 2.39 (br, 1H), 2.00–0.68 (m, 29H)

IR: 3297, 2926, 2853, 1684, 1543, 1449, 1262, 1053

EXAMPLE 17

Trans-4-amidino-[(S)-N-[(R)-2-isopropoxycarbonylamino-4,4-dimethylpentanoyl] prolyl]aminomethylcyclohexane (compound No. 265 of Table 1) hydrochloride NMR (DMSO-$d^6$) 8.91 (br, 2H), 8.78 (br, 2H), 7.55 (br, 1H), 7.28 (t, 1H), 4.78–4.70 (m, 1H), 4.30–3.92 (m, 1H), 3.80–3.20 (m, 3H), 3.0–2.75 (m, 2H), 2.50–1.37 (m, 14H), 1.18–1.00 (m, 6H), 1.0–0.81 (m, 1H)

IR: 3285, 2953, 2870, 1684, 1541, 1449, 1250, 1111

EXAMPLE 18

Trans-4-amidino-[(S)-N-((R)-N'-methylsulfonylphenylalanyl) prolyl] aminomethylcyclohexane (compound No. 250 of Table 1) hydrochloride NMR (DMSO-$d^6$) 8.88 (br, 2H), 8.75 (br, 2H), 7.85 (t, 1H), 7.65 (d, 1H), 4.27 (m, 1H), 4.16 (m, 1H), 3.51–3.41 (m, 4H), 2.99–2.70 (m, 4H), 2.78 (s, 3H), 2.38 (t, 1H), 1.90–1.40 (m, 9H), 1.08–0.87 (m, 2H)

IR: 3375, 2930, 1637, 1452, 1309, 1149, 1097, 983

EXAMPLE 19

Trans-4-amidino-[(S)-N-((R)-N'-methylsulfonylleucyl) prolyl] aminomethylcyclohexane (compound No. 269 of Table 1) hydrochloride NMR (DMSO-$d^6$) 8.89 (br, 2H), 8.85 (br, 2H), 6.56 (d, 1H), 4.53 (m, 1H), 4.17 (m, 1H), 3.86 (m, 1H), 3.47 (m, 1H), 3.07 (m, 2H), 2.97 (s, 3H), 2.13–1.80 (m, 10H), 1.63–1.54 (m, 4H), 1.33 (m, 1H), 0.98–0.87 (m, 2H), 0.97 (d, 6H)

IR: 3261, 2932, 1639, 1450, 1313, 1143, 1087, 985

EXAMPLE 20

Trans-4-amidino-[(S)-N-((R)-2-methylsulfonylamino-3-cyclohexyl-propanoyl) prolyl]aminomethylcyclohexane (compound No. 230 of Table 1) hydrochloride NMR (DMSO-$d^6$) 8.95 (br, 2H), 8.53 (br, 2H), 7.27 (m, 1H), 6.51 (d, 1H), 4.51 (m, 1H), 4.19 (m, 1H), 3.83 (m, 1H), 3.66 (m, 1H), 3.41 (m, 2H), 3.04 (m, 2H), 3.04 (m, 2H), 2.95 (s, 3H), 2.46 (t, 1H), 2.12–0.92 (m, 24H)

IR: 3265, 2926, 1639, 1545, 1448, 1315, 1143, 985

EXAMPLE 21

Trans-4-amidino-[(S)-N-((R)-2-isopropoxycarbonylamino-2-cyclohexylacetyl) prolyl]aminomethylcyclohexane (compound No. 228 of Table 1) hydrochloride NMR (DMSO-$d^6$) 8.91 (br, 2H), 8.69 (br, 2H), 7.36 (br, 1H), 5.99 (d, 1H), 4.84–4.79 (m, 1H), 4.58 (br, 2H), 4.53–4.50 (m, 2H), 4.10–3.90 (m, 2H), 3.60–3.40 (m, 1H), 2.50–0.97 (m, 30H)

IR: 3297, 2980, 2930, 2855, 1684, 1539, 1451, 1258

EXAMPLE 22

Trans-4-amidino-[(S)-N-((R)-2-ethoxycarbonylamino-4-ethyl-hexanoyl) prolyl] aminomethylcyclohexane (compound No. 264 of Table 1) hydrochloride NMR (DMSO-$d^6$) 8.91 (br, 2H), 8.70 (br, 2H), 7.54 (m, 1H), 6.34 (m, 1H), 4.56 (m, 1H), 4.38 (m, 1H), 4.11 (m, 3H), 3.48 (m, 1H), 3.21 (m, 1H), 2.88 (m, 1H), 2.68 (m, 1H), 2.30–1.19 (m, 18H), 1.26 (t, 3H), 0.96 (m, 2H), 0.86 (t, 6H)

IR: 3279, 2962, 1685, 1639, 1541, 1448, 1257, 1059, 752

EXAMPLE 23

Trans-4-amidino-[(S)-N-[(R)-2-t-butoxycarbonylamino-4,4-dimethylpentanoyl]prolyl] aminomethylcyclohexane (compound No. 266 of Table 1) glycolate NMR (DMSO-$d^6$) 9.54 (br, 2H), 8.72 (br, 2H), 7.54 (br, 1H), 7.01 (t, 1H), 4.60–4.00 (m, 4H), 3.40 (m, 2H), 3.10–2.75 (m, 3H), 2.35 (br, 1H), 2.00–1.20 (m, 24H), 0.91 (s, 9H)

IR: 3316, 2953, 1686, 1543, 1449, 1368, 1167

EXAMPLE 24

4-[(S)-N-[(R)-2-t-butyloxycarbonylamino-cyclohexylacetyl]prolyl]aminomethyl-benzamidoxime (compound No. 396 of Table 1)

To a solution of the compound (0.94 g, 2 mmol) obtained in the item (c) of Example 1 in ethanol (15 ml), a solution of sodium carbonate (0.17 g, 1.6 mmol) in water (3 ml) and hydroxyamine hydrochloride (0.22 g, 3.2 mmol) are added. After the reaction mixture is heated at reflux for 8 hours, the solvent is evaporated and the resulting residue is purified with silica gel column chromatography (chloroform-methanol) to give 0.84 g of the titled compound (84%).

NMR (CDCl$_3$) 1.0–1.49 (m, 14H), 1.5–2.4 (m, 1 OH), 3.56 (br, 1H), 3.97 (br, 1H), 4.09 (t, 1H), 4.41 (dq, 2H), 4.67 (d, 1H), 4.94 (br, 2H), 5.41 (d, 1H), 7.20 (d, 2H), 7.23–7.27 (m, 1H), 7.50 (d, 2H), 7.75 (br, 1H)

IR: 3345, 2978, 2930, 2855, 1640, 1528, 1449, 1167

According to the same procedures, the compounds shown in the following Examples were synthesized.

EXAMPLE 25

4-[(S)-N-phenylacetylprolyl]aminomethyl-benzamidoxime (compound No. 374 of Table 1)

NMR (CDCl$_3$) 8.11 (t, 1H), 7.37 (d, 2H), 7.28–7.23 (m, 5H), 7.08 (d, 2H), 4.88 (s, 2H), 4.68 (d, 1H), 4.51 (m, 1H), 4.21 (m, 1H), 3.71 (s, 2H), 3.63–3.51 (m, 2H), 2.40–2.01 (m, 4H)

IR: 3315, 2968, 1637, 1543, 1244, 1155, 927, 709

EXAMPLE 26

4-[(S)-N-[(R)-N'-ethoxycarbonylphenylalanyl]prolyl]aminomethylbenzamidoxime (compound No. 387 of Table 1)

NMR (CDCl$_3$) 7.54 (d, 2H), 7.27–7.19 (m, 7H), 6.31 (d, 1H), 5.05 (br, 2H), 4.65–4.42 (m, 3H), 4.24–4.1 0 (m, 1H), 3.80–3.40 (m, 3H), 3.10–2.95 (m, 2H), 2.60–2.50 (m, 1H), 2.14 (br, 1H), 1.95–1.50 (m, 3H), 0.99 (t, 3H)

IR: 3339, 1641, 1539, 1451, 1260, 752, 702

EXAMPLE 27

4-[(S)-N-[(R)-2-t-butyloxycarbonylamino-3-cyclohexylpropanoyl]prolyl]aminomethyl-benzamidoxime (compound No. 397 of Table 1)

NMR (CDCl$_3$) 7.75 (br, 1H), 7.50 (d, 2H), 7.21 (d, 2H), 5.40 (d, 1H), 4.94 (br, 2H), 4.64 (br, 1H), 4.40–4.25 (m, 3H), 3.95 (br, 1H), 3.50–3.40 (m, 1H), 2.0–0.80 (m, 26H)

IR: 3337, 2978, 2924, 2851, 1642, 1536, 1449, 1167

EXAMPLE 28

4-[(S)-N-[(R)-2-ethoxycarbonylamino-3-methyl-3-methylthiobutanoyl]prolyl]aminomethyl-benzamidoxime (compound No. 419 of Table 1)

NMR (CDCl$_3$) 7.66 (t, 1H), 7.53 (d, 2H), 7.23 (d, 2H), 5.64 (d, 1H), 4.91 (s, 2H), 4.68 (d, 1H), 4.58–4.30 (m, 3H), 3.90 (m, 1H), 3.87–3.76 (m, 2H), 3.62 (m, 1H), 2.37 (m, 1H), 2.09–2.00 (m, 3H), 2.06 (s, 3H), 1.41 (s, 3H), 1.39 (s, 3H), 1.09 (t, 3H)

IR: 3339, 2978, 1641, 1535, 1439, 1249, 1057, 929, 754

EXAMPLE 29

4-[(S)-N-[(R)-phenylalanyl]prolyl]aminomethyl-benzamidoxime (compound No. 390 of Table 1) dihydrochloride NMR (DMSO-d$^6$) 11.24 (br, 1H), 9.02 (br, 2H), 8.91 (t, 1H), 8.80 (br, 3H), 7.66 (d, 2H), 7.44 (d, 2H), 7.35–7.22 (m, 5H), 4.30–4.16 (m, 4H), 3.57–2.95 (m, 3H), 2.45–2.30 (m, 1H), 1.90–1.20 (m, 4H)

IR: 3059, 1649, 1539, 1491, 1454

EXAMPLE 30

Trans-4-[(S)-N-((R)-2-isopropoxycarbonylamino-2-cyclohexylacetyl) prolyl] aminomethylcyclohexanecarboxamidoxime (compound No. 430 of Table 1)

NMR (CDCl$_3$) 7.14 (br, 1H), 5.70 (d, 1H), 4.85–4.80 (m, 1H), 4.70 –4.50 (m, 3H), 4.17–4.08 (m, 2H), 3.96 (br, 1H), 3.54 (q, 1H), 3.05 (t, 2H), 2.40–2.20 (m, 1H), 2.09–0.88 (m, 30H)

IR: 3342, 2978, 2928, 2855, 1653, 1449, 1256, 1111

EXAMPLE 31

Trans-4-[(S)-N-((R)-2-t-butoxycarbonylamino-3-cyclohexylpropanoyl) prolyl] aminomethylcyclohexanecarboxamidoxime (compound No. 435 of Table 1)

NMR (CDCl$_3$) 7.14 (br, 1H), 5.40 (d, 1H), 4.60–4.33 (m, 5H), 3.88 (br, 1H), 3.43 (q, 1H), 3.20–3.11 (m, 1H), 3.0–2.96 (m, 1H), 2.40–2.30 (m, 1H), 2.0–0.84 (m, 35H)

IR: 3356, 2926, 2853, 1649, 1537, 1448, 1167

Trans-4-[(S)-N-((R)-2-t-butoxycarbonylamino-3-cyclohexylpropanoyl) prolyl] aminomethylcyclohexanecarboxamidoxime (compound No. 435 of Table 1)

NMR (CDCl$_3$) 7.15 (br, 1H), 5.28 (d, 1H), 4.58 (br, 4H), 4.09 (t, 1H), 3.92 (br, 1H), 3.53 (q, 1H), 3.20–2.90 (m, 2H), 2.40 (br, 1H), 2.10–0.91 (m, 33H)

IR: 3347, 2930, 2855, 1649, 1541, 1451, 1169

EXAMPLE 33

Trans-4-[(S)-N-[(R)-2-t-ethoxycarbonylamino-4,4-dimethylpentanoyl]prolyl] aminomethylcyclohexanecarboxamidoxime (compound No. 461 of Table 1)

NMR (CDCl$_3$) 7.06 (t, 1H), 5.56 (d, 1H), 4.57–4.39 (m, 4H), 4.11 (q, 2H), 3.98 (m, 1 H 3.47 (m, 1H), 3.05 (m, 2H), 2.39 (m, 1H), 2.04–1.78 (m, 1OH), 1.57 (d, 2H), 1.56–1.12 (m, 2H), 1.24 (t, 3H), 0.99 (s, 9H), 0.99–0.89 (m, 2H)

IR: 3356, 2934, 1649, 1541, 1446, 1249, 1059, 927

EXAMPLE 34

Trans-4-[(S)-N-[(R)-2-methoxycarbonylamino-4,4-dimethylpentanoyl]prolyl] aminomethylcyclohexanecarboxamidoxime (compound No. 458 of Table 1)

NMR (CDCl$_3$) 7.04 (t, 1H), 5.53 (d, 1H), 4.68 (s, 2H), 4.56 (d, 1H), 4.43 (m, 1H), 3.98 (m, 1H), 3.66 (s, 3H), 3.47 (m, 1H), 3.07 (m, 2H), 2.39 (m, 1H), 2.19–1.77 (m, 8H), 1.57 (d, 2H), 1.55–1.25 (m, 4H), 0.99 (s, 9H), 0.93 (m, 2H)

IR: 3344, 2949, 1712, 1649, 1548, 1448, 1249, 1059

EXAMPLE 35

Trans-4-[(S)-N-[(R)-2-t-butoxycarbonylamino-4,4-dimethylpentanoyl]prolyl] aminomethylcyclohexanecarboxamidoxime (compound No. 467 of Table 1)

NMR (CDCl$_3$) 7.12 (t, 1H), 5.14 (d, 1H), 4.58 (d, 1H), 4.53 (s, 2H), 4.37 (m, 1H), 3.92 (m, 1H), 3.45 (m, 1H), 3.19

(m, 1H), 2.95 (m, 1H), 2.42 (m, 1H), 2.06–1.79 (m, 8H), 1.53 (d, 2H), 1.52–1.34 (m, 4H), 1.43 (s, 9H), 0.99 (s, 9H), 1.00–0.89 (m, 2H)

IR: 3358, 2930, 1649, 1535, 1448, 1367, 1249, 1168

EXAMPLE 36

Trans-4-[(S)-N-[(R)-2-benzyloxycarbonylamino-4,4-dimethylpentanoyl]prolyl] aminomethylcyclohexanecarboxamidoxime
(compound No. 469 of Table 1)

NMR (CDCl$_3$) 7.36–7.27 (m, 5H), 7.04 (t, 1H), 5.63 (d, 1H), 5.16–5.00 (m, 2H), 4.58–4.46 (m, 4H), 3.97 (m, 1H), 3.47 (m, 1H), 3.06–2.9 2 (, 2H), 2.43–2.38 (m, 1H), 2.01–1.72 (m, 8H), 1.58 (d, 2H), 1.50–1.23 (m, 4H), 0.98 (s, 9H), 0.98–0.88 (m, 2H)

IR: 3356, 2928, 1649, 1541, 1448, 1249, 1053 929

EXAMPLE 37

Trans-4-[(S)-N-[(R)-2-isopropoxycarbonylamino-4,4-dimethylpentanoyl]prolyl] aminomethylcyclohexanecarboxamidoxime
(compound No. 464 of Table 1)

NMR (CDCl$_3$) 7.11 (t, 1H), 5.49 (d, 1H), 4.83 (m, 1H), 4.56 (m, 3H), 4.42 (dd, 1H), 3.98 (m, 1H), 3.47 (dd, 1H), 3.04 (m, 2H), 2.40 (m, 1H), 2.01 (m, 2H), 1.92 (m, 3H), 1.80 (m, 3H), 1.57 (d, 2H), 1.39 (m, 4H), 1.21 (m, 6H), 0.99 (s, 9H), 0.94 (m, 2H)

EXAMPLE 38

Trans-4-[(S)-N-[(R)-2-isopropoxycarbonylamino-2-cyclopentylacetyl]prolyl] aminomethylcyclohexanecarboxamidoxime
(compound No. 464 of Table 1)

NMR (CDCl$_3$) 7.14 (t, 1H), 5.42 (d, 1H), 4.83 (m, 1H), 4.60 (d, 1H), 4.52 (s, 2H), 4.13 (m, 1H), 3.98 (m, 1H), 3.56 (m, 1H), 3.04 (m, 2H), 2.35 (m, 1H), 2.24 (m, 1H), 2.10–1.30 (m, 20H), 1.23 (dd, 6H), 1.01–0.93 (m, 2H)

IR: 3344, 2934, 1649, 1541, 1448, 1275, 1111, 754

EXAMPLE 39

Trans-4-[(S)-N-((R)-2-t-butoxycarbonylamino-2-cyclopentylacetyl) prolyl] aminomethylcyclohexanecarboxamidoxime
(compound No. 432 of Table 1)

NMR (CDCl$_3$) 7.16 (t, 1H), 5.16 (d, 1H), 4.60 (d, 1H), 4.51 (s, 2H), 4.14 (t, 1H), 3.94 (m, 1H), 3.52 (m, 1H), 3.01 (m, 2H), 2.38 (m, 1H), 2.23–1.39 (m, 21H), 1.43 (s, 9H), 1.17–0.90 (m, 2H)

IR: 3350, 2932, 1649, 1541, 1448, 1367, 1251, 1167, 929

EXAMPLE 40

Trans-4-[(S)-N-((R)-2-ethoxycarbonylamino-3-cyclohexylpropanoyl) prolyl] aminomethylcyclohexanecarboxamidoxime
(compound No. 428 of Table 1)

NMR (CDCl$_3$) 7.08 (br, 1H), 5.53 (d, 1H), 4.80–4.40 (m, 4H), 4.10–3.85 (m, 4H), 3.44 (q, 1H), 3.06 (t, 3H), 2.15–0.90 (m, 29H)

IR: 3343, 2926, 2853, 1649, 1541, 1449, 1260, 1053

EXAMPLE 41

Trans-4-[(S)-N-((R)-2-isopropoxycarbonylamino-3-cyclohexylpropanoyl) prolyl] aminomethylcyclohexanecarboxamidoxime
(compound No. 431 of Table 1)

NMR (CDCl$_3$) 7.12 (br, 1H), 5.51 (d, 1H), 4.85–4.70 (m, 1H), 4.60–4.30 (m, 4H), 4.0–3.85 (m, 1H), 3.44 (q, 1H), 3.10–2.95 (m, 3H), 2.45–2.35 (m, 1H), 2.05–0.80 (m, 32H)

IR: 3347, 2978, 2926, 2853, 1649, 1539, 1449, 1261, 1111

EXAMPLE 42

Trans-4-[(S)-N-((R)-2-isopropoxycarbonylamino-4-ethyl-hexanoyl) prolyl] aminomethylcyclohexanecarboxamidoxime
(compound No. 463 of Table 1)

NMR (CDCl$_3$) 7.11 (t, 1H), 5.41 (d, 1H), 4.83 (m, 1H), 4.56 (m, 3H), 4.39 (m, 1H), 3.94 (m, 1H), 3.46 (m, 1H), 3.02 (m, 2H), 2.39 (m, 1H), 2.10–1.20 (m, 20H), 1.22 (dd, 6H), 1.02–0.84 (m, 2H), 0.86 (t, 6H)

IR: 33346, 2962, 2930, 1653, 1541, 1448, 1271, 1113

EXAMPLE 43

Trans-4-[(S)-N-((R)-2-t-butoxycarbonylamino-4-ethyl-hexanoyl) prolyl] aminomethylcyclohexanecarboxamidoxime
(compound No. 466 of Table 1)

NMR (CDCl$_3$) 7.19 (t, 1H), 5.14 (d, 1H), 4.60 (d, 1H), 4.50 (s, 2H), 4.33 (m, 1H), 3.89 (m, 1H), 3.43 (m, 1H), 3.15 (m, 1H), 2.95 (m, 1H), 2.40 (m, 1H), 2.10–1.19 (m, 20H), 1.43 (s, 9H), 1.04–0.89 (m, 2H), 0.86 (t, 6H)

IR: 3346, 2964, 2930, 1649, 1541, 1448, 1367, 1280, 1251, 1168, 929

EXAMPLE 44

Trans-4-[(S)-N-((R)-2-ethoxycarbonylamino-heptanoyl) prolyl] aminomethylcyclohexanecarboxamidoxime
(compound No. 459 of Table 1)

NMR (CDCl$_3$) 7.08 (t, 1H), 5.60 (d, 1H), 4.58 (m, 3H), 4.35 (m, 1H), 4.07 (m, 2H), 3.92 (m, 1H), 3.48 (m, 1H), 3.06 (m, 2H), 2.40 (m, 1H), 2.04–1.32 (m, 20H), 1.24 (t, 3H), 0.89 (t, 3H), 0.98 (m, 2H)

IR: 3346, 2928, 1649, 1541, 1448, 1255, 1055, 927

EXAMPLE 45

Trans-4-[(S)-N-((R)-N'-t-butoxycarbonylamino-methionyl) prolyl] aminomethylcyclohexanecarboxamidoxime
(compound No. 468 of Table 1)

NMR (CDCl$_3$) 7.07 (m, 1H), 5.31 (d, 1H), 4.55 (m, 4H), 3.56 (m, 1H), 3.10 (m, 2H), 2.57 (t, 2H), 2.37 (m, 1H), 2.11 (s, 3H), 2.06–1.29 (m, 14H), 1.43 (s, 9H), 1.00 (m, 2H)

IR: 3354, 2928, 1647, 1541, 1448, 1367, 1251, 1167

EXAMPLE 46

Trans-4-[(S)-N-((R)-2-hydroxy-4,4-dimethyl-pentanoyl) prolyl] aminomethylcyclohexanecarboxamidoxime
(compound No. 454 of Table 1)

NMR (CDCl$_3$) 7.19 (t, 1H), 4.68 (s, 2H), 4.50 (d, 1H), 4.36 (t, 1H), 3.64 (t, 1H), 3.39 (m, 1H), 3.06 (m, 2H), 2.35

(m, 2H), 2.16–1.79 (m, 9H), 1.44 (d, 2H), 1.43–1.25 (m, 3H), 1.00–0.95 (m, 2H), 1.02 (s, 9H)

IR: 3337, 2944, 1653, 1620, 1566, 1448, 1386, 1248, 1087

EXAMPLE 47

Trans-4-[(S)-N-((R)-2-ethoxycarbonylamino-4-ethyl-hexanoyl) prolyl] aminomethylcyclohexanecarboxamidoxime (compound No. 460 of Table 1)

NMR (CDCl$_3$) 7.07 (t, 1H), 5.53 (d, 1H), 4.56 (m, 3H), 4.40 (m, 1H), 4.11 (q, 2H), 3.96 (m, 1H), 3.45 (m, 1H), 3.05 (m, 2H), 2.36 (m, 1H), 2.09–1.77 (m, 10H), 1.61–1.21 (m, 8H), 1.24 (t, 3H), 1.02–0.83 (m, 2H), 0.86 (t, 6H)

IR: 3342, 2962, 2930, 1649, 1541, 1448, 1379, 1269, 1059, 929

EXAMPLE 48

Trans-4-[(S)-N-[(R)-2-ethoxycarbonylamino-4,4-dimethylpentanoyl]prolyl] aminomethylcyclohexanecarboxamide O-methoxycarbonyloxime (compound No. 531 of Table 1)

To a solution of the compound (4.2 g, 8.9 mmol) obtained in Example 33 and triethylamine (1.9 ml, 13.3 mmol) in dichloromethane (100 ml), a solution of methyl chloroformate (1.0 g, 10 mmol) in dichloromethane (10 ml) is added at 0° C. After stirring for 4 hours, the organic layer is washed once with an aqueous saturated sodium bicarbonate solution, water and saturated brine, successively. After drying over sodium sulfate, the solvent is evaporated and the residue is purified with silica gel column chromatography (ethyl acetate-methanol) to give 2.9 g of the titled compound (62%).

NMR (CDCl$_3$) 0.89–1.07 (m, 11H), 1.21–1.60 (m, 8H), 1.79–2.40 (m, 9H), 3.0–3.10 (m, 2H), 3.40–3.50 (m, 1H), 3.84 (s, 3H), 3.84–4.20 (m, 3H), 4.35–4.40 (m,1H), 4.55 (d, 1H), 4.81 (br, 2H), 5.19 (d, 1H), 7.12 (t, 1H)

IR: 3345, 2953, 1763, 1699, 1645, 1541, 1443, 1256

According to the same procedures, the compounds shown in the following Examples were synthesized.

EXAMPLE 49

4-[(S)-N-((R)-2-hydroxy-2-cyclohexylacetyl) prolyl] aminomethylbenzamide O-ethoxycarbonyloxime (compound No. 543 of Table 1)

NMR (CDCl$_3$) 7.56 (d, 2H), 7.47 (t, 1H), 7.22 (d, 2H), 5.35 (s, 2H), 4.53 (m, 2H), 4.37 (d, 2H), 4.30 (q, 2H), 4.07 (m, 1H), 3.64 (m, 1H), 3.47 (m, 1H), 3.39 (m, 1H), 2.35–1.17 (m, 15H), 1.35 (t, 3H)

IR: 3368, 2928, 1772, 1628, 1554, 1452, 1404, 1228, 1087, 856

EXAMPLE 50

Trans-4-[(S)-N-((R)-2-hydroxy-4,4-dimethylpentanoyl) prolyl] aminomethylcyclohexanecarboxamide O-methoxycarbonyloxime (compound No. 534 of Table 1)

NMR (CDCl$_3$) 7.07 (t, 1H), 4.77 (s, 2H), 4.52 (d, 1H), 4.34 (m, 1H), 3.85 (s, 3H), 3.58 (t, 1H), 3.37 (m, 1H), 3.22 (d, 1H), 3.12–3.05 (m, 2H), 2.26–2.21 (m, 1H), 1.97–1.37 (m, 13H), 1.03 (s, 9H), 1.09–0.95 (m, 2H)

IR: 3346, 2953, 1763, 1643, 1442, 1257, 1089, 879

EXAMPLE 51

Trans-4-[(S)-N-((R)-2-hydroxy-4,4-dimethylpentanoyl)prolyl] aminomethylcyclohexanecarboxamide O-ethoxycarbonyloxime (compound No. 556 of Table 1)

NMR (CDCl$_3$) 7.05 (t, 1H), 4.73 (s, 2H), 4.52 (d, 1H), 4.34 (t, 1H), 4.27 (q, 2H), 3.58 (m, 1H), 3.45 (m, 1H), 3.08 (m, 2H), 2.44 (m, 1H), 2.30–1.30 (m, 13H), 1.32 (t, 3H), 1.03 (s, 9H), 1.07–0.92 (m, 2H)

IR: 3373, 2953, 1759, 1641, 1450, 1369, 1248, 1093

EXAMPLE 52

Trans-4-amino-[(S)-N-[(R)-N'-methanesulfonylphenyalanyl]prolyl] aminomethylcyclohexane (compound No. 776 of Table 1) L-tartrate.

(a) Trans-4-t-butyloxycarbonylamino-benzyloxycarbonylamino-methylcyclohexane

To a solution of trans-4-aminomethylcyclohexanecarboxylic acid (15.7 g, 100 mmol) and sodium hydroxide (4.0 g, 100 mmol) in water (30 ml), benzyloxycarbonyl chloride (15.6 ml, 110 mmol) and sodium hydroxide (4.4 g, 110 mmol) in water (30 ml) are added dropwise at 0° C., simultaneously. After stirring for 4 hours, the mixture is extracted once with ether and 1N-hydrochloric acid is added to the aqueous layer until the pH of the mixture indicates 2. Then, the precipitated white solid is collected and dried.

To a solution of the resulting compound (12.8 g, 50 mmol) in t-butanol (150 ml), triethylamine (8.3 ml, 60 mmol) and DPPA (13.7 g, 50 mmol) are added and heated at reflux for 8 hours. After the solvent is evaporated, water is added to the residue and the mixture is extracted with chloroform. The organic layer is washed once with an aqueous sodium carbonate (5%), once with an aqueous potassium hydrogensulfate (5%), twice with water and once with saturated brine, successively, and then dried over sodium sulfate. The solvent is evaporated and the residue is purified with silica gel column chromatography (hexane-ethyl acetate) to give 8.6 g of the titled compound (47%).

NMR (CDCl$_3$) 0.85–1.37 (m, 14H), 1.60–1.85 (m, 4H), 2.84 (t, 1H), 3.12 (br, 1H), 5.00 (s, 2H), 6.62 (d, 1H), 7.23–7.39 (m, 6H)

(b) Trans-4-t-butyloxycarbonylamino-[(S)-N-benzyloxycarbonylprolyl]aminomethylcyclohexane The compound (4.4 g, 12 mmol) obtained in the item (a) is dissolved in methanol (200 ml) and the catalytic hydrogenation is conducted at room temperature and under atomospheric pressure in the presence of palladium black (0.4 g). After the completion of the reaction, the catalyst is filtered off and the solvent is evaporated.

To a solution of (S)-Z-proline (3.0 g, 12 mmol) in THF (30 ml), CDI (2.0 g, 12 mmol) is added at 0° C. After stirring for 3 hours, a solution of the compound obtained in the above reaction in THF (150 ml) is added at 0° C. After stirring for 6 hours, the solvent is evaporated and water (50 ml) is added to the residue. The mixture is extracted with chloroform and the organic layer is washed three times with water and once with saturated brine, successively. After drying over sodium sulfate, the solvent is evaporated and the residue is purified with silica gel chromatography (chloroform-methanol) to give 4.2 g of the titled compound (77%).

NMR (CDCl$_3$) 0.85–1.06 (m, 4H), 1.44 (s, 9H), 1.60–2.35 (m, 9H), 2.94–3.20 (m, 2H), 3.20–3.55 (m, 3H), 4.31 (br, 1H), 4.47 (br, 1H), 5.14 (s, 2H), 6.90 (br, 1H), 7.15–7.40 (m, 5H)

(c) Trans-4-t-butyloxycarbonylamino-[(S)-N-[(R)-N'-benzyloxycarbonylphenylalanyl]prolyl] aminomethylcyclohexane The compound (3.6 g, 7.9 mmol) obtained in the item (b) is dissolved in methanol (50 ml) and the catalytichydrogenation is conducted at room temperature and under atomospheric pressure in the presence of palladium black (0.3 g). After the completion of the reaction, the catalyst is filtered off and the solvent is evaporated.

To a solution of (R)-Z-phenylalanine (2.4 g, 7.9 mmol) in THF (30 ml), CDl (1.3 g, 7.9 mmol) is added at 0° C. After stirring for 4 hours, a solution of the compound obtained in the above reaction in THF (60 ml) is added. After stirring for 8 hours, the solvent is evaporated and water is added to the reaction mixture. The mixture is extracted with chloroform and the organic layer is washed three times with water and once with saturated brine, successively, and then dried over sodium sulfate. The solvent is evaporated and the residue is purified with silica gel column chromatography (chloroform-methanol) to give 4.2 g of the titled compound (89%).

NMR (CDCl$_3$) 0.85–1.06 (m, 5H), 1.33–2.0 (m, 15H), 2.10–2.22 (m, 1H), 2.50–2.60 (m, 1H), 2.94–3.01 (m, 5H), 3.30 (br, 1H), 3.57 (t, 1H), 4.32–4.59 (m, 3H), 5.08 (d, 2H), 5.69 (d, 1H), 7.02 (br, 1H), 7.18–7.37 (m, 10H)

(d) Trans-4-amino-[(S)-N-[(R)-N'-methanesulfonylphenylalanyl]prolyl] aminomethylcyclohexane L-tartrate.

The compound (2.4 g, 3.9 mmol) obtained in the item (c) is dissolved in methanol (40 ml) and the catalytic hydrogenation is conducted at room temperature and under atomospheric pressure in the presence of palladium black (0.2 g). After the completion of the reaction, the catalyst is filtered off and the solvent is evaporated. To a solution of the resulting compound in dichloromethane (40 ml), triethylamine (0.65 ml, 4.7 mmol) is added and a solution of methanesulfonyl chloride (0.47 g, 4.1 mmol) in dichloromethane (100 ml) is further added at 0° C. After stirring for 3 hours, an aqueous saturated sodium bicarbonate solution is added and the organic layer is washed once with water and saturated brine, successively. After drying over sodium sulfate, the solvent is evaporated and the residue is purified with silica gel chromatography (chloroform-methanol).

The resulting compound is dissolved in chloroform (10 ml) and a 4N-dioxane hydrochloride in dioxane (10 ml) is added at 0° C. After stirring for 2 hours, the solvent is evaporated and chloroform (10 ml) and a 1N-sodium hydroxide solution (10 ml) are added to the residue and, further, the mixture is stirred for 10 minutes. The organic layer is dried over sodium sulfate and a solution of L-tartaric acid (0.34 g, 2.26 nm) in methanol (5 ml) is added.

The solvent is evaporated and ether (20 ml) is added, and then the precipitated white solid is collected and dried to give 1.36 g of the titled compound (58%).

NMR (DMSO-d$^6$) 7.77 (m, 4H), 7.28 (m, 5H), 4.28 (m, 1H), 4.16 (m, 1H), 3.57–3.45 (m, 8H), 2.73 (s, 3H), 1.91–1.75 (m, 9H), 1.54 (m, 1H), 1.25 (m, 4H), 0.93 (m, 2H)

IR: 3324, 2934, 1734, 1638, 1545, 1453, 1308, 1148

According to the same procedures, the compounds shown in the following Examples were synthesized.

EXAMPLE 53

Trans-4-amino-[(S)-N-[(R)-2-methylsulfonylamino-2-cyclohexylacetyl]prolyl]aminomethylcyclohexane (compound No. 759 of Table 1) hydrochloride NMR (DMSO-d$^6$) 8.09 (br, 3H), 7.80 (t, 1H), 7.39 (d, 1H), 4.30–4.26 (m, 1H), 3.87 (t, 1H), 3.80–3.45 (m, 2H), 3.0–2.80 (m, 3H), 2.85 (s, 3H), 2.10–0.80 (m, 24H)

IR: 3382, 2930, 2857, 1638, 1543, 1451, 1154

EXAMPLE 54

Trans-4-amino-[(S)-N-[(S)-N'-benzenesulfonyl-α-glutamyl]prolyl]aminomethylcyclohexane (compound No. 792 of Table 1) hydrochloride NMR (DMSO-d$^6$) 8.04 (br, 3H), 7.75–7.50 (m, 5H), 4.05 (q, 1H), 3.77–3.30 (m, 5H), 3.0–2.70 (m, 3H), 2.28 (t, 2H), 2.0–1.52 (m, 10H), 1.31–1.11 (m, 3H), 1.0–0.85 (m, 2H)

IR: 3400, 2937, 1637, 1449, 1161

EXAMPLE 55

Trans-4-amino-[(S)-N-((RS)-3-methylsulfonylamino-3-phenylpropanoyl) prolyl] aminomethylcyclohexane (compound No. 777 of Table 1) hydrochloride NMR (DMSO-d$^6$) 8.08 (m, 3H), 7.34 (m, 5H), 4.78 (m, 1H), 4.15 (m, 2H), 3.51 (m, 1H), 3.36 (m, 2H), 2.86 (m, 4H), 2.68 (s, 3H), 2.51 (m, 2H), 2.00–1.69 (m, 6H), 1.27 (m, 4H), 0.92 (m, 2H)

IR: 3409, 2936, 1638, 1453, 1314, 1148

EXAMPLE 56

Trans-4-amino-[(S)-N-((R)-2-isopropoxycarbonylamino-4,4-dimethylpentanoyl) prolyl]aminomethylcyclohexane (compound No. 797 of Table 1)

NMR (CDCl$_3$) 7.19 (m, 1H), 5.32 (d, 1H), 4.82 (m, 1H), 4.53 (m, 2H), 4.00 (m, 1H), 3.48 (m, 1H), 3.03–2.16 (m, 6H), 2.00–1.81 (m, 6H), 1.57 (d, 2H), 1.49 (m, 4H), 1.24 (m, 6H), 1.00 (s, 9H), 0.95 (m, 2H)

IR: 3326, 2949, 1640, 1541, 1449, 1248

EXAMPLE 57

Trans-4-amino-[(S)-N-((R)-N'-ethoxycarbonyl-phenylalanyl) prolyl]aminomethylcyclohexane (compound No. 780 of Table 1) hydrochloride NMR (DMSO-d$^6$) 7.98 (m, 3H), 7.37 (t, 1H), 7.26 (m, 5H), 4.37 (dd, 1H), 4.16 (m, 1H), 4.02 (m, 2H), 3.88 (m, 1H), 3.59 (m, 1H), 3.43 (m, 1H), 2.86 (m, 5H), 1.93–1.75 (m, 7H), 1.28 (m, 4H), 1.15 (t, 3H), 0.92 (m, 2H)

IR: 3349, 2936, 1642, 1537, 1451, 1258

EXAMPLE 58

Trans-4-amino-[(S)-((R)-phenylalanyl) prolyl] aminomethylcyclohexane (compound No. 779 of Table 1) hydrochloride NMR (DMSO-d$^6$) 8.69 (br, 3H), 8.09 (br, 4H), 7.37–7.20 (m, 5H), 4.19 (br, 1H), 4.09–4.06 (m, 1H), 3.20–2.82 (m, 5H), 2.0–0.85 (m, 15H)

IR: 3426, 2936, 1649, 1539, 1497, 1454

EXAMPLE 59

Trans-4-amino-[(S)-N-((R)-2-ethoxycarbonyloxy-3-phenylpropanoyl) prolyl]aminomethylcyclohexane (compound No. 785 of Table 1) hydrochloride NMR (DMSO-d$^6$) 7.78 (m, 3H), 7.30 (m, 5H), 7.15 (d, 1H), 5.22 (t, 1H), 4.20 (m, 1H), 4.08 (m, 3H), 3.64 (m, 1H), 3.02–2.88 (m, 5H), 1.92–1.72 (m, 7H), 1.20–0.94 (m, 9H)

IR: 3397, 2938, 1740, 1655, 1453, 1269

EXAMPLE 60

Trans-4-amino-[(S)-N-((R)-2-allylcarbamoyloxy-3-phenylpropanoyl) prolyl]aminomethylcyclohexane (compound No. 787 of Table 1) hydrobromide NMR (DMSO-d$^6$) 7.90 (m, 3H), 7.30 (m, 5H), 7.14 (m, 1H), 5.72 (m, 2H), 5.06 (m, 2H), 4.76 (m, 1H), 4.17 (m, 1H), 3.60 (m, 1H), 2.98–2.85 (m, 5H), 1.87–1.70 (m, 7H), 1.23 (m, 7H), 0.90 (m, 2H)

IR: 3364, 2936, 1707, 1645, 1543, 1454, 1256

EXAMPLE 61

Trans-4-amino-[(S)-N-((R)-2-hydroxy-2-cyclohexylacetyl) prolyl]aminomethylcyclohexane (compound No. 768 of Table 1) hydrochloride NMR (DMSO-d$^6$) 8.21 (br, 3H), 7.95 (m, 1H), 4.53 (m, 1H), 4.18 (d, 1H), 3.95 (m, 1H), 3.07 (m, 3H), 2.18–1.55 (m, 22H), 1.30–1.03 (m, 2H)

IR: 3422, 2928, 2854, 1637, 1450, 1388, 1240, 1114, 1045

EXAMPLE 62

Trans-4-amino-[(S)-N-((R)-2-hydroxy-2-phenylacetyl) prolyl]aminomethylcyclohexane (compound No. 783 of Table 1) hydrochloride NMR (DMSO-d$^6$) 7.98 (br, 3H), 7.37–7.28 (m, 5H), 5.48 (br, 1H), 5.23 (d, 1H), 4.23 (d, 1H), 3.70–3.35 (m, 2H), 3.0–2.80 (m, 4H), 2.0–1.60 (m, 8H), 1.40–0.90 (m, 5H)

IR: 3329, 2935, 1667, 1626, 1552, 1448

EXAMPLE 63

Trans-4-amino-[(RS)-1-((R)-N'-methylsulfonyl-phenylalanyl)-2-piperidinecarboxyl] aminomethylcyclohexane (compound No. 834 of Table 1) hydrochloride NMR (DMSO-d$^6$) 8.07 (m, 3H), 7.28 (m, 5H), 4.64 (m, 1H), 4.39 (m, 1H), 3.99 (m, 1H), 3.67 (m, 1H), 2.87 (m, 7H), 2.84 (s, 3H), 1.91–1.68 (m, 5H), 1.33–0.92 (m, 10H)

IR: 3385, 2936, 1638, 1535, 1453, 1314, 1150

EXAMPLE 64

Trans-4-amino-[(S)-N-[(R)-2-ethoxycarbonylamino-4,4-dimethylpentanoyl]prolyl] aminomethylcyclohexane (compound No. 794 of Table 1)

NMR (CDCl$_3$) 7.16 (m, 1H), 5.68 (d, 1H), 4.53 (d, 1H), 4.38 (m, 1H), 4.10 (q, 2H), 4.01 (m, 1H), 3.46–3.07 (m, 4H), 2.30–1.81 (m, 8H), 1.58 (m, 5H), 1.26 (t, 3H), 1.00 (s, 9H), 0.95 (m, 2H)

IR: 3329, 2949, 1642, 1541, 1447, 1248, 1059

EXAMPLE 65

Trans-4-(5-methyl-1,3-dioxo-2-on-4-ylmethyl)amino-[(S)-N-[(R)-2ethoxycarbonylamino-4,4-dimethylpentanoyl]prolyl]aminomethylcyclohexane (compound No. 968 of Table 1)

To a solution of the compound (5.4 g, 11.7 mmol) obtained in Example 64 in DMF (40 ml), sodium carbonate (3.2 g, 23.4 mmol) is added, and a solution of 4-bromomethyl-5-methyl-1,3-dioxo-2-on (4.0 g, 17.6 mmol) in DMF (5 ml) is further added at 0° C. After stirring for 48 hours, the solvent is evaporated and water is added to the residue, which is extracted with ethyl acetate. The organic layer is washed three times with water and once with saturated brine, successively, and then dried over sodium sulfate. The solvent is evaporated and the residue is purified with silica gel column chromatography (chloroform-methanol) to give 2.8 g of the titled compound (44%).

NMR (CDCl$_3$) 7.07 (m, 1H), 5.15 (d, 1H), 4.56 (d, 1H), 4.41 (m, 1H), 4.10 (q, 2H), 4.00 (m, 2H), 3.48 (s, 2H), 3.45 (m, 2H), 3.04 (t, 1H), 2.62 (m, 1H), 2.38 (m, 1H), 2.11 (s, 3H), 2.00 (m, 3H), 1.82 (m, 2H), 1.73–1.43 (m, 4H), 1.28 (t, 3H), 1.26 (m, 3H), 1.00 (s, 9H), 0.96 (m, 2H)

IR: 3329, 2934, 2870, 1823, 1649, 1539, 1445, 1223

According to the same procedures, the compounds shown in the following Examples were synthesized.

EXAMPLE 66

Trans-4-t-butoxycarbonylamino-[(S)-N-[(R)-N'-methanesulfonylphenylalanyl]prolyl] aminomethylcyclohexane (compound No. 955 of Table 1)

NMR (CDCl$_3$) 7.29 (m, 3H), 7.24 (m, 2H), 6.67 (t, 1H), 5.61 (d, 1H), 4.40 (m, 2H), 4.29 (dd, 1H), 3.58 (m, 1H), 3.34 (m, 1H), 2.99 (m, 4H), 2.82 (s, 3H), 2.69 (m, 1H), 2.18–1.74 (m, 9H), 1.43 (s, 9H), 1.02 (m, 4H)

IR: 3376, 2932, 1655, 1526, 1453, 1322

EXAMPLE 67

Trans-4-guanidino-[(S)-N-[(R)-N'-methanesulfonylphenylalanyl]prolyl] aminomethylcyclohexane (compound No. 646 of Table 1) sulfate To a solution of the compound (0.45 g, 1 mmol) obtained in Example 52 in ethanol (15 ml), a solution of 2-methylisothiourea sulfate (0.14 g, 0.5 mmol) in water (5 ml) is added and heated at reflux for 6 hours. The solvent is evaporated and ether (20 ml) is added. The precipitated white solid is collected and washed with ether, and then dried under reduced pressure to give 0.44 g of the titled compound (81%).

NMR (DMSO-d$^6$) 8.04–2.0 (m, 13H), 2.60–3.96 (m, 7H), 2.77 (s, 3H), 4.14–4.28 (m, 2H), 5.47 (br, 1H), 6.75 (br, 1H), 7.20–7.36 (m, 5H), 7.83 (br, 1H), 8.40 (br, 4H)

IR: 3322, 2932, 2193, 2153, 1644, 1545, 1451, 1319, 1150

According to the same procedure as that described in Example 1, the following compounds of Examples 68 to 78 were synthesized.

EXAMPLE 68

4-Amidino-[(S)-N-[(R)-2-hydroxy-cyclohexylacetyl] prolyl]aminomethylbenzene (compound No. 82 of Table 1) hydrochloride NMR (DMSO-d$^6$) 9.29 (br, 2H), 8.93 (br, 2H), 8.51 (t, 1H), 7.75 (d, 2H), 7.49 (d, 2H), 4.37 (m, 3H), 3.96 (d, 1H), 3.70 (m, 1H), 3.60–3.40 (m, 2H) 2.20–1.0 (m, 14H)

IR: 3227, 2922, 1657, 1607, 1539, 1485, 1458, 1323, 1246, 1032

EXAMPLE 70

4-Amidino-[(S)-N-[(R)-2-methylsulfonylamino-3,3-dimethylbutanoyl]prolyl]aminomethylbenzene (compound No. 114 of Table 1) hydrochloride NMR (DMSO-d$^6$) 9.41 (br, 2H), 9.24 (br, 2H), 8.63 (t, 1H), 7.81 (d, 2H), 7.47 (d, 2H), 7.20 (d, 1H), 4.42 (dd, 1H), 4.35 (t, 2H), 3.96 (d, 1H), 3.80–3.60 (m, 2H), 2.85 (s, 3H), 2.20–1.80 (m, 4H), 0.97 (s, 9H)

IR: 3273, 2970, 2365, 1630, 1541, 1483, 1412, 1304, 1153, 715

EXAMPLE 70

4-Amidino-[(S)-N-[(R)-2-methylsulfonylamino-6-ethoxycarbonylhexanoyl]prolyl]aminomethylbenzene (compound No. 11 7 of Table 1) hydrochloride NMR (DMSO-d$^6$) 9.35 (br, 4H), 8.66 (t, 1H), 7.79 (d, 1H), 7.48 (d, 2H), 4.35 (m, 3H), 4.65 (q, 2H), 3.69 (m, 1H), 3.55 (m, 1H), 2.75 (s, 3H), 2.29 (t, 2H), 2.13 (m, 2H), 1.94 (m, 2H), 1.85 (m, 2H), 1.52 (m, 7H), 1.18 (t, 3H)

IR: 3382, 1644, 1547, 1427, 1375, 1314, 1150, 1111

EXAMPLE 71

4-Amidino-[(S)-N-[(R)-2-methylsulfonylamino-4-(3'-carboxy)-phenylbutanoyl]prolyl]aminomethylbenzene (compound No. 119 of Table 1) hydrochloride NMR (DMSO-d$^6$) 9.45 (s, 2H), 9.38 (s, 2H), 8.62 (t, 1H), 7.84 (m, 2H), 7.79 (d, 2H), 7.64 (d, 1H), 7.47 (d, 2H), 7.42 (m, 2H), 4.33 (m, 3H), 4.1 0 (m, 1H), 3.57–3.37 (m, 2H), 2.85 (m, 1H), 2.78 (s, 3H), 2.73 (m, 1H), 2.12 (m, 1H), 1.95–1.81 (m, 6H)

IR: 3366, 1638, 1543, 1489, 1449, 1311, 1150, 754, 527

EXAMPLE 72

4-Amidino-[(S)-N-[(R)-N'-methylsulfonyl-4-(4'-carboxyphenyl)-seryl]prolyl]aminomethylbenzene (compound No. 970 of Table 1) hydrochloride NMR (DMSO-d$^6$) 9.31 (s, 2H), 9.00 (s, 2H), 8.59 (t, 1H), 7.90 (d, 2H), 7.83 (d, 1H), 7.75 (d, 2H), 7.48 (d, 2H), 7.03 (d, 2H), 4.35 (m, 4H), 4.22 (m, 2H), 4.12 (dd, 1H), 3.72 (m, 2H), 2.89 (s, 3H), 2.20–1.80 (m, 4H)

IR: 3376, 1647, 1607, 1424, 1318, 1252, 1154, 1119, 774, 633, 525

EXAMPLE 73

4-Amidino-[(S)-N-[(R)-N'-methylsulfonyl-O-ethoxycarbonylmethyl-tyrosyl]prolyl]aminomethylbenzene (compound No. 971 of Table 1) hydrochloride NMR (DMSO-d$^6$) 9.41 (br, 2H), 9.20 (br, 2H), 8.56 (t, 1H), 7.80 (d, 2H), 7.65 (d, 1H), 7.48 (d, 2H), 7.18 (dd, 2H), 6.84 (dd, 2H), 4.75 (q, 1H), 4.30 (dd, 1H), 4.30–4.25 (m, 2H), 3.70–3.42 (m, 3H), 3.47 (q, 2H), 3.18 (t, 1H), 2.83 (d, 2H), 2.72 (s, 3H), 1.89–1.60 (m, 4H), 1.14 (dt, 3H)

IR: 3370, 2365, 1742, 1636, 1541, 1512, 1445, 1308

EXAMPLE 74

4-Amidino-[(S)-N-[(R)-N'-ethoxycarbonylphenylalanyl]prolyl]aminomethylbenzene (compound No. 972 of Table 1) hydrochloride NMR (DMSO-d$^6$) 9.40 (br, 2H), 9.24 (br, 2H), 8.14 (t, 1H), 7.80 (d, 2H), 7.59 (t, 1H), 7.40 (d, 2H), 7.31–7.15 (m, 2H), 4.50–4.26 (m, 4H), 3.90–3.57 (m, 3H), 3.0–2.7 (m, 3H), 1.9–1.6 (m, 4H), 1.10–1.0 (m, 3H)

IR: 3279, 2364, 1637, 1539, 1491, 1450, 1255, 704

EXAMPLE 75

4-Amidino-[(S)-N-[(R)-2-methylsulfonylaminoheptanoyl]prolyl]aminomethylbenzene (compound No. 973 of Table 1) hydrochloride NMR (DMSO-d$^6$) 9.37 (s, 2H), 9.16 (s, 2H), 8.60 (t, 1H), 7.76 (d, 2H), 7.48 (d, 2H), 7.40 (d, 1H), 4.50–4.23 (m, 3H), 4.08 (m, 1H), 3.69 (m, 1H), 3.36 (m, 1H), 2.74 (s, 3H), 2.15 (m, 1H), 2.09–1.84 (m, 3H), 1.61–1.22 (m, 8H), 0.87 (m, 3H)

IR: 3366, 2957, 1638, 1543, 1489, 1426, 1314, 1154, 718, 527

EXAMPLE 76

4-Amidino-[(S)-N-[(R)-N'-methylsulfonyl-O-(3'-carboxymethyl-phenyl)seryl]prolyl]aminomethylbenzene (compound No. 974 of Table 1) hydrochloride NMR (DMSO-d$^6$) 9.46 (s, 2H), 9.31 (s, 2H), 8.70 (t, 1H), 7.83 (m, 3H), 7.48 (d, 2H), 7.19 (m, 2H), 6.89 (d, 2H), 4.58 (dd, 1H), 4.37 (m, 4H), 4.14 (d, 2H), 3.70 (m, 1H), 3.60 (m, 3H), 2.89 (s, 3H), 2.11 (m, 1H), 2.01–1.82 (m, 3H)

IR: 3382, 1724, 1640, 1543, 1489, 1447, 1316, 1262, 1154, 768, 527

EXAMPLE 77

4-Amidino-[(S)-N-[(R)-N'-methylsulfonyl-O-(4'-carboxymethyl-phenyl)seryl]prolyl]aminomethylbenzene (compound No. 975 of Table 1) hydrochloride NMR (DMSO-d$^6$) 9.45 (s, 2H), 9.29 (s, 2H), 8.70 (t, 1H), 7.83 (d, 2H), 7.82 (d, 2H), 7.48 (d, 2H), 7.24 (d, 1H), 6.82 (d, 2H), 4.59 (dd, 1H), 4.37 (m, 4H), 4.14 (d, 2H), 3.70 (m, 1H), 3.61 (m, 3H), 2.89 (s, 3H), 2.11 (m, 1H), 2.01–1.82 (m, 3H)

IR: 3383, 1640, 1545, 1514, 1437, 1312, 1242, 1152, 824, 523

EXAMPLE 78

4-Amidino-[(S)-N-[(R)-2-ethoxycarbonylmethylsulfonylamino-heptanoyl]prolyl]aminomethylbenzene (compound No. 976 of Table 1) hydrochloride NMR (DMSO-d$^6$) 9.36 (s, 2H), 9.15 (s, 2H), 8.49 (t, 1H), 7.81 (d, 1H), 7.77 (d, 2H), 7.47 (d, 2H), 4.35 (m, 3H), 4.21 (d, 1H), 4.15 (m, 1H), 4.06 (q, 2H), 3.93 (d, 1H), 3.73 (m, 1H), 3.53 (m, 1H), 2.14 (m, 1H), 1.94 (m, 3H), 1.67–1.18 (m, 8H), 1.14 (t, 3H), 0.89 (m, 3H)

IR: 3274, 2957, 2872, 1821, 1738, 1647, 1541, 1422, 1319, 1159, 1022, 723, 628, 527

According to the same procedures as that described in Example 15, the following compounds of Examples 79 to 86 were synthesized.

EXAMPLE 79

Trans-4-amidino-[(S)-N-[(R)-N'-ethoxycarbonyl-O-t-butyloxy-seryl]prolyl]aminomethylcyclohexane (compound No. 240 of Table 1) hydrochloride NMR (DMSO-d$^6$) 8.88 (br, 2H), 8.71 (br, 2H), 7.72 (m, 1H), 6.39 (m, 1H), 4.59 (m, 1H), 4.52 (m, 1H), 4.11 (m, 2H), 3.86–3.71 (m, 2H), 3.58 (m, 2H), 3.22 (m, 2H), 2.79–0.88 (m, 15H), 1.24 (t, 3H), 1.15 (s, 9H)

IR: 3271, 2976, 1685, 1647, 1541, 1448, 1257, 1192, 1095, 1055

EXAMPLE 80

Trans-4-amidino-[(S)-N-[(R)-N'-isopropoxycarbonyl-O-(1',1'-dimethylpropyl)-seryl]prolyl]aminomethylcyclohexane (compound No. 977 of Table 1) hydrochloride NMR (DMSO-d$^6$) 8.74 (br, 4H), 7.68 (m, 1H), 6.01 (m, 1H), 4.83 (m, 1H), 4.57 (m, 2H), 3.74 (m, 2H), 3.50 (m, 2H), 3.14 (m, 1H), 2.97 (m, 1H), 2.5–0.9 (m, 16H), 1.24 (dd, 6H), 1.09 (s, 6H), 0.81 (t, 3H)

IR: 3314, 2978, 1693, 1641, 1543, 1450, 1375, 1261, 1111, 1059

EXAMPLE 81

Trans-4-amidino-[(S)-N-[(R)-N'-ethoxycarbonyl-O-(1',1'-dimethylpropyl)seryl]prolyl]aminomethylcyclohexane (compound No. 978 of Table 1) hydrochloride NMR (DMSO-d$^6$) 8.75 (br, 4H), 7.55 (m, 1H), 6.40 (m, 1H), 4.52 (m, 2H), 4.13 (m, 2H), 3.88–3.70 (m, 2H), 3.55 (m, 2H), 3.28 (m, 1H), 2.87–2.70 (m, 1H), 2.20–1.20 (m, 14H), 1.27 (t, 3H), 1.09 (s, 6H), 0.81 (t, 3H), 1.10–0.90 (m, 2H)

IR: 3292, 2974, 1689, 1645, 1543, 1448, 1259, 1095, 1055

EXAMPLE 82

Trans-4-amidino-[(S)-N-[(R)-N'-isopropoxycarbonyl-O-(1'-ethyl-1'-methyl-propyl)-seryl]prolyl]aminomethylcyclohexane (compound No. 979 of Table 1) hydrochloride NMR (DMSO-d$^6$) 8.78 (s, 2H), 8.69 (s, 2H), 7.55 (br, 1H), 5.99 (br, 1H), 4.84 (m, 1H), 4.54 (m, 2H), 3.71 (m, 2H), 3.49 (m, 2H), 3.20–0.90 (m, 1 6H), 1.64 (q, 4H), 1.23 (t, 6H), 1.03 (s, 3H), 0.78 (t, 6H)

IR: 3315, 2976, 2934, 1685, 1641, 1543, 1450, 1375, 1261, 1111

EXAMPLE 83

Trans-4-amidino-[(S)-N-[(R)-N'-ethoxycarbonyl-S-t-butyl-cystinyl]prolyl]aminomethylcyclohexane (compound No. 980 of Table 1) hydrochloride NMR (DMSO-d$^6$) 8.82 (br, 2H), 8.74 (br, 2H), 7.47 (m, 1H), 6.63 (m, 1H), 4.60–4.40 (m, 2H), 4.20–4.21 (m, 2H), 4.00 (m, 1H), 3.72 (m, 1H), 3.24 (m, 1H), 2.87 (m, 2H), 2.65 (m, 1H), 2.18–1.31 (m, 12H), 1.31 (s, 9H), 1.27 (t, 3H), 1.10–0.90 (m, 2H),

IR: 3298, 2932, 1693, 1641, 1541, 1448, 1304, 1257, 1161, 1047

EXAMPLE 84

Trans-4-amidino-[(S)-N-[(R)-N'-isopropoxycarbonyl-O-(1'-methylcyclopentyl)-seryl]prolyl]aminomethylcyclohexane (compound No. 981 of Table 1) hydrochloride NMR (DMSO-d$^6$) 8.79 (br, 4H), 7.64 (m, 1H), 5.97 (m, 1H), 4.83 (m, 1H), 4.55 (m, 2H), 3.76 (m, 2H), 3.52 (m, 2H), 3.15–1.20 (m, 22H), 1.27–1.13 (m, 9H), 1.13–0.95 (m, 2H)

IR: 3329, 2934, 1684, 1639, 1541, 1450, 1261, 1182, 1111, 1060, 918

EXAMPLE 85

Trans-4-amidino-[(S)-N-[(R)-N'-isopropoxycarbonyl-O-t-butyl-threonyl]prolyl]aminomethylcyclohexane (compound No.982 of Table 1) hydrochloride NMR (DMSO-d$^6$) 8.74 (m, 4H), 7.80 (m, 1H), 5.66 (m, 1H), 4.85 (m, 1H), 4.57 (m, 1H), 4.29 (m, 1H), 3.80–3.60 (m, 3H), 3.05 (m, 2H), 2.60 (m, 1H), 2.50–1.20 (m, 11H), 1.27–1.22 (m, 1 3H), 1.15 (d, 3H), 1.10–0.90 (m, 2H)

IR: 3331, 2978, 1697, 1639, 1543, 1450, 1375, 1265, 1182, 1111

EXAMPLE 86

Trans-4-amidino-[(S)-N-[(R)-2-ethoxycarbonylamino-3-isopropylthio-3-methyl-butanoyl]prolyl]aminomethylcyclohexane (compound No. 983 of Table 1) hydrochloride NMR (DMSO-d$^6$) 9.13 (br, 2H), 8.46 (br, 2H), 7.30 (m, 1H), 5.85 (m, 1H), 4.55 (m, 1H), 4.36 (m, 1H), 4.15–3.85 (m, 3H), 3.69 (m, 1H), 3.02 (m, 2H), 2.30 (m, 1H), 200–1.20 (m, 13H), 1.48 (s, 3H), 1.33 (s, 3H), 1.30–1.20 (m, 9H), 1.05–0.85 (m, 2H)

IR: 3420, 2974, 1635, 1556, 1521, 1448, 1385, 1298, 1259, 1060

According to the same procedures as that described in Example 24, the following compounds of Examples 87 to 113 were synthesized.

EXAMPLE 87

4-[(S)-N-[(R)-2-hydroxy-cyclohexylacetyl]prolyl]aminomethylbenzamidoxime (compound No. 391 of Table 1)

NMR (DMSO-d$^6$) 9.55 (br, 1H), 8.31 (t, 1H), 7.59 (d, 2H), 7.24 (d, 2H), 5.73 (br, 2H), 4.57 (m 1H), 4.26–4.32 (m, 3H), 3.91 (br, 1H), 3.40–3.60 (m, 2H), 2.05–0.80 (m, 15H)

IR: 3375, 2926, 2853, 1638, 1561, 1451, 1385, 1244

EXAMPLE 88

4-[(S)-N-[(R)-N'-isopropoxycarbonyl-phenylalanyl]prolyl]aminomethylbenzamidoxime (compound No. 395 of Table 1)

NMR (CDCl$_3$) 7.65 (br, 1H), 7.53 (d, 2H), 7.29–7.19 (m, 8H), 5.89 (d, 2H), 5.01 (br, 2H), 4.58–4.45 (m, 4H), 4.27 (dd, 1H), 3.65 (br, 1H), 3.10–2.93 (m, 2H), 2.58 (q, 1H), 2.17 (br, 1H), 1.90–1.50 (m, 2H), 1.11 (d, 4H), 0.96 (d, 2H)

IR: 3331, 2980, 2880, 2365, 1639, 1539, 1452, 126

EXAMPLE 89

4-[(S)-N-[(R)-2-ethoxycarbonylamino-phenylacetyl]prolyl]aminomethylbenzamidoxime (compound No. 403 of Table 1)

NMR (CDCl$_3$) 7.80 (br, 1H), 7.47 (d, 2H), 7.40–7.14 (m, 8H), 6.11 (dd, 1H), 5.43 (dd, 1H), 4.98 (br, 2H), 4.70–4.54 (m, 2H), 4.50–4.20 (m, 1H), 4.15–4.00 (m, 1H), 4.00–3.80 (m, 2H), 3.25–3.19 (m, 1H), 2.30–1.80 (m, 4H), 1. 16 (dt, 3H)

IR: 3339, 2980, 2365, 1641, 1524, 1437, 1385, 1057

EXAMPLE 90

4-[(S)-N-[(R)-N'-ethoxycarbonyl-valyl]prolyl] aminomethylbenzamidoxime (compound No. 407 of Table 1)

NMR (CDCl$_3$) 7.57 (br, 1H), 7.54 (d, 2H), 7.20 (d, 2H), 5.98 (d, 1H), 4.97 (br, 2H), 4.68–4.59(m, 2H), 4.24 (dd, 1H), 4.07 (t, 1H), 4.10–4.00 (m, 1H), 3.90–3.80 (m, 1H), 3.60–3.45 (m, 2H), 2.31 (br, 1H), 2.20–1.95 (m, 4H) 1.88 (d, 1H), 1.01 (t, 3H), 0.97 (d, 6H)

IR: 3337, 2971, 2878, 2363, 1640, 1539, 1445, 1277, 1238

EXAMPLE 91

4-[(S)-N-[(R)-2-ethoxycarbonylamino-3,3-dimethylbutanoyl]prolyl] aminomethylbenzamidoxime (compound No. 409 of Table 1)

NMR (DMSO-d$^6$) 8.01 (br, 1H), 7.59 (d, 2H), 7.21 (d, 2H), 7.19–7.15 (m, 1H), 5.73 (br, 2H), 4.36–4.24 (m, 4H), 4.0–3.60 (m, 4H), 2.10–1.80 (m, 5H), 1.06 (t, 3H), 0.96 (s, 9, H)

IR: 3345, 2966, 2364, 1647, 1535, 1443, 1240

EXAMPLE 92

4-[(S)-N-[(R)-2-ethoxycarbonylamino-heptanoyl) prolyl]aminomethylbenzamidoxime (compound No. 411 of Table 1)

NMR (CDCl$_3$) 7.63 (m, 1H), 7.51 (d, 2H), 7.20 (d, 2H), 5.85 (d, 2H), 4.99 (br, 1H), 4.67–4.58 (m, 2H), 4.35–4.28 (m, 2H), 3.99 (br, 1H), 3.86–3.80 (m, 1H), 3.58–3.50 (m, 2H), 2.31 (br, 1H), 2.07–1.90 (m, 3H), 1.80–1.50 (m, 2H), 1.40–1.10 (m, 5H), 1.03 (t, 3H), 1.01 –0.84 (q13H)

IR: 3347, 2961, 2363, 2342, 1641, 1541, 1447, 1263, 1049

EXAMPLE 93

4-[(S)-N-[(R)-2-t-butyloxycarbonylamino-heptanoyl]prolyl]aminomethylbenzamidoxime (compound No. 412 of Table 1)

NMR (CDCl$_3$) 7.74–7.70 (m, 1H), 7.49 (d, 2H), 7.27 (t, 1H), 7.20 (d, 2H), 5.43 (d, 1H), 4.93 (br, 2H), 4.65 (d, 1H), 4.48–4.25 (m, 3H), 3.93 (br, 1H), 3.50 (q, 1H), 2.40–2.30 (m, 1H), 2.10–1.90 (m, 3H), 1.70–1.50 (m, 2H), 1.42–1.21 (m, 13H), 0.92–0.80 (m, 3H)

IR: 3337, 2961, 2934, 2363, 1641, 1535, 1449, 1368, 1165

EXAMPLE 94

4-[(S)-N-[(R)-2-ethoxycarbonylamino-4,4-dimethylpentanoyl]prolyl] aminomethylbenzamidoxime (compound No. 418 of Table 1)

NMR (CDCl$_3$) 7.58–7.51 (m, 1H), 7.53 (d, 2H), 7.20 (d, 2H), 5.87 (d, 1H), 5.01 (br, 2H), 4.64–4.56 (m, 2H), 4.40 (q, 1H), 4.26 (dd, 1H), 4.10–4.00 (m, 1H), 3.84–3.78 (m, 1H), 3.53–3.47 (m, 2H), 2.32 (br, 1H), 2.10–1.90 (m, 3H), 1.61 (d, 2H), 1.00 (t, 3H), 0.97 (s, 9H)

IR: 3324, 2957, 2263, 2342, 1642, 1541, 1445, 1248, 1059

EXAMPLE 95

4-[(S)-N-[(R)-N'-(ethoxycarbonylmethyl) oxycarbonyl-phenylalanyl]prolyl] aminomethylbenzamidoxime (compound No. 984 of Table 1)

NMR (CDCl$_3$) 7.54 (d, 2H), 7.4 1 (br, 1H), 7.28–7.20 (m, 8H), 6.70 (d, 1H), 5.09 (br, 2H), 4.66 (dd, 1H), 4.60–4.55 (m, 2H), 4.22–4.0 0 (m, 4H), 4.03 (q, 2H), 3.62 (br, 1H), 3.10–3.02 (m, 2H), 2.60–2.40 (m, 1H), 2.14 (br, 1H), 2.00–1.50 (m, 3H), 1.22 (t, 3H)

IR: 3356, 3063, 2980, 2364, 1717, 1641, 1539, 1451, 1213, 702

EXAMPLE 96

4-[(S)-N-[(R)-2-ethoxycarbonylamino-cyclohexylacetyl]prolyl] aminomethylbenzamidoxime (compound No. 985 of Table 1)

NMR (CDCl$_3$) 7.52 (d, 2H), 7.54–7.50 (m, 1H), 7.20 (d, 2H), 6.03 (br, 1H), 4.97 (br, 2H), 4.68 (q, 2H), 4.22 (dd, 1H), 4.12–4.03 (m, 2H), 3.64–3.47 (m, 1H), 3.20 (s, 3H), 2.32 (br, 1H), 2.05–1.60 (m, 9H), 1.28–0.97 (m, 6H)

IR: 3343, 2928, 2853, 2365, 1639, 1541, 1449, 1260

EXAMPLE 97

4-[(S)-N-[(R)-2-ethoxycarbonylamino-2'-thienylacetyl]prolyl]aminomethylbenzamidoxime (compound No. 986 of Table 1)

NMR (CDCl$_3$) 7.80–7.60 (m, 1H), 7.46 (dd, 2H), 7.40–6.95 (m, 5H), 6.13 (dd, 1H), 5.71 (dd, 1H), 4.99 (br, 2H), 4.75–4.20 (m, 3H), 4.00–3.80 (m, 2H), 3.70–3.50 (m, 1H), 3.40–3.30 (m, 1H), 2.40–1.80 (m, 4H), 1.16 (dt, 3H)

IR: 3337, 2978, 2364, 1641, 1524, 1443, 1240, 1057, 710

EXAMPLE 98

4-[(S)-N-[(R)-2-ethoxycarbonylamino-4'-fluorophenylacetyl]prolyl] aminomethylbenzamidoxime (compound No. 987 of Table 1)

NMR (CDCl$_3$) 7.80 (t, 1H), 7.46–7.27 (m, 4H), 7.19–6.92 (m, 4H), 6.19–6.15 (m, 1H), 5.50 (dd, 1H), 5.02 (br, 2H), 4.70–4.20 (m, 3H), 4.10–3.70 (m, 4H), 3.22–3.15 (m, 1H), 2.25–1.80 (m, 4H), 1.16 (dt, 3H)

IR: 3345, 3073, 2980, 2363, 2344, 1641, 1510, 1143

EXAMPLE 99

4-[(S)-N-[(R)-N'-benzyloxycarbonyl-phenylalanyl] prolyl]aminomethylbenzamidoxime (compound No. 988 of Table 1)

NMR (CDCl$_3$) 7.50 (d, 2H), 7.49–7.30 (m, 1H), 7.26–7.12 (m, 12H), 6.40–6.10 (m, 1H), 4.85 (br, 2H), 4.90–4.70 (m, 1H), 4.55–4.40 (m, 4H), 4.30–4.20 (m, 1H) 3.70–3.60 (m, 1H), 3.03–2.95 (m, 1H), 2.20–2.15 (m, 1H), 2.00–1.45 (m, 3H)

EXAMPLE 100

4-[(S)-N-(R)-2-t-butyloxycarbonylamino-4,4-dimethylpentanoyl]prolyl] aminomethylbenzamidoxime (compound No. 989 of Table 1)

NMR (CDCl$_3$) 7.67 (t, 1H), 7.53 (d, 2H), 7.22 (d, 2H), 5.34 (d, 1H), 4.91 (br, 2H), 4.65 (d, 1(H), 4.42–4.34 (m, 3H), 4.00–3.90 (m, 1H), 3.48 (q, 1H), 2.40–2.30 (m, 1H), 2.02–1.95 (m, 3H), 1.56–1.53 (m, 2H), 1.31 (s, 9H), 0.98 (s, 9H)

IR: 3345, 2959, 2367, 1641, 1535, 1446, 1367, 1167

EXAMPLE 101

4-[(S)-N-[(R)-N'-dimethylcarbamoyl-phenylalanyl]prolyl]aminomethylbenzamidoxime (compound No. 990 of Table 1)

NMR (DMSO-d$^6$) 9.56 (s, 1H), 8.11 (t, 1H), 7.56 (d, 2H), 7.18 (d, 2H), 7.29–7.16 (m, 5H 6.70 (d, 1H), 5.74 (br, 2H), 4.40–4.05 (m, 4H), 2.94 (d, 2H), 2.93–2.70 (m, 2H), 2.60 (s, 6H), 1.90–1.60 (m, 4H)

IR: 3306, 2932, 2880, 2363, 2341, 1634, 1541, 1453

EXAMPLE 102

4-[(S)-N-[(S)-N'-benzyloxycarbonyl-β-t-butylaspartyl]prolyl]aminomethylbenzamidoxime (compound No. 991 of Table 1)

NMR (CDCl$_3$) 7.63 (br, 1H), 7.51 (d, 2H), 7.33–7.26 (m, 5H), 7.18 (d, 2H), 6.07 (d, 1H), 5.08 (dd, 2H), 4.92 (br, 2H), 4.90–4.70 (m, 1H), 4.66 (d, 1H), 4.40 (d, 2H), 3.90–3.80 (m, 2H), 3.0–2.90 (m, 1H), 2.55 (dd, 1H), 2.35–2.20 (m, 1H), 2.08–1.90 (m, 3H), 1.25 (s, 9H)

IR: 3364, 3063, 2978, 2363, 2343, 2343, 1717, 1641, 1539, 1450, 1369, 1253,

EXAMPLE 103

Trans-4-[(S)-N-[(R)-N'-ethoxycarbonyl-O-t-butoxy-seryl]prolyl]aminomethylcyclohexanecarboxamidoxime (compound No. 485 of Table 1)

NMR (CDCl$_3$) 7.16 (m, 1H), 5.53 (m, 1H), 4.60–4.53 (m, 2H), 4.47 (s, 2H), 4.13–4.06 (m, 2H), 3.76 (br, 2H), 3.60–3.50 (m, 2H), 3.07 (br, 2H), 2.41 (m, 2H), 2.04–1.20 (m, 12H), 1.27 (t, 3H), 1.16 (s, 9H), 1.03–0.94 (m, 2H)

IR: 3352, 2930, 1701, 1651, 1541, 1448, 1259, 1053, 754

EXAMPLE 104

Trans-4-[(S)-N-[(R)-N'-isopropoxycarbonyl-O-t-butylseryl]prolyl]aminomethylcyclohexanecarboxamidoxime (compound No. 486 of Table 1)

NMR (CDCl$_3$) 7.19 (m, 1H), 5.40 (d, 1H), 4.87 (m, 1H), 4.61–4.53 (m, 2H), 4.47 (br, 2H), 3.75 (m, 2H), 3.60–3.40 (m, 2H), 3.08 (t, 2H), 2.40 (m, 1H), 2.20–1.20 (m, 12H), 1.21 (dd, 6H), 1.19 (s, 9H), 1.10–0.90 (m, 2H)

IR: 3356, 2976, 1697, 1649, 1541, 1448, 1261, 1190, 1109, 1022

EXAMPLE 105

Trans-4-[(S)-N-[(R)-N'-ethoxycarbonyl-O-t-(1',1'-dimethylpropyl]seryl)prolyl]aminomethylcyclohexanecarboxamidoxime (compound No. 487 of Table 1)

NMR (CDCl$_3$) 7.14 (m, 1H), 5.51 (d, 1H), 4.60–4.50 (m, 2H), 4.48 (br, 2H), 4.09 (m, 2H), 3.78 (m, 2H), 3.55–3.45 (m, 2H), 3.06 (m, 2H), 2.35 (m, 1H), 2.20–0.90 (m, 16H), 1.24 (t, 3H), 1.10 (s, 6H), 0.82 (t, 3H)

IR: 3346, 2976, 2930, 1649, 1543, 1448, 1261, 1176, 1095, 1055

EXAMPLE 106

Trans-4-[(S)-N-[(R)-N'-isopropoxycarbonyl-O-(1',1'-dimethylpropyl)seryl]prolyl]aminomethylcyclohexanecarboxamidoxime (compound No. 488 of Table 1)

NMR (CDCl$_3$) 7.18 (m, 1H), 5.38 (d, 1H), 4.86 (m, 1H), 4.61–4.50 (m, 2H), 4.47 (br, 2H), 3.77 (m, 2H), 3.57–3.42 (m, 2H), 3.06 (t, 2H), 2.39 (m, 1H), 2.20–0.90 (m, 16H), 1.23 (dd, 6H), 1.10 (s, 6H), 0.82 (t, 3H)

IR: 3346, 2976, 1703, 1651, 1541, 1448, 1263, 1178, 1109, 1030

EXAMPLE 107

Trans-4-[(S)-N-[(R)-N'-isopropoxycarbonyl-O-(1'-ethyl-1'-methyl-propyl)seryl]prolyl]aminomethylcyclohexanecarboxamidoxime (compound No. 490 of Table 1)

NMR (CDCl$_3$) 7.17 (br, 1H), 5.35 (br, 1H), 4.86 (m, 1H), 4.60–4.50 (m, 2H), 4.47 (br, 2H), 3.78 (m, 2H), 3.53–3.38 (m, 2H), 3.07 (t, 2H), 2.37–1.20 (m, 17H), 1.23 (t, 6H), 1.06 (s, 3H), 1.06–0.82 (m, 2H), 0.79 (t, 6H)

IR: 3350, 2976, 2932, 1651, 1541, 1450, 1375, 1263, 1109, 1026

EXAMPLE 108

Trans-4-[(S)-N-[(R)-N'-ethoxycarbonyl-S-t-butyl-cystinyl]prolyl]aminomethylcyclohexanecarboxamidoxime (compound No. 492 of Table 1)

NMR (CDCl$_3$) 7.27 (m, 1H), 5.81 (m, 1H), 4.60–4.40 (m, 2H), 4.88 (br, 2H), 4.11 (m, 2H), 3.87 (m, 1H), 3.68 (m, 1H), 3.06 (m, 2H), 2.90–2.70 (m, 2H), 2.37 (m, 1H), 200–1.20 (m, 12H), 1.32 (s, 9H), 1.25 (t, 3H), 1.10–0.90 (m, 2H)

IR: 3346, 2930, 1699, 1649, 1541, 1448, 1257, 1163, 1051, 929

EXAMPLE 109

Trans-4-[(S)-N-[(R)-2-ethoxycarbonylamino-3-isopropylthio-3-methylbutanoyl]prolyl]aminomethylcyclohexanecarboxamidoxime (compound No. 497 of Table 1)

NMR (CDCl$_3$) 7.16 (m, 1H), 5.62 (m, 1H), 4.61 (d, 1H), 4.47 (br, 2H), 4.35 (d, 1H), 4.12 (m, 2H), 3.96 (m, 1H), 3.76 (m, 1H), 3.10 (m, 1H), 3.00 (m, 2H), 2.38 (m, 1H), 2.00–1.20 (m, 12H), 1.47 (s, 3H), 1.40 (s, 3H), 1.33–1.25 (m, 9H), 1.00–0.90 (m, 2H)

IR: 3354, 2928, 1653, 1541, 1446, 1367, 1302, 1251, 1155, 1055

EXAMPLE 110

Trans-4-[(S)-N-[(S)-N'-t-butyloxycarbonyl-seryl]prolyl]aminomethylcyclohexanecarboxamidoxime (compound No. 992 of Table 1)

NMR (CDCl$_3$) 7.76 (br, 1H), 6.10 (br, 1H), 5.40 (br, 1H), 4.60 (br, 4H), 3.96 (br, 4H), 3.16–1.21 (m, 15H), 1.40 (s, 9H), 0.99 (br, 2H)

IR: 3314, 2978, 1691, 1639, 1541, 1450, 1367, 1165, 1049

EXAMPLE 111

Trans-4-[(S)-N-[(R)-N'-isopropoxycarbonyl-O-t-butyl-threonyl]prolyl]
aminomethylcyclohexanecarboxamidoxime
(compound No. 993 of Table 1)

NMR (CDCl$_3$) 7.24 (m, 1H), 5.43 (d, 1H), 4.85 (m, 1H), 4.57 (d, 1H), 4.47 (br, 2H), 4.23 (t, 1H), 3.92 (t, 1H), 3.80–3.70 (m, 2H), 3.06 (m, 2H), 2.36 (m, 1H), 2.00–1.20 (m, 12H), 1.23 (s, 9H) 1.23 (dd, 6H), 1.15 (d, 3H), 1.10–0.90 (m, 2H)

IR: 3354, 2978, 1699, 1649, 1543, 1448, 1373, 1257, 1192, 1111, 1032

EXAMPLE 112

Trans-4-[(S)-N-[(R)-2-acetoxy-cyclohexylacetyl]
prolyl]aminomethylcyclohexanecarboxamidoxime
(compound No. 994 of Table 1)

NMR (CDCl$_3$) 6.80 (br, 1H), 4.61 (t, 2H), 4.49 (br, 2H), 3.90–3.84 (m, 1H), 3.51–3.40 (m, 1H), 3.10–2.85 (m, 2H), 2.38 (br, 1H), 2.11 (s, 3H), 2.06–0.80 (m, 25H)

IR: 3484, 3389, 2928, 2855, 1725, 1649, 1451, 1250

EXAMPLE 113

Trans-4-[(S)-N-[(R)-N'-isopropoxycarbonyl-O-(1'-methylcyclopentyl)seryl]prolyl]
aminomethylcyclohexanecarboxamidoxime
(compound No. 995 of Table 1)

NMR (CDCl$_3$) 7.18 (m, 1H), 5.42 (m, 1H), 4.85 (m, 2H), 4.60–4.49 (m, 4H), 3.73 (m, 2H), 3.57–3.42 (m, 2H), 3.08 (m, 1H), 2.40 (m, 1H), 2.04–1.20 (m, 21H), 1.27–1.20 (m, 9H), 1.03–0.94 (m, 2H)

IR: 3356, 2932, 1695, 1653, 1541, 1448, 1263, 1111, 1030, 918

According to the same procedures as that described in Example 48, the following compounds of Examples 114 to 122 were synthesized.

EXAMPLE 114

Trans-4-[(S)-N-[(R)-2-t-butyloxycarbonylamino-4,4-dimethylpentanoyl]prolyl]
aminomethylcyclohexanecarboxamide O-methoxycarbonyloxime (compound No. 533 of Table 1)

NMR (CDCl$_3$) 7.14 (br, 1H), 5.04 (d, 1H), 4.74 (br, 1H), 4.58 (d, 1H), 4.40–4.30 (m, 1H), 4.00–3.85 (m, 1H), 3.94 (s, 3H), 3.46 (q, 1H), 3.30–3.20 (m, 1H), 2.95–2.88 (m, 1H), 2.42 (br, 1H), 2.26 (t, 1H), 2.00–1.73 (m, 11H), 1.54–1.26 (m, 4H), 1.43 (s, 9H), 1.00 (s, 9H)

IR: 3347, 2955, 2870, 1765, 1645,1539, 1443, 1254, 1169, 879

EXAMPLE 115

Trans-4-[(S)-N-[(R)-N'-isopropoxycarbonyl-leucyl]
prolyl]aminomethylcyclohexanecarboxamide O-methoxycarbonyloxime (compound No. 540 of Table 1)

NMR (CDCl$_3$) 7.11 (br, 1H), 5.18 (d, 1H), 4.90–4.70 (m, 1H), 4.77 (br, 2H), 4.56 (d, 1H), 4.40–4.30 (m, 1H), 3.95–3.86 (m, 1H), 3.85 (s, 3H), 3.46 (q, 1H), 3.20–2.95 (m, 2H), 2.40–2.30 (m, 1H), 2.30–2.10 (m, 1H), 2.00–1.20 (m, 13H), 1.23 (dd, 6H), 1.04–0.89 (m, 8H)

IR: 3354, 2957, 2932, 2872, 2363, 2341, 1763, 1643, 1541, 1443, 1260

EXAMPLE 116

Trans-4-[(S)-N-[(R)-N'-ethoxycarbonyl-O-t-butyl-seryl]prolyl]aminomethylcyclohexanecarboxamide
O-methoxycarbonyloxime (compound No. 996 of Table 1)

NMR (CDCl$_3$) 7.20 (m, 1H), 5.34 (m, 1H), 4.70 (s, 2H), 4.61 (m, 1H), 4.50 (m, 1H), 4.12–4.06 (m, 2H), 3.85 (s, 3H), 3.74 (m, 2H), 3.60–3.39 (m, 2H), 3.06 (m, 2H), 2.41–1.20 (m, 13H), 1.25 (t, 3H), 1.16 (s, 9H), 1.08–0.94 (m, 2H)

IR: 3348, 2976, 1768, 1703, 1645, 1541, 1442, 1255, 1053, 879, 752

EXAMPLE 117

Trans-4-[(S)-N-[(R)-2-hydroxy-4-methyl-pentanoyl]
prolyl]aminomethylcyclohexanecarboxamide O-methoxycarbonyloxime (compound No. 997 of Table 1)

NMR (CDCl$_3$) 7.07 (m, 1H), 4.73 (br, 2H), 4.52 (d, 1H), 4.23 (m, 4H), 3.56 (m, 1H), 3.40 (m, 1H), 3.13 (m, 3H), 2.41 (m, 1H), 2.30–0.90 (m, 15H), 1.33 (t, 3H), 0.97 (dd, 6H)

IR: 3346, 2932, 1759, 1641, 1450, 1369, 1251,1078, 920, 846

EXAMPLE 118

Trans-4-[(S)-N-[(R)-N'-ethoxycarbonyl-O-t-butyl-seryl]prolyl]aminomethylcyclohexanecarboxamide
O-acetyloxime (compound No. 998 of Table 1)

NMR (CDCl$_3$) 7.20 (m, 1H), 5.33 (m, 1H), 4.69 (s, 2H), 4.60 (m, 1H), 4.51 (m, 1H), 4.17–4.07 (m, 2H), 3.77–3.65 (m, 2H), 3.60–3.46 (m, 2H), 3.09–3.08 (m, 2H), 2.40–1.00 (m, 13H), 2.15 (s, 3H), 1.25 (t, 3H), 1.16 (s, 9H), 1.14–0.94 (m, 2H) IR: 3346, 2976, 1641, 1541, 1448, 1234, 1053, 754

EXAMPLE 119

Trans-4-[(S)-N-[(R)-N'-isopropoxycarbonyl-O-t-butyl-seryl]prolyl]
aminomethylcyclohexanecarboxamide O-methoxycarbonyloxime (compound No. 999 of Table 1)

NMR (CDCl$_3$) 7.23 (t, 1H), 5.26 (d, 1H), 4.85 (m, 1H), 4.71 (m, 1H), 4.59 (d, 1H), 4.49 (m, 1H), 3.85 (s, 3H), 3.73 (m, 2H), 3.61–3.49 (m, 2H), 3.06 (t, 2H), 2.36 (m, 1H), 2.26 (t, 3H), 2.10–1.20 (m, 11H), 1.21 (dd, 6H), 1.16 (s, 9H), 1.10–0.90 (m, 2H)

IR: 3348, 2978, 1768, 1703, 1649, 1541, 1444, 1259, 1192, 1109

EXAMPLE 120

4-N-ethoxycarbonyl-amidino-[(S)-N-[(R)-2-methylsulfonylamino-4,4-dimethylpentanoyl]prolyl]
aminomethylbenzene
(compound No. 1000 of Table 1)

NMR (CDCl$_3$) 7.29 (d, 2H), 7.30 (d, 2H), 7.23 (t, 1H), 5.53 (br, 1H), 4.52–4.37 (m, 2H), 4.24–4.17 (m, 2H), 4.2 0 (q, 2H), 3.90–3.80 (m, 1H), 3.50–3.40 (m, 1H), 2.77 (s, 3H), 2.28–2.20 (m, 4H), 1.84 (br, 2H), 1.60–1.40 (m, 2H), 1.34 (t, 3H), 1.02 (s, 9H)

IR: 3378, 2957, 2876, 2364, 2230, 1628, 1267, 1147

EXAMPLE 121

4-N-methoxycarbonyl-amidino-[(S)-N-[(R)-2-methylsulfonylamino-cyclohexylacetyl]prolyl]aminomethylbenzene (compound No. 1001 of Table 1)

NMR (CDCl$_3$) 7.78 (d, 2H), 7.29 (d, 2H), 7.27 (t, 1H), 5.49 (d, 1H), 4.56 (d, 1H), 4.42 (dq, 2H), 3.77 (s, 3H), 3.80–3.70 (m, 2H), 3.60–3.51 (m, 1H), 2.79 (s, 3H), 2.23–1.60 (m, 12H), 1.20–0.95 (m, 5H)

IR: 3376, 2930, 2855, 2365, 1626, 1528, 1501, 1439, 1271, 1144

EXAMPLE 122

Trans-4-N-methoxycarbonyl-amidino-[(S)-N-[(R)-2-ethoxycarbonylamino-4,4-dimethylpentanoyl]prolyl]aminomethylcyclohexane (compound No. 599 of Table 1)

NMR (CDCl$_3$) 7.08 (br, 1H), 5.17 (d, 1H), 4.56 (d, 1H), 4.50–4.40 (m, 1H), 4.20–3.80 (m, 3H), 3.70 (s, 3H), 3.47 (q, 1H), 3.20–3.00 (m, 2H), 2.45–2.30 (m, 1H), (m, 15H), 1.24 (t, 3H), 0.99 (s, 9H), 1.10–0.89 (m, 2H)

IR: 3366, 2953, 2365, 1780, 1697, 1640, 1533, 1441, 1271, 1055

According to the same procedures as that described in Example 52, the following compounds of Examples 123 to 125 were synthesized.

EXAMPLE 123

Trans-4-amino-[(S)-N-[(R)-2-carboxymethylsulfonylamino-heptanoyl]prolyl]aminomethylcyclohexane (compound No. 791 of Table 1) hydrochloride NMR (DMSO-d$^6$) 7.97 (m, 2H), 7.57 (m, 1H), 4.19 (m, 2H), 4.01 (d, 1H), 3.80 (d, 1H), 3.68 (m, 1H), 3.50 (m, 1H), 2.88 (m, 3H), 2.04 (m, 1H), 1.90 (m, 5H), 1.73 (m, 4H), 1.58–1.13 (m, 12H), 1.00–0.84 (m, 5H)

IR: 3387, 2934, 1726, 1637, 1553, 1452, 1325, 1159, 1090, 1046, 604

EXAMPLE 124

Trans-4-amino-[(S)-N-[(R)-N'-methylsulfonyl-O-methyltyrosyl]prolyl]aminomethylcyclohexane (compound No. 1002 of Table 1) hydrochloride NMR (DMSO-d$^6$) 8.10 (br, 3H), 7.77 (t, 1H), 7.67 (d, 1H), 7.17 (d, 2H), 6.87 (d, 2H), 4.25–4.16 (m, 1H), 3.75 (br, 2H), 3.73 (s, 3H), 3.57–3.40 (m, 1H), 3.00–2.70 (m, 5H), 2.77 (s, 3H), 2.00–1.71 (m, 8H), 1.40–1.20 (m, 3H), 1.00–0.80 (m, 2H)

IR: 3385, 2936, 2363, 1639, 1514, 1450, 1304, 1248, 1149

EXAMPLE 125

Trans-4-amino-[(S)-N-[(R)-N'-ethoxycarbonyl-O-t-butyloxy-seryl]prolyl]aminomethylcyclohexane (compound No. 1003 of Table 1) hydrochloride NMR (DMSO-d$^6$) 8.29 (s, 3H), 7.20 (s, 1H), 5.69 (d, 1H), 4.58–4.47 (m, 2H), 4.12 (m, 2H), 3.82 (m, 1H), 3.61–3.48 (m, 2H), 3.09 (m, 2H), 2.32–0.86 (m, 15H), 1.27 (t, 3H), 1.16 (s, 9H)

IR: 3358, 2974, 1645, 1541, 1448, 1257, 1192, 1053

According to the same procedures as that described in Example 67, the following compounds 126 to 130 were synthesized.

EXAMPLE 126

Trans-4-(5-methyl-1,3-dioxo-2-on-4-ylmethyl)amino-[(S)-N-[(R)-2hydroxy-cyclohexylacetyl]prolyl]aminomethylcyclohexane (compound No. 966 of Table 1)

NMR (CDCl$_3$) 7.08 (m, 1H), 4.54 (d, 1H), 4.06 (m, 1H), 3.59 (m, 1H), 3.49 (s, 2H), 3.46 (m, 1H), 3.07 (m, 2H), 2.48 (m, 2H), 2.11 (s, 3H), 2.01 (m, 2H), 1.90–1.70 (m, 10H), 1.58 (m, 3H), 1.41–0.94 (m, 10H)

IR: 3387, 2928, 2855, 1821, 1736, 1638, 1543, 1451, 1387, 1223, 1107, 999, 712

EXAMPLE 127

Trans-4-(5-methyl-1,3-dioxo-2-on-4-ylmethyl)amino-[(S)-N-[(R)-N'-methylsulfonyl-phenylalanyl]prolyl]aminomethylcyclohexane (compound No. 967 of Table 1)

NMR (CDCl$_3$) 7.35–7.20 (m, 5H), 6.71 (t, 1H), 5.48 (d, 1H), 4.44 (m, 1H), 4.25 (m, 1H), 3.60 (m, 1H), 3.48 (s, 2H), 3.09 (m, 1H), 2.96 (m, 3H), 2.78 (s, 3H), 2.77 (m, 1H), 2.50 (m, 1H), 2.20 (m, 1H), 2.11 (s, 3H), 1.88–1.56 (m, 8H), 1.42 (m, 1H), 1.24 (m, 2H), 0.96 (m, 2H)

IR: 3387, 2930, 1819, 1736, 1649, 1541, 1499, 1451, 1318, 1223, 1152, 999

EXAMPLE 128

Trans-4-(5-methyl-1,3-dioxo-2-on-4-ylmethyl)amino-[(S)-N-[(R)-2ethoxycarbonylamino-cyclohexylacetyl]prolyl]aminomethylcyclohexane (compound No. 1004 of Table 1)

NMR (CDCl$_3$) 7.11 (m, 1H), 5.31 (m, 1H), 4.58 (d, 1H), 4.10 (t, 2H), 4.04 (m, 1H), 3.94 (m, 1H), 3.56 (m, 1H), 3.49 (s, 2H), 3.04 (m, 2H), 2.52 (m, 1H), 2.36 (m, 2H), 2.12 (s, 3H), 2.00 (m, 3H), 1.92–1.62 (m, 10H), 1.43 (m, 2H), 1.25 (q, 3H), 1.22 (m, 4H), 1.06 (m, 4H)

IR: 3353, 2930, 2855, 1823, 1653, 1537, 1449, 1223, 1040, 999, 772, 627

EXAMPLE 129

Trans-4-(5-methyl-1,3-dioxo-2-on-4-ylmethyl)amino-[(S)-N-[(R)-2isopropoxyamino-4,4-dimethyl prolyl]aminomethylcyclohexane (compound No. 1005 of Table 1)

NMR (CDCl$_3$) 7.10 (m, 1H), 5.07 (d, 1H), 4.83 (m, 1H), 4.57 (d, 1H), 4.40 (m, 1H), 3.96 (m, 1H), 3.48 (s, 2H), 3.45 (m, 2H), 3.04 (m, 2H), 2.50 (m, 1H), 2.39 (m, 1H), 2.11 (s, 3H), 2.00 (m, 3H), 1.83 (m, 3H), 1.69 (m, 5H), 1.57–1.42 (m, 3H), 1.25 (d, 3H), 1.22 (d, 3H), 1.00 (s, 9H)

IR: 3349, 2934, 2872, 1823, 1653, 1537, 1445, 1225, 1047, 999, 712, 627

EXAMPLE 130

Trans-4-(5-methyl-1,3-dioxo-2-on-4-ylmethyl)amino-[(S)-N-[(R)-2methylsulfonylamino-cyclohexylacetyl]prolyl]aminomethylcyclohexane (compound No. 1006 of Table 1)

NMR (CDCl$_3$) 6.69 (t, 1H), 5.26 (d, 1H), 3.82 (m, 2H), 3.54 (m, 2H), 3.49 (s, 2H), 3.13 (m, 1H), 3.00 (m, 1H), 2.96

(s, 3H), 2.51 (m, 1H), 2.30 (m, 1H), 2.11 (s, 3H), 2.02 (m, 4H), 1.80 (m, 9H), 1.61 (m, 2H), 1.43 (m, 1H), 1.20 (m, 5H), 0.97 (m, 3H)

IR: 3376, 2930, 2855, 1642, 1536, 1451, 1352, 1154, 984, 760, 619, 517

EXPERIMENTAL EXAMPLE 1

Determination of antithrombin activity (i) The measuring method for hydrolysis inhibition of synthetic substrate (S-2238)

S-2238 (manufactured by Kabi Co.) is dissolved in a Tris hydrochloric acid buffer solution (pH: 8.3) to prepare a S-2238–0.4M Tris hydrochloric acid solution having a concentration of 80 µm. To 175 µl of the solution, an aqueous solution of a compound of the present invention (515 µl) is added. After incubating at 37° C. for one minute, 10 µl of a bovine thrombin solution (4.4 units/ml, manufactured by Mochida Co., Ltd.) is added. A hydrolysis reaction rate of the substrate is determined by measuring a change in absorbance of 405 nm at 37° C.

The inhibitor concentration exhibiting an absorbance which is half as large as that obtained in case of adding no inhibitor (compound of the present invention) was determined as $I_{50}$ (µm).

(ii) The measuring method for coagulation inhibition of rat plasma The compound of the present invention is dissolved in water or saline to form a solution of a total volume of 0.1 ml. To the solution, 0.1 ml of rat plasma is added and the mixture is incubated at 37° C. for 30 seconds. Then, 0.1 ml of bovine thrombin (8 units/ml, Mochida Co., Ltd.) is added and the coagulation time is measured at 37° C. The concentration of the inhibitor (i.e., the compound of the present invention) which doubles the coagulation time that obtained in the absence of the inhibitor was determined as $I_{50}$ (µm).

(iii) The measuring method for antithrombin activity of rat plasma on oral administration To a rat abstained from bait overnight, an aqueous solution or suspension of the present compound (inhibitor) (30 mg/kg) is orally administered using an oral sound.

After one hour, 2 ml of blood is collected from cava abdominalis and the antithrombin activity in plasma is measured using a method of the above item (ii). As a control experiment, the coagulation time of blood collected from a rat which has not been administered the inhibitor was measured. The extension effect on the coagulation time is represented by the numerical value obtained by comparing the data with those obtained in control experiment, wherein the numerical value obtained in the control experiment was assumed to be 1.

EXPERIMENTAL EXAMPLE 2

Determination of Antitrypsin activity (i) The measuring method for hydrolysis inhibition of synthetic substrate (S-2222)

S-2222 (manufactured by Kabi Co.) is dissolved in a Tris hydrochloric acid (pH: 8.3) to prepare a S-2222–0.4M Tris hydrochloric acid solution having a concentration of 400 µm. To the solution (175 µl), 515 µl of a solution of a compound of the present invention is added. After incubating at 37° C. for one minute, 10 µl of a bovine trypsin solution (1 to 2 mg/ml, manufactured by Sigma Co.) is added. A hydrolysis reaction rate of the substrate is determined by measuring a change in absorbance of 405 nm at 37° C.

The inhibitor concentration exhibiting an absorbance which is half as large as that obtained in case of adding no inhibitor (compound of the present invention) was determined as $I_{50}$ (µm).

The results are shown in Table 2.

TABLE 2

| Example No. | Antithrombin activity $I_{50}$ (µm) Synthetic substrate method | Antithrombin activity $I_{50}$ (µm) Rat plasma method | Antitrypsin activity $I_{50}$ (µm) | Thrombin coagulation time extension coefficient on oral administration |
|---|---|---|---|---|
| 1 | | 0.046 | | 5.97 |
| 2 | | 0.030 | | 8.75 |
| 3 | | 0.027 | | 4.46 |
| 4 | 0.0076 | 0.021 | 0.040 | 6.70 |
| 5 | | 0.048 | | |
| 6 | | 0.056 | | 3.16 |
| 7 | | 0.030 | | |
| 8 | | 0.122 | | |
| 9 | | 0.11 | | |
| 10 | | 0.17 | | |
| 12 | | 0.083 | | |
| 13 | 0.72 | 0.59 | | |
| 15 | 0.011 | 0.038 | 2.2 | |
| 16 | 0.021 | | 1.7 | |
| 17 | 0.015 | 0.053 | 3.2 | |
| 18 | | 0.060 | | |
| 19 | | 0.031 | | |
| 20 | | 0.028 | | |
| 21 | 0.021 | | 1.0 | |
| 22 | 0.014 | | 0.94 | |
| 23 | 0.017 | 0.058 | 3.6 | |
| 24 | | | | 3.28 |
| 25 | >300 | | | 2.82 |
| 26 | | | | 4.16 |
| 27 | | | | 3.52 |
| 28 | | | | 4.35 |
| 30 | | | | 2.75 |
| 31 | | | | 2.77 |
| 32 | | | | 3.58 |
| 33 | | | | 3.99 |
| 35 | | | | 3.72 |
| 36 | | | | 2.85 |
| 37 | | | | 4.37 |
| 39 | | | | 2.37 |
| 40 | | | | 2.70 |
| 41 | | | | 2.94 |
| 42 | | | | 4.36 |
| 43 | | | | 3.09 |
| 46 | | | | 2.16 |
| 47 | | | | 2.34 |
| 48 | | | | 4.91 |
| 49 | | | | 7.12 |
| 50 | | | | 3.50 |
| 51 | | | | 2.80 |
| 52 | 0.13 | 0.045 | 14 | 4.10 |
| 53 | 0.081 | 0.059 | 1.4 | |
| 54 | | 0.23 | | |
| 56 | 0.13 | 0.080 | 14 | 2.10 |
| 57 | | 0.082 | | |
| 58 | | 0.097 | | 2.35 |
| 61 | | 0.056 | | |
| 62 | | 0.088 | | 2.18 |
| 64 | | 0.13 | | 1.25 |
| 65 | | | | 3.67 |
| 67 | 0.56 | 0.081 | 20 | |

EXPERIMENTAL EXAMPLE 3

Acute toxicity test

Acute toxicity was determined in rat. An approximate lethal dose was mined by conducting an oral acute toxicity test using rats. The results are deter in Table 3.

TABLE 3

| Example No. | Approximate lethal dose mg/kg | |
| --- | --- | --- |
| | Male | Female |
| 4 | 750 | 1500 |
| 52 | Not less than 2000 | Not less than 2000 |
| 33 | Not less than 2000 | Not less than 2000 |
| 37 | Not less than 2000 | Not less than 2000 |

What is claimed is:

1. A prolineamide derivative represented by the formula (I):

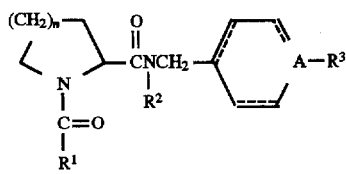

wherein:

A is a carbon atom or a nitrogen atom;

n is an integer of 0 to 2;

a broken line indicates that adjacent carbons are connected by a double or single bond;

$R^1$ is

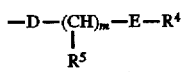

wherein:

D and E independently indicate a single bond or an optionally branched $C_1$–$C_6$ alkylene group;

$R^4$ is a $C_1$–$C_6$ alkyl group;

—$OR^6$, $R^6$ is a hydrogen atom, a $C_1$–$C_6$ alkyl group, an optionally substituted $C_6$–$C_{10}$ aryl group, an optionally substituted $C_3$–$C_8$ cycloalkyl group or an optionally substituted $C_7$–$C_{12}$ aralkyl group;

—$SR^7$, $R^7$ is a $C_1$–$C_6$ alkyl group, an optionally substituted $C_6$–$C_{10}$ aryl group, an optionally substituted $C_3$–$C_8$ cycloalkyl group or an optionally substituted $C_7$–$C_{12}$ aralkyl group;

—$SOR^8$, $R^8$ is an optionally substituted $C_6$–$C_{10}$ aryl group or an optionally substituted $C_3$–$C_8$ cycloalkyl group;

—$SO_2R^9$, $R^9$ is an optionally substituted $C_6$–$C_{10}$ aryl group or an optionally substituted $C_3$–$C_8$ cycloalkyl group;

—$COR^{10}$, $R^{10}$ is a hydroxyl group, a $C_1$–$C_6$ alkoxy group, an optionally substituted $C_6$–$C_{10}$ aryl group or an optionally substituted $C_3$–$C_8$ cycloalkyl group;

—$NHR^{11}$, $R^{11}$ is a $C_1$–$C_6$ alkyl group, an optionally substituted $C_6$–$C_{10}$ aryl group, an optionally substituted $C_3$–$C_8$ cycloalkyl group or an optionally substituted $C_7$–$C_{12}$ aralkyl group;

—$NHCOR^{12}$, $R^{12}$ is a $C_1$–$C_6$ alkoxy group, an optionally substituted $C_6$–$C_{10}$ aryl group, an optionally substituted $C_3$–$C_8$ cycloalkyl group or an optionally substituted $C_7$–$C_{12}$ aralkyloxy group;

—$NHSO_2R^{13}$, $R^{13}$ is a $C_1$–$C_6$ alkyl group, an optionally substituted $C_6$–$C_{10}$ aryl group, an optionally substituted $C_3$–$C_8$ cycloalkyl group, an optionally substituted $C_7$–$C_{12}$ aralkyl group, or an optionally substituted 5- to 10-membered heterocyclic group;

an optionally substituted $C_6$–$C_{10}$ aryl group;

an optionally substituted $C_3$–$C_8$ cycloalkyl group;

an optionally substituted 5- to 10-membered heterocyclic group; or

—$SiR^{14}R^{15}R^{16}$, $R^{14}$, $R^{15}$, and $R^{16}$ independently indicate a $C_1$–$C_6$ alkyl group;

$R^5$ is a —$OR^{17}$, $R^{17}$ is a hydrogen atom,

—$SiR^{22}R^{23}R^{24}$, $R^{22}$, $R^{23}$, and $R^{24}$ independently indicate a $C_1$–$C_6$ alkyl group, a $C_1$–$C_6$ alkyl group, or an optionally substituted 5- to 10-membered heterocyclic group;

—$OCOR^{18}$, $R^{18}$ is a hydrogen atom, a $C_1$–$C_6$ alkyl group, a $C_1$–$C_6$ alkoxy group, an amino group, a $C_1$–$C_6$ alkylamino group, a $C_2$–$C_{12}$ dialkylamino group or a $C_2$–$C_7$ alkenylamino group;

—$NHR^{19}$, $R^{19}$ is a hydrogen atom, a $C_1$–$C_6$ alkyl group or an optionally substituted $C_7$–$C_{12}$ aralkyl group;

—$NHCOR^{20}$, $R^{20}$ is a hydrogen atom, a $C_1$–$C_6$ alkyl group, a $C_1$–$C_6$ haloalkyl group, a $C_1$–$C_6$ alkoxy group, an optionally substituted $C_3$–$C_8$ cycloalkyl group, a $C_2$–$C_7$ carboxyalkyloxy group, a $C_2$–$C_7$ alkenyloxy group, an optionally substituted $C_6$–$C_{10}$ aryl group, an optionally substituted $C_6$–$C_{10}$ aryloxy group, a $C_3$–$C_9$ alkoxycarbonylalkoxy group, a $C_2$–$C_{12}$ dialkylamino group or an optionally substituted $C_7$–$C_{12}$ aralkyloxy group; or

—$NHSO_2R^{21}$, $R^{21}$ is a $C_1$–$C_6$ alkyl group, a $C_1$–$C_6$ haloalkyl group, a $C_2$–$C_7$ carboxylalkyl group, an optionally substituted $C_6$–$C_{10}$ aryl group, a $C_3$–$C_9$ alkoxycarbonylalkyl group or an optionally substituted $C_7$–$C_{12}$ aralkyl group; and m is 0 or 1;

$R^2$ is a hydrogen atom or a $C_1$–$C_6$ alkyl group; and $R^3$ is —$C(=NR^{25})NH_2$, $R^{25}$ is a hydrogen atom, a $C_1$–$C_6$ alkyl group, a $C_2$–$C_7$ acyl group, a $C_2$–$C_7$ acyloxy group, a $C_1$–$C_6$ alkoxy group, a $C_2$–$C_7$ alkoxycarbonyl group, a $C_2$–$C_7$ alkoxycarbonyloxy group, a hydroxyl group or a $C_2$–$C_7$ hydroxyalkylcarbonyloxy group;

—NH—$C(=NR^{25})$ $NH_2$, $R^{25}$ is a defined above; or

—$NHR^{26}$, $R^{26}$ is a hydrogen atom, a $C_1$–$C_6$ alkyl group, a $C_2$–$C_7$ acyl group, a $C_2$–$C_7$ alkoxycarbonyl group or a 5-$C_1$–$C_3$ alkyl-1,3-dioxol-2-on-4-ylmethyl group;

each of said 5- to 10-membered heterocyclic groups is selected from the group consisting of a furan ring, tetrahydrofuran ring, pyran ring, benzofuran ring, chroman ring, thiophene ring, benzothiophene ring, pyrrole ring, imidazole ring, pyrazole ring, triazole ring, pyridine ring, piperidine ring, pyrazine ring, piperazine ring, pyrimidine ring, indole ring, benzimidazole ring, purine ring, quinoline ring, phthalazine ring, guinazoline ring, cinnoline ring, oxazole ring, thiazole ring or morpholine ring;

each of said optional substituents being selected from the group consisting of a $C_1$–$C_6$ alkyl group, a $C_1$–$C_6$ haloalkyl group, a $C_1$–$C_6$ alkoxy group, a hydroxyl group, a carboxyl group, a $C_2$–$C_7$ carboxyalkyl group, a $C_2$–$C_7$ carboxyalkyloxy group, a $C_2$–$C_7$ acyl group, a $C_2$–$C_7$ acyloxy group, a $C_2$–$C_7$ alkoxycarbonyl group, a $C_2$–$C_7$ alkoxycarbonyloxy group, a $C_8$–$C_{13}$ aralkyloxycarbonyl group, a $C_3$–$C_9$ alkoxycarboxyalkoxy group and a halogen atom;

provided that $R^3$ is —C(=NR$^{25}$)NH$_2$ (R$^{25}$ is a defined above) when A is a nitrogen atom, or a salt or hydrate thereof.

2. The compound according to claim 1, wherein A is a carbon atom.

3. The compound according to claim 1, wherein:
n is 1 or 2;
$R^1$ is

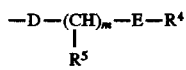

wherein:

D and E independently indicate a single bond or an optionally branched $C_1$–$C_6$ alkylene group;

$R^4$ is a $C_1$–$C_6$ alkyl group;
—OR$^6$, $R^6$ is a $C_1$–$C_6$ alkyl group; a $C_6$–$C_{10}$ aryl group which may be substituted with at least one substituent selected from the group consisting of a $C_1$–$C_6$ alkyl group, a $C_1$–$C_6$ alkoxy group, a halogen atom, a hydroxyl group, a carboxyl group, a $C_2$–$C_7$ alkoxycarbonyl group, a $C_2$–$C_7$ carboxyalkyl group, a $C_2$–$C_7$ acyl group, a $C_2$–$C_7$ acyloxy group, a $C_2$–$C_7$ alkoxycarbonyloxy group, a $C_3$–$C_9$ alkoxycarbonylalkoxy group and a benzyloxycarbonyl group; or a $C_7$–$C_{12}$ aralkyl group which may be substituted with at least one substituent selected from the group consisting of a $C_1$–$C_6$ alkyl group, a $C_1$–$C_6$ alkoxy group, a halogen atom, a hydroxyl group, a carboxyl group, a $C_2$–$C_7$ alkoxycarbonyl group, a $C_2$–$C_7$ carboxyalkyl group, a $C_2$–$C_7$ acyl group, a $C_2$–$C_7$ acyloxy group, a $C_2$–$C_7$ alkoxycarbonyloxy group, a $C_3$–$C_9$ alkoxycarbonylalkoxy group and a benzyloxycarbonyl group;

—SR$^7$, $R^7$ is a $C_1$–$C_6$ alkyl group; a $C_6$–$C_{10}$ aryl group which may be substituted with at least one substituent selected from the group consisting of a $C_1$–$C_6$ alkyl group, a $C_1$–$C_6$ alkoxy group, a halogen atom, a hydroxyl group, a carboxyl group, a $C_2$–$C_7$ alkoxycarbonyl group, a $C_2$–$C_7$ carboxyalkyl group, a $C_2$–$C_7$ acyl group, a $C_2$–$C_7$ acyloxy group, a $C_2$–$C_7$ alkoxycarbonyloxy group, a $C_3$–$C_9$ alkoxycarbonylalkoxy group and a benzyloxycarbonyl group; or a $C_7$–$C_{12}$ aralkyl group which may be substituted with at least one substituent selected from the group consisting of a $C_1$–$C_6$ alkyl group, a $C_1$–$C_6$ alkoxy group, a halogen atom, a hydroxyl group, a carboxyl group, a $C_2$–$C_7$ alkoxycarbonyl group, a $C_2$–$C_7$ carboxyalkyl group, a $C_2$–$C_7$ acyl group, a $C_2$–$C_7$ acyloxy group, a $C_2$–$C_7$ alkoxycarbonyloxy group, a $C_3$–$C_9$ alkoxycarbonylalkoxy group and a benzyloxycarbonyl group;

—COOH;

a $C_6$–$C_{10}$ aryl group which may be substituted with at least one substituent selected from the group consisting of a $C_1$–$C_6$ alkyl group, a $C_1$–$C_6$ alkoxy group, a halogen atom, a hydroxyl group, a carboxyl group, a $C_2$–$C_7$ alkoxycarbonyl group, a $C_2$–$C_7$ carboxyalkyl group, a $C_2$–$C_7$ acyl group, a $C_2$–$C_7$ acyloxy group, a $C_2$–$C_7$ alkoxycarbonyloxy group, a $C_3$–$C_9$ alkoxycarbonylalkoxy group and a benzyloxycarbonyl group;

a $C_3$–$C_8$ cycloalkyl group; or
—SiR$^{14}$R$^{15}$R$^{16}$, $R^{14}$, $R^{15}$, and $R^{16}$ independently indicate a $C_1$–$C_6$ alkyl group;

$R^5$ is —OH,
—OCOR$^{18}$, $R^{18}$ is a $C_1$–$C_6$ alkoxy group or a $C_2$–$C_7$ alkenylamino group;

—NH$_2$;
—NHCOR$^{20}$, $R^{20}$ is a $C_1$–$C_6$ alkoxy group, a $C_6$–$C_{10}$ aryloxy group, a $C_3$–$C_9$ alkoxycarbonylalkoxy group, a $C_2$–$C_{12}$ dialkylamino group or a $C_7$–$C_{12}$ aralkyloxy group; or

—NHSO$_2$R$^{21}$, $R^{21}$ is a $C_1$–$C_6$ alkyl group, a $C_2$–$C_7$ carboxyalkyl group, a $C_6$–$C_{10}$ aryl group, a $C_3$–$C_9$ alkoxycarbonylalkyl group or a $C_7$–$C_{12}$ aralkyl group; and m is 0 or 1;

$R^2$ is a hydrogen atom; and $R^3$ is —C(=NR$^{25}$)NH$_2$, $R^{25}$ is a hydrogen atom, a $C_2$–$C_7$ alkoxycarbonyl group or a hydroxyl group;

—NH—C(=NR$^{25}$)NH$_2$, $R^{25}$ is as defined above; or

—NHR$^{26}$, $R^{26}$ is a hydrogen atom, a $C_2$–$C_7$ alkoxycarbonyl group or a 5-$C_1$–$C_3$ alkyl-1,3-dioxol-2-on-4-ylmethyl group.

4. The compound according to claim 1, wherein:

n is 1;
$R^1$ is

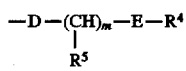

wherein

D and E independently indicate a single bond or an optionally branched $C_1$–$C_6$ alkylene group;

$R^4$ is a $C_1$–$C_6$ alkyl group;
—OR$^6$, $R^6$ is a $C_6$–$C_{10}$ aryl which may be substituted with at least one substituent selected from the group consisting of a $C_1$–$C_6$ alkyl group, a halogen atom, a carboxyl group, a $C_2$–$C_7$ carboxyalkyl group and a benzyloxycarbonyl group or $C_7$–$C_{12}$ aralkyl group;

—SR$^7$, $R^7$ is a $C_1$–$C_6$ alkyl group;

a $C_6$–$C_{10}$ aryl group which may be substituted with at least one substituent selected from the group consisting of a $C_1$–$C_6$ alkyl group, a halogen atom, a carboxyl group, a $C_2$–$C_7$ carboxyalkyl group and a benzyloxycarbonyl group; or a $C_3$–$C_6$ cycloalkyl group;

$R^5$ is —OH;
 $NH_2$;
 —NHCOR$^{20}$,
  $R^{20}$ is a $C_1$–$C_6$ alkoxy group or a $C_7$–$C_{12}$ aralkyloxy group; or
 —NHSO$_2$R$^{21}$,
  $R^{21}$ is a $C_1$–$C_6$ alkyl group or a $C_6$–$C_{10}$ aryl group; and m is 1;

$R^2$ is a hydrogen atom; and $R^3$ is —C(=NR$^{25}$)NH$_2$,
 $R^{25}$ is a hydrogen atom or a hydroxyl group; or
 —NH$_2$.

5. The compound according to claim 1, wherein:

n is 1;

$R^1$ is

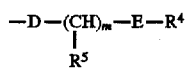

wherein:

D is a single bond;

E is a single bond or a $C_1$–$C_6$ alkylene group;

$R^4$ is a $C_1$–$C_6$ alkyl group;
 —OR$^6$,
  $R^6$ is a $C_6$–$C_{10}$ aryl which may be substituted with at least one substituent selected from the group consisting of a $C_1$–$C_6$ alkyl group, a halogen atom, a carboxyl group, a $C_2$–$C_7$ carboxyalkyl group and a benzyloxycarbonyl group or $C_7$–$C_{12}$ aralkyl group;
 —SR$^7$,
  $R^7$ is a $C_1$–$C_6$ alkyl group;
 a $C_6$–$C_{10}$ aryl group which may be substituted with at least one or more substituents selected from the group consisting of a $C_1$–$C_6$ alkyl group, a halogen atom, a carboxyl group, a $C_2$–$C_7$ carboxyalkyl group and a benzyloxycarbonyl group; or a $C_3$–$C_6$ cycloalkyl group;

$R^5$ is —NH$_2$;
 —NHCOR$^{20}$,
  $R^{20}$ is a $C_1$–$C_6$ alkoxy group or a $C_7$–$C_{12}$ aralkyloxy group; or
 —NHSO$_2$R$^{21}$,
  $R^{21}$ is a $C_1$–$C_6$ alkyl group or a $C_6$–$C_{10}$ aryl group; and m is 1;

$R^2$ is a hydrogen atom; and $R^3$ is —C(=NR$^{25}$)NH$_2$,
 $R^{25}$ is a hydrogen atom or a hydroxyl group; or
 —NH$_2$.

6. The compound according to claim 1, wherein:

A is a carbon atom;

n is 1;

$R^1$ is

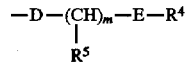

wherein:

D is a single bond;

E is a single bond or a $C_1$–$C_3$ alkylene group;

$R^4$ is a $C_3$–$C_6$ alkyl group,
 —OR$^6$,
  $R^6$ is a $C_1$–$C_6$ alkyl group,
 a phenyl group,
 or a $C_3$–$C_6$ cycloalkyl group;

$R^5$ is —OH;
 —NHR$^{19}$,
  $R^{19}$ is a hydrogen atom;
 —NHCOR$^{20}$,
  $R^{20}$ is a $C_1$–$C_6$ alkoxy group; or
 —NHSO$_2$R$^{21}$,
  $R^{21}$ is a $C_1$–$C_3$ alkyl group; and m is 1;

$R^2$ is a hydrogen atom; and $R^3$ is —C(=NR$^{25}$)NH$_2$,
 $R^{25}$ is a hydrogen atom or a hydroxyl group; or
 —NH$_2$.

7. The compound according to claim 1, wherein:

n is 1;

$R^1$ is

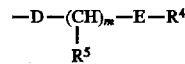

wherein:

D is a single bond;

E is a single bond or a $C_1$–$C_6$ alkylene group;

$R^4$ is a $C_1$–$C_6$ alkyl group;

$R^5$ is —NHCOR$^{20}$,
 $R^{20}$ is a $C_1$–$C_6$ alkoxy group; and m is 1;

$R^2$ is a hydrogen atom; and $R^3$ is —C(=NR$^{25}$)NH$_2$,
 $R^{25}$ is a hydrogen atom or a hydroxyl group.

8. Trans-4-[(S)-N-((R)-2-ethoxycarbonylamino-4,4-dimethylpentanoyl) prolyl] aminomethylcyclohexanecarboxamidoxime or a salt or hydrate thereof.

9. A pharmaceutical composition comprising a compound as claimed in claim 1 and a pharmaceutically acceptable carrier therefor.

* * * * *